US009459249B2

(12) United States Patent
Anderson et al.

(10) Patent No.: US 9,459,249 B2
(45) Date of Patent: *Oct. 4, 2016

(54) PROTEIN LABELING WITH CYANOBENZOTHIAZOLE CONJUGATES

(75) Inventors: Jessica Anderson, Monticello, WI (US); Poncho Meisenheimer, San Luis Obispo, CA (US); John Shultz, Verona, WI (US)

(73) Assignee: PROMEGA CORPORATION, Madison, WI (US)

( * ) Notice: Subject to any disclaimer, the term of this patent is extended or adjusted under 35 U.S.C. 154(b) by 585 days.

This patent is subject to a terminal disclaimer.

(21) Appl. No.: 12/383,832

(22) Filed: Mar. 26, 2009

(65) Prior Publication Data

US 2009/0263843 A1    Oct. 22, 2009

Related U.S. Application Data

(60) Provisional application No. 61/040,173, filed on Mar. 27, 2008.

(51) Int. Cl.

| C07D 417/14 | (2006.01) |
| C07D 493/10 | (2006.01) |
| C07D 495/04 | (2006.01) |
| C09B 11/08  | (2006.01) |
| C09B 11/24  | (2006.01) |
| C09B 23/08  | (2006.01) |
| G01N 33/533 | (2006.01) |

(52) U.S. Cl.
CPC ........... *G01N 33/533* (2013.01); *C07D 417/14* (2013.01); *C07D 493/10* (2013.01); *C07D 495/04* (2013.01); *C09B 11/08* (2013.01); *C09B 11/24* (2013.01); *C09B 23/083* (2013.01)

(58) Field of Classification Search
USPC .................................. 548/152, 159
See application file for complete search history.

(56) References Cited

U.S. PATENT DOCUMENTS

| 5,424,440 | A     | 6/1995  | Klem et al. |
| 5,616,729 | A     | 4/1997  | Schaap et al. |
| 5,728,588 | A     | 3/1998  | Caldwell et al. |
| 5,965,736 | A     | 10/1999 | Akhavan-Tafti |
| 6,130,217 | A *   | 10/2000 | Arnold et al. ............ 514/253.1 |
| 6,376,208 | B1    | 4/2002  | Kajiyama |
| 6,420,130 | B1    | 7/2002  | Makings et al. |
| 7,045,366 | B2 *  | 5/2006  | Huang et al. ................ 436/529 |
| 7,282,339 | B2    | 10/2007 | Beechem et al. |
| 7,951,550 | B2 *  | 5/2011  | Cali et al. ........................ 435/8 |
| 8,309,059 | B2 *  | 11/2012 | Corona et al. ................ 424/9.6 |
| 8,551,721 | B2 *  | 10/2013 | Anderson et al. ................ 435/8 |
| 8,592,172 | B2 *  | 11/2013 | Kelts et al. ........................ 435/8 |
| 9,056,885 | B2 *  | 6/2015  | Kirkland et al. |
| 2003/0165859 | A1 | 9/2003  | Nazarenko et al. |
| 2004/0265870 | A1 | 12/2004 | Lee |
| 2005/0136469 | A1 | 6/2005  | Knapp et al. |
| 2007/0015790 | A1* | 1/2007 | Cali et al. ..................... 514/314 |
| 2007/0054304 | A1 | 3/2007  | Agnew et al. |
| 2007/0093652 | A1 | 4/2007  | Diwu et al. |
| 2007/0134685 | A1 | 6/2007  | Mauro et al. |
| 2007/0155806 | A1 | 7/2007  | Takakura et al. |
| 2007/0178511 | A1 | 8/2007  | Leung et al. |
| 2007/0178512 | A1 | 8/2007  | Leung et al. |
| 2007/0232805 | A1 | 10/2007 | Leung et al. |
| 2007/0264678 | A1 | 11/2007 | Vogel et al. |
| 2008/0039630 | A1 | 2/2008  | Haugland et al. |
| 2010/0075351 | A1* | 3/2010 | Anderson et al. ................. 435/8 |
| 2013/0130289 | A1* | 5/2013 | Benink et al. .................... 435/8 |
| 2013/0317207 | A1* | 11/2013 | Kirkland et al. ........... 536/26.8 |

FOREIGN PATENT DOCUMENTS

| CA | 1341279 | 7/2001 |
| WO | WO-03/066611 A1 * | 8/2003 |
| WO | WO-2004/027378 A2 * | 4/2004 |
| WO | WO-2006/130551 A2 * | 12/2006 |
| WO | 2009/142678 | 11/2009 |

OTHER PUBLICATIONS

Seely, The Journal of Physical Chemistry, vol. 73, No. 1, Jan. 1969, pp. 125-129.*
Lewis et al., Journal of the American Chemical Society, (1944), vol. 66, pp. 2100-2116.*
Feltes, Vom Wasser, (1990), 74, pp. 127-133.*
An English translation of Feltes, Vom Wasser, (1990), 74, pp. 127-133.*
Amess, R. et al., "Synthesis of lucifer in glucosides as substrates for novel ultrasensitive enzyme assays," Carbohydrate Res. (1990) 205:225-233.
Besson, T. et al., "Rapid synthesis of 2-cyanobenzothiazole, isothiocyanate and cyanoformonilide derivatives of dapsone," J. Chem. Soc. (2000) 4:563-566.
English et al., "Conversion of imino-1,2,3,-diathiazoles into 2-cyanobenzothiazoles, cyanoimidoyl chlorides and diatomic sulfur," J. Chem. Soc. (1997) 1:201-205.
Koutentis, P.A. et al., "Reaction of Herz salts with malononitrile: a general route to (6h-1,2,3-benzodithiazol-6-ylidene)malonon itriles," J. Chem. Soc. (2002) 3:315-319.
Schuler, B. et al., "Specific labeling of polypeptides at amino-terminal cysteine residues using Cy5-benzyl thioester," Bioconj. Chem. (2002) 13(5):1039-1043.

(Continued)

*Primary Examiner* — Laura L. Stockton
(74) *Attorney, Agent, or Firm* — Michael Best & Friedrich LLP

(57) ABSTRACT

The invention provides compounds and methods for site-specifically labeling proteins with cyanobenzothiazole derivatives of formula I. For example, the invention provides methods for labeling the N-terminus of a protein that terminates with a cysteine residue. The invention also provides methods for isolating an N-terminally labeled protein and methods for detecting an N-terminally labeled protein.

6 Claims, 9 Drawing Sheets

(56) References Cited

OTHER PUBLICATIONS

Toya, Y. et al., "Improved synthetic methods of firefly luciferin derivatives for use in bioluminescent analysis of hydrolytic enzymes; carboxylic esterase and alkaline phosphatase," Bull. Chem. Soc. JP (1992) 65(10):2604-2610.
Yao, H. et al., "A bioluminogenic substrate for in vivo imaging of beta-lactamase activity," Angewandte Chemie (2007) 46(37):7031-7034.
Zhou, W. et al., "Electrophilic aromatic substituted luciferins as bioluminescent probes for glutathione S-transferase assays," Chem. Comm. (2006) 44:4620-4622.
Zhou, W. et al., "New bioluminogenic substrates for monoamine oxidase assays," J. Am. Chem. Soc. (2006) 128 (10):3122-3123.
European Patent Office Action for Application No. 09750909.5 dated Feb. 24, 2011 (5 pages).
International Search Report and Written Opinion for Application No. PCT/US2009/001905 dated Oct. 26, 2009 (12 pages).
Becker, C. F. W., et al., "C-Terminal Fluorescence Labeling of Proteins for Interaction Studies on the Single-Molecule Level", *ChemBioChem*, 7(6), (2006), 891-895.
Carreras, C. W., et al., "A C-Terminal Conformational Equilibrium in Thymidylate Synthase Observed by Electron Paramagnetic Resonance Spectroscopy", *Biochemistry*, 33(8), (1994), 2071-2077.
Chen, Q., et al., "Construction, properties and specific flurescent labeling of a bovine prothrombin mutant engineered with a free C-terminal cysteine", *Protein Engineeering*, 9(6), (1996), 545-553.
Dirksen, A., et al., "Strategy for the synthesis of multivalent peptide-based nonsymmetric dendrimers by native chemical ligation", *Chem. Commun.*, (2006), 1667-1669.
Hong, S.-H., et al., "Domain-specific fluorescence resonance energy transfer (FRET) sensors of metallothionein/thionein", *Protein Engineering Design and Section*, 18(6), (2005), 255-263.
Kapanidis, A. N., et al., "Fluorescent probes and bioconjugation chemistries for single-molecule fluorescence analysis of biomolecules", *Journal of Chemical Physics*, 117(24), (2002), 10953-10964.
Kushnir, S., et al., "Rapid Production of Functionalized Recombinant Proteins: Marrying Ligation Independent Cloning and In Vitro Protein Ligation", *Bioconjugate Chem.*, 17, (2006), 610-617.
Lequin, R. M., "Enzyme Immunoassay (EIA)/Enzyme-Linked Immunosorbent Assay (ELISA)", *Clinical Chemistry*, 51 (12), (2005), 2415-2418.
O'Brien, M. A, et al., "Homogeneous Bioluminescent Protease Assays : Caspase-3 as a Model", *Journal of Biomolecular Screening*,10(2), (2005), 137-148.
Schuette, C. G., et al., "Determinants of liposome fusion mediated by synaptic SNARE proteins", *Proc. Nat'l Acad. Sci. USA*, 101(9), (2004), 2858-2863.
European Patent Office Action for Application No. 09750909.5 dated Jul. 8, 2013 (6 pages).
European Patent Office Search Report for Application No. 13156458.5 dated Jul. 17, 2013 (16 pages).
Hongjun, R. et al., "A Biocompatible Condensation Reaction for the Labeling of Terminal Cysteine Residues on Proteins," Angewandte Chemie International Edition, vol. 48, No. 51, Dec. 41, 2009, pp. 9658-9662.
Japanese Office Action for 2011-501816 dated Dec. 2, 2013 (12 pages, with English translation).
Japanese Office Action for 2011-501816 dated Oct. 6, 2014 (4 pages, with English translation).
European Patent Office Action for Application No. 09750909.5 dated Mar. 11, 2015 (5 pages).
European Patent Office Action for Application No. 13156458.5 dated Nov. 26, 2015 (7 pages).
Po-Chiao Lin et al., "Site-Specific Protein Modification through CuI-Catalyzed 1,2,3-Triazole Formation and Its Implementation in Protein Microarray Fabrication", Angewandte Chemie International Edition, vol. 45, No. 26, Jun. 26, 2006, pp. 4286-4290.
Anja Watzke et al: "Site-Selective Protein Immobilization by Staudinger Ligation", Angewandte Chemie International Edition, vol. 45, No. 9, Feb. 20, 2006, pp. 1408-1412.
Japanese Patent Office Action for Application No. 2015-132893 dated Jul. 25, 2016 (6 pages, with English translation).

\* cited by examiner

PBI 3086

PBI 3082

PBI 3080

PBI 3087

PBI 3081

PBI 3028

PBI 3066

PBI 3128

PBI 3132

PBI 3173

PBI 3170

PBI 3168

PBI 3167

PBI 3272

```
                         SEQUENCE LISTING

<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: a synthetic peptide

<400> SEQUENCE: 1

His His His His His
1               5

<210> SEQ ID NO 2
<211> LENGTH: 6
<212> TYPE: PRT
<213> ORGANISM: Artificial Sequence
<220> FEATURE:
<223> OTHER INFORMATION: a synthetic peptide

<400> SEQUENCE: 2

His His His His His His
1               5

<210> SEQ ID NO 3
<211> LENGTH: 10
<212> TYPE: PRT
<213> ORGANISM: Homo sapiens

<400> SEQUENCE: 3

Glu Gln Lys Leu Ile Ser Glu Glu Asp Leu
1               5                   10

<210> SEQ ID NO 4
<211> LENGTH: 8
<212> TYPE: PRT
<213> ORGANISM: Artificial Sequence
<220> FEATURE:
<223> OTHER INFORMATION: a synthetic peptide

<400> SEQUENCE: 4

Asp Tyr Lys Asp Asp Asp Asp Lys
1               5

<210> SEQ ID NO 5
<211> LENGTH: 8
<212> TYPE: PRT
<213> ORGANISM: Artificial Sequence
```

```
<220> FEATURE:
<223> OTHER INFORMATION: a synthetic peptide

<400> SEQUENCE: 5

Trp Ser His Pro Gln Phe Glu Lys
 1               5

<210> SEQ ID NO 6
<211> LENGTH: 9
<212> TYPE: PRT
<213> ORGANISM: Influenza A virus

<400> SEQUENCE: 6

Tyr Pro Tyr Asp Val Pro Asp Tyr Ala
 1               5

<210> SEQ ID NO 7
<211> LENGTH: 6
<212> TYPE: PRT
<213> ORGANISM: Homo sapiens

<400> SEQUENCE: 7

Cys Tyr Ile Gln Asn Cys
 1               5

<210> SEQ ID NO 8
<211> LENGTH: 8
<212> TYPE: PRT
<213> ORGANISM: Homo sapiens

<400> SEQUENCE: 8

Gly Cys Lys Asn Phe Phe Trp Lys
 1               5

<210> SEQ ID NO 9
<211> LENGTH: 8
<212> TYPE: PRT
<213> ORGANISM: Homo sapiens

<400> SEQUENCE: 9

Cys Lys Asn Phe Phe Trp Lys Thr
 1               5

<210> SEQ ID NO 10
<211> LENGTH: 784
<212> TYPE: PRT
<213> ORGANISM: Artificial Sequence
<220> FEATURE:
<223> OTHER INFORMATION: a synthetic peptide

<400> SEQUENCE: 10

Met Ser Pro Ile Leu Gly Tyr Trp Lys Ile Lys Gly Leu Val Gln Pro
 1               5                  10                  15

Thr Arg Leu Leu Leu Glu Tyr Leu Glu Glu Lys Tyr Glu Glu His Leu
                20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95
```

-continued

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Gly Gly Gly Gly Gly
    210                 215                 220

Glu Asn Leu Tyr Phe Gln Cys Ile Ala Met Glu Asp Ala Lys Asn Ile
225                 230                 235                 240

Lys Lys Gly Pro Ala Pro Phe Tyr Pro Leu Glu Asp Gly Thr Ala Gly
                245                 250                 255

Glu Gln Leu His Lys Ala Met Lys Arg Tyr Ala Leu Val Pro Gly Thr
            260                 265                 270

Ile Ala Phe Thr Asp Ala His Ile Glu Val Asn Ile Thr Tyr Ala Glu
        275                 280                 285

Tyr Phe Glu Met Ser Val Arg Leu Ala Glu Ala Met Lys Arg Tyr Gly
    290                 295                 300

Leu Asn Thr Asn His Arg Ile Val Val Cys Ser Glu Asn Ser Leu Gln
305                 310                 315                 320

Phe Phe Met Pro Val Leu Gly Ala Leu Phe Ile Gly Val Ala Val Ala
                325                 330                 335

Pro Ala Asn Asp Ile Tyr Asn Glu Arg Glu Leu Leu Asn Ser Met Asn
            340                 345                 350

Ile Ser Gln Pro Thr Val Val Phe Val Ser Lys Lys Gly Leu Gln Lys
        355                 360                 365

Ile Leu Asn Val Gln Lys Lys Leu Pro Ile Ile Gln Lys Ile Ile Ile
    370                 375                 380

Met Asp Ser Lys Thr Asp Tyr Gln Gly Phe Gln Ser Met Tyr Thr Phe
385                 390                 395                 400

Val Thr Ser His Leu Pro Pro Gly Phe Asn Glu Tyr Asp Phe Val Pro
                405                 410                 415

Glu Ser Phe Asp Arg Asp Lys Thr Ile Ala Leu Ile Met Asn Ser Ser
            420                 425                 430

Gly Ser Thr Gly Leu Pro Lys Gly Val Ala Leu Pro His Arg Thr Ala
        435                 440                 445

Cys Val Arg Phe Ser His Ala Arg Asp Pro Ile Phe Gly Asn Gln Ile
    450                 455                 460

Ile Pro Asp Thr Ala Ile Leu Ser Val Val Pro Phe His His Gly Phe
465                 470                 475                 480

Gly Met Phe Thr Thr Leu Gly Tyr Leu Ile Cys Gly Phe Arg Val Val
                485                 490                 495

Leu Met Tyr Arg Phe Glu Glu Glu Leu Phe Leu Arg Ser Leu Gln Asp
            500                 505                 510

```
Tyr Lys Ile Gln Ser Ala Leu Leu Val Pro Thr Leu Phe Ser Phe Phe
            515                 520                 525

Ala Lys Ser Thr Leu Ile Asp Lys Tyr Asp Leu Ser Asn Leu His Glu
530                 535                 540

Ile Ala Ser Gly Gly Ala Pro Leu Ser Lys Glu Val Gly Glu Ala Val
545                 550                 555                 560

Ala Lys Arg Phe His Leu Pro Gly Ile Arg Gln Gly Tyr Gly Leu Thr
                565                 570                 575

Glu Thr Thr Ser Ala Ile Leu Ile Thr Pro Glu Gly Asp Asp Lys Pro
            580                 585                 590

Gly Ala Val Gly Lys Val Val Pro Phe Phe Glu Ala Lys Val Val Asp
        595                 600                 605

Leu Asp Thr Gly Lys Thr Leu Gly Val Asn Gln Arg Gly Glu Leu Cys
610                 615                 620

Val Arg Gly Pro Met Ile Met Ser Gly Tyr Val Asn Asn Pro Glu Ala
625                 630                 635                 640

Thr Asn Ala Leu Ile Asp Lys Asp Gly Trp Leu His Ser Gly Asp Ile
                645                 650                 655

Ala Tyr Trp Asp Glu Asp Glu His Phe Phe Ile Val Asp Arg Leu Lys
            660                 665                 670

Ser Leu Ile Lys Tyr Lys Gly Tyr Gln Val Ala Pro Ala Glu Leu Glu
        675                 680                 685

Ser Ile Leu Leu Gln His Pro Asn Ile Phe Asp Ala Gly Val Ala Gly
        690                 695                 700

Leu Pro Asp Asp Asp Ala Gly Glu Leu Pro Ala Ala Val Val Val Leu
705                 710                 715                 720

Glu His Gly Lys Thr Met Thr Glu Lys Glu Ile Val Asp Tyr Val Ala
                725                 730                 735

Ser Gln Val Thr Thr Ala Lys Lys Leu Arg Gly Gly Val Val Phe Val
            740                 745                 750

Asp Glu Val Pro Lys Gly Leu Thr Gly Lys Leu Asp Ala Arg Lys Ile
        755                 760                 765

Arg Glu Ile Leu Ile Lys Ala Lys Lys Gly Gly Lys Ser Lys Leu Val
770                 775                 780

<210> SEQ ID NO 11
<211> LENGTH: 2355
<212> TYPE: DNA
<213> ORGANISM: Artificial Sequence
<220> FEATURE:
<223> OTHER INFORMATION: a synthetic oligonucleotide

<400> SEQUENCE: 11 atgtcccta tactaggtta ttggaaaatt aagggccttg tgcaacccac tcgacttctt      60
ttggaatatc ttgaagaaaa atatgaagag catttgtatg agcgcgatga aggtgataaa    120
tggcgaaaca aaagtttgaa attgggtttg agtttcccca tcttccctta ttatattgat    180
ggtgatgtta aattaacaca gtctatggcc atcatacgtt atatagctga caagcacaac    240
atgttgggtg ttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttga atggtgatca tgtaacccat cctgacttca tgttgtatga cgctcttgat    480
gttgttttat acatggaccc aatgtgcctg gatgcgttcc caaaattagt ttgtttcaaa    540
```

```
aaacgtattg aagctatccc acaaattgat aagtacttga atccagcaa gtatatagca    600
tggcctttgc agggctggca agccacgttt ggtggtggcg accatcctcc aaaatccgga    660
ggtggtggcg agaaaaacct gtacttccaa tgcatcgcca tggaagacgc caaaaacata    720
aagaaaggcc cggcgccatt ctatcctcta gaggatggaa ccgctggaga gcaactgcat    780
aaggctatga agagatacgc cctggttcct ggaacaattg cttttacaga tgcacatatc    840
gaggtgaaca tcacgtacgc ggaatacttc gaaatgtccg ttcggttggc agaagctatg    900
aaacgatatg ggctgaatac aaatcacaga atcgtcgtat gcagtgaaaa ctctcttcaa    960
ttctttatgc cggtgttggg cgcgttattt atcggagttg cagttgcgcc cgcgaacgac   1020
atttataatg aacgtgaatt gctcaacagt atgaacattt cgcagcctac cgtagtgttt   1080
gtttccaaaa aggggttgca aaaaattttg aacgtgcaaa aaaaattacc aataatccag   1140
aaaattatta tcatggattc taaaacggat taccagggat tcagtcgat gtacacgttc    1200
gtcacatctc atctacctcc cggttttaat gaatacgatt ttgtaccaga gtcctttgat   1260
cgtgacaaaa caattgcact gataatgaat tcctctggat ctactgggtt acctaagggt   1320
gtggcccttc cgcatagaac tgcctgcgtc agattctcgc atgccagaga tcctattttt   1380
ggcaatcaaa tcattccgga tactgcgatt ttaagtgttg ttccattcca tcacggtttt   1440
ggaatgttta ctacactcgg atatttgata tgtggatttc gagtcgtctt aatgtataga   1500
tttgaagaag agctgttttt acgatccctt caggattaca aaattcaaag tgcgttgcta   1560
gtaccaaccc tattttcatt cttcgccaaa agcactctga ttgacaaata cgatttatct   1620
aatttacacg aaattgcttc tgggggcgca cctctttcga aagaagtcgg ggaagcggtt   1680
gcaaaacgct tccatcttcc agggatacga caaggatatg ggctcactga gactacatca   1740
gctattctga ttacacccga gggggatgat aaaccgggcg cggtcggtaa agttgttcca   1800
ttttttgaag cgaaggttgt ggatctggat accgggaaaa cgctgggcgt taatcagaga   1860
ggcgaattat gtgtcagagg acctatgatt atgtccggtt atgtaaacaa tccggaagcg   1920
accaacgcct tgattgacaa ggatggatgg ctacattctg gagacatagc ttactgggac   1980
gaagacgaac acttcttcat agttgaccgc ttgaagtctt taattaaata caaaggatat   2040
caggtggccc ccgctgaatt ggaatcgata ttgttacaac accccaacat cttcgacgcg   2100
ggcgtggcag gtcttcccga cgatgacgcc ggtgaacttc ccgccgccgt tgttgttttg   2160
gagcacggaa agacgatgac ggaaaaagag atcgtggatt acgtcgccag tcaagtaaca   2220
accgcgaaaa agttgcgcgg aggagttgtg tttgtggacg aagtaccgaa aggtcttacc   2280
ggaaaactcg acgcaagaaa aatcagagag atcctcataa aggccaagaa gggcggaaag   2340
tccaaattgg tttaa                                                    2355
```

<210> SEQ ID NO 12
<211> LENGTH: 783
<212> TYPE: PRT
<213> ORGANISM: Artificial Sequence
<220> FEATURE:
<223> OTHER INFORMATION: a synthetic peptide

<400> SEQUENCE: 12

Ser Pro Ile Leu Gly Tyr Trp Lys Ile Lys Gly Leu Val Gln Pro Thr
 1               5                  10                  15

Arg Leu Leu Leu Glu Tyr Leu Glu Glu Lys Tyr Glu Glu His Leu Tyr
             20                  25                  30

```
Glu Arg Asp Glu Gly Asp Lys Trp Arg Asn Lys Lys Phe Glu Leu Gly
         35                  40                  45

Leu Glu Phe Pro Asn Leu Pro Tyr Tyr Ile Asp Gly Asp Val Lys Leu
 50                      55                  60

Thr Gln Ser Met Ala Ile Ile Arg Tyr Ile Ala Asp Lys His Asn Met
 65                      70                  75                  80

Leu Gly Gly Cys Pro Lys Glu Arg Ala Glu Ile Ser Met Leu Glu Gly
                 85                  90                      95

Ala Val Leu Asp Ile Arg Tyr Gly Val Ser Arg Ile Ala Tyr Ser Lys
                100                 105                 110

Asp Phe Glu Thr Leu Lys Val Asp Phe Leu Ser Lys Leu Pro Glu Met
             115                 120                 125

Leu Lys Met Phe Glu Asp Arg Leu Cys His Lys Thr Tyr Leu Asn Gly
     130                 135                 140

Asp His Val Thr His Pro Asp Phe Met Leu Tyr Asp Ala Leu Asp Val
145                 150                 155                 160

Val Leu Tyr Met Asp Pro Met Cys Leu Asp Ala Phe Pro Lys Leu Val
                 165                 170                 175

Cys Phe Lys Lys Arg Ile Glu Ala Ile Pro Gln Ile Asp Lys Tyr Leu
             180                 185                 190

Lys Ser Ser Lys Tyr Ile Ala Trp Pro Leu Gln Gly Trp Gln Ala Thr
     195                 200                 205

Phe Gly Gly Asp His Pro Pro Lys Ser Gly Gly Gly Gly Glu
210                 215                 220

Asn Leu Tyr Phe Gln Ala Ile Ala Met Glu Asp Ala Lys Asn Ile Lys
225                 230                 235                 240

Lys Gly Pro Ala Pro Phe Tyr Pro Leu Glu Asp Gly Thr Ala Gly Glu
                245                 250                 255

Gln Leu His Lys Ala Met Lys Arg Tyr Ala Leu Val Pro Gly Thr Ile
             260                 265                 270

Ala Phe Thr Asp Ala His Ile Glu Val Asn Ile Thr Tyr Ala Glu Tyr
         275                 280                 285

Phe Glu Met Ser Val Arg Leu Ala Glu Ala Met Lys Arg Tyr Gly Leu
     290                 295                 300

Asn Thr Asn His Arg Ile Val Val Cys Ser Glu Asn Ser Leu Gln Phe
305                 310                 315                 320

Phe Met Pro Val Leu Gly Ala Leu Phe Ile Gly Val Ala Val Ala Pro
                325                 330                 335

Ala Asn Asp Ile Tyr Asn Glu Arg Glu Leu Leu Asn Ser Met Asn Ile
             340                 345                 350

Ser Gln Pro Thr Val Val Phe Val Ser Lys Lys Gly Leu Gln Lys Ile
         355                 360                 365

Leu Asn Val Gln Lys Lys Leu Pro Ile Ile Gln Lys Ile Ile Ile Met
     370                 375                 380

Asp Ser Lys Thr Asp Tyr Gln Gly Phe Gln Ser Met Tyr Thr Phe Val
385                 390                 395                 400

Thr Ser His Leu Pro Pro Gly Phe Asn Glu Tyr Asp Phe Val Pro Glu
                405                 410                 415

Ser Phe Asp Arg Asp Lys Thr Ile Ala Leu Ile Met Asn Ser Ser Gly
             420                 425                 430

Ser Thr Gly Leu Pro Lys Gly Val Ala Leu Pro His Arg Thr Ala Cys
         435                 440                 445
```

Val Arg Phe Ser His Ala Arg Asp Pro Ile Phe Gly Asn Gln Ile Ile
450                 455                 460

Pro Asp Thr Ala Ile Leu Ser Val Val Pro Phe His His Gly Phe Gly
465                 470                 475                 480

Met Phe Thr Thr Leu Gly Tyr Leu Ile Cys Gly Phe Arg Val Val Leu
            485                 490                 495

Met Tyr Arg Phe Glu Glu Leu Phe Leu Arg Ser Leu Gln Asp Tyr
        500                 505                 510

Lys Ile Gln Ser Ala Leu Leu Val Pro Thr Leu Phe Ser Phe Ala
        515                 520                 525

Lys Ser Thr Leu Ile Asp Lys Tyr Asp Leu Ser Asn Leu His Glu Ile
530                 535                 540

Ala Ser Gly Gly Ala Pro Leu Ser Lys Glu Val Gly Glu Ala Val Ala
545                 550                 555                 560

Lys Arg Phe His Leu Pro Gly Ile Arg Gln Gly Tyr Gly Leu Thr Glu
            565                 570                 575

Thr Thr Ser Ala Ile Leu Ile Thr Pro Glu Gly Asp Asp Lys Pro Gly
            580                 585                 590

Ala Val Gly Lys Val Val Pro Phe Phe Glu Ala Lys Val Val Asp Leu
            595                 600                 605

Asp Thr Gly Lys Thr Leu Gly Val Asn Gln Arg Gly Glu Leu Cys Val
610                 615                 620

Arg Gly Pro Met Ile Met Ser Gly Tyr Val Asn Asn Pro Glu Ala Thr
625                 630                 635                 640

Asn Ala Leu Ile Asp Lys Asp Gly Trp Leu His Ser Gly Asp Ile Ala
            645                 650                 655

Tyr Trp Asp Glu Asp Glu His Phe Phe Ile Val Asp Arg Leu Lys Ser
            660                 665                 670

Leu Ile Lys Tyr Lys Gly Tyr Gln Val Ala Pro Ala Glu Leu Glu Ser
        675                 680                 685

Ile Leu Leu Gln His Pro Asn Ile Phe Asp Ala Gly Val Ala Gly Leu
        690                 695                 700

Pro Asp Asp Asp Ala Gly Glu Leu Pro Ala Ala Val Val Val Leu Glu
705                 710                 715                 720

His Gly Lys Thr Met Thr Glu Lys Glu Ile Val Asp Tyr Val Ala Ser
            725                 730                 735

Gln Val Thr Thr Ala Lys Lys Leu Arg Gly Gly Val Val Phe Val Asp
            740                 745                 750

Glu Val Pro Lys Gly Leu Thr Gly Lys Leu Asp Ala Arg Lys Ile Arg
        755                 760                 765

Glu Ile Leu Ile Lys Ala Lys Lys Gly Gly Lys Ser Lys Leu Val
770                 775                 780

<210> SEQ ID NO 13
<211> LENGTH: 2354
<212> TYPE: DNA
<213> ORGANISM: Artificial Sequence
<220> FEATURE:
<223> OTHER INFORMATION: a synthetic oligonucleotide

<400> SEQUENCE: 13 atgtcccta tactaggtta ttggaaaatt aagggccttg tgcaacccac tcgacttctt        60
ttggaatatc ttgaagaaaa atatgaagag catttgtatg agcgcgatga aggtgataaa      120
tggcgaaaca aaaagtttga attgggtttg gagtttccca atcttcctta ttatattgat      180

-continued

```
ggtgatgtta aattaacaca gtctatggcc atcatacgtt atatagctga caagcacaac    240
atgttgggtg gttgtccaaa agagcgtgca gagatttcaa tgcttgaagg agcggttttg    300
gatattagat acggtgtttc gagaattgca tatagtaaag actttgaaac tctcaaagtt    360
gattttctta gcaagctacc tgaaatgctg aaaatgttcg aagatcgttt atgtcataaa    420
acatatttga atggtgatca tgtaacccat cctgacttca tgttgtatga cgctcttgat    480
gttgttttat acatggaccc aatgtgcctg atgcgttcc caaaattagt ttgtttcaaa     540
aaacgtattg aagctatccc acaaattgat aagtacttga atccagcaa gtatatagca    600
tggcctttgc agggctggca agccacgttt ggtggtggcg accatcctcc aaaatccgga    660
ggtggtggcg agaaaaacct gtacttccaa gcgatcgcca tggaagacgc caaaaacata    720
aagaaaggcc cggcgccatt ctatcctcta gaggatggaa ccgctggaga gcaactgcat    780
aaggctatga agagatacgc cctggttcct ggaacaattg cttttacaga tgcacatatc    840
gaggtgaaca tcacgtacgc ggaatacttc gaaatgtccg ttcggttggc agaagctatg    900
aaacgatatg ggctgaatac aaatcacaga atcgtcgtat gcagtgaaaa ctctcttcaa    960
ttctttatgc cggtgttggg cgcgttattt atcggagttg cagttgcgcc cgcgaacgac   1020
atttataatg aacgtgaatt gctcaacagt atgaacattt cgcagcctac cgtagtgttt   1080
gtttccaaaa aggggttgca aaaaattttg aacgtgcaaa aaaaattacc aataatccag   1140
aaaattatta tcatggattc taaaacggat taccagggat tcagtcgat gtacacgttc    1200
gtcacatctc atctacctcc cggttttaat gaatacgatt tgtaccaga gtcctttgat   1260
cgtgacaaaa caattgcact gataatgaat tcctctggat ctactgggtt acctaagggt    1320
gtggcccttc cgcatagaac tgcctgcgtc agattctcgc atgccagaga tcctattttt   1380
ggcaatcaaa tcattccgga tactgcgatt ttaagtgttg ttccattcca tcacggtttt   1440
ggaatgttta ctacactcgg atatttgata tgtggatttc gagtcgtctt aatgtataga   1500
tttgaagaag agctgttttt acgatcccctt caggattaca aaattcaaag tgcgttgcta   1560
gtaccaaccc tattttcatt cttcgccaaa agcactctga ttgacaaata cgatttatct   1620
aatttacacg aaattgcttc tgggggcgca cctctttcga aagaagtcgg ggaagcggtt   1680
gcaaaacgct tccatcttcc agggatacga caaggatatg ggctcactga gactacatca   1740
gctattctga ttacacccga gggggatgat aaaccgggcg cggtcggtaa agttgttcca   1800
ttttttgaag cgaaggttgt ggatctggat accgggaaaa cgctgggcgt taatcagaga   1860
ggcgaattat gtgtcagagg acctatgatt atgtccggtt atgtaaacaa tccggaagcg   1920
accaacgcct tgattgacaa ggatggatgg ctacattctg gagacatagc ttactgggac   1980
gaagacgaac acttcttcat agttgaccgc ttgaagtctt taattaaata caaaggatat   2040
caggtggccc ccgctgaatt ggaatcgata ttgttacaac accccaacat cttcgacgcg   2100
ggcgtggcag gtcttcccga cgatgacgcc ggtgaacttc cgccgccgt tgttgttttg    2160
gagcacggaa agacgatgac ggaaaaagag atcgtggatt acgtcgccag tcaagtaaca   2220
accgcgaaaa agttgcgcgg aggagttgtg tttgtggacg aagtaccgaa aggtcttacc   2280
ggaaaactcg acgcaagaaa aatcagagag atcctcataa aggccaagaa gggcggaaag   2340
tccaaattgg ttta                                                    2354
```

<210> SEQ ID NO 14
<211> LENGTH: 534
<212> TYPE: PRT
<213> ORGANISM: Artificial Sequence
<220> FEATURE:
<223> OTHER INFORMATION: a synthetic peptide

<400> SEQUENCE: 14

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Gly Gly Gly Gly
    210                 215                 220

Glu Asn Leu Tyr Phe Gln Cys Ile Ala Met Ile Glu Gly Arg Ala Met
225                 230                 235                 240

Gly Ser Glu Ile Gly Thr Gly Phe Pro Phe Asp Pro His Tyr Val Glu
                245                 250                 255

Val Leu Gly Glu Arg Met His Tyr Val Asp Val Gly Pro Arg Asp Gly
            260                 265                 270

Thr Pro Val Leu Phe Leu His Gly Asn Pro Thr Ser Ser Tyr Leu Trp
        275                 280                 285

Arg Asn Ile Ile Pro His Val Ala Pro Ser His Arg Cys Ile Ala Pro
290                 295                 300

Asp Leu Ile Gly Met Gly Lys Ser Asp Lys Pro Asp Leu Asp Tyr Phe
305                 310                 315                 320

Phe Asp Asp His Val Arg Tyr Leu Asp Ala Phe Ile Glu Ala Leu Gly
                325                 330                 335

Leu Glu Glu Val Val Leu Val Ile His Asp Trp Gly Ser Ala Leu Gly
            340                 345                 350

Phe His Trp Ala Lys Arg Asn Pro Glu Arg Val Lys Gly Ile Ala Cys
        355                 360                 365

Met Glu Phe Ile Arg Pro Ile Pro Thr Trp Asp Glu Trp Pro Glu Phe
    370                 375                 380

Ala Arg Glu Thr Phe Gln Ala Phe Arg Thr Ala Asp Val Gly Arg Glu
385                 390                 395                 400
```

```
Leu Ile Ile Asp Gln Asn Ala Phe Ile Glu Gly Ala Leu Pro Met Gly
                405                 410                 415

Val Val Arg Pro Leu Thr Glu Val Glu Met Asp His Tyr Arg Glu Pro
            420                 425                 430

Phe Leu Lys Pro Val Asp Arg Glu Pro Leu Trp Arg Phe Pro Asn Glu
        435                 440                 445

Leu Pro Ile Ala Gly Glu Pro Ala Asn Ile Val Ala Leu Val Glu Ala
    450                 455                 460

Tyr Met Asn Trp Leu His Gln Ser Pro Val Pro Lys Leu Leu Phe Trp
465                 470                 475                 480

Gly Thr Pro Gly Val Leu Ile Pro Pro Ala Glu Ala Ala Arg Leu Ala
                485                 490                 495

Glu Ser Leu Pro Asn Cys Lys Thr Val Asp Ile Gly Pro Gly Leu Phe
            500                 505                 510

Leu Leu Gln Glu Asp Asn Pro Asp Leu Ile Gly Ser Glu Ile Ala Arg
        515                 520                 525

Trp Leu Pro Gly Leu Val
    530
```

```
<210> SEQ ID NO 15
<211> LENGTH: 1605
<212> TYPE: DNA
<213> ORGANISM: Artificial Sequence
<220> FEATURE:
<223> OTHER INFORMATION: a synthetic oligonucleotide

<400> SEQUENCE: 15
```

| | | |
|---|---|---|
| atgtcccta tactaggtta ttggaaaatt aagggccttg tgcaacccac tcgacttctt | 60 |
| ttggaatatc ttgaagaaaa atatgaagag catttgtatg agcgcgatga aggtgataaa | 120 |
| tggcgaaaca aaaagtttga attgggtttg gagtttccca atcttcctta ttatattgat | 180 |
| ggtgatgtta aattaacaca gtctatggcc atcatacgtt atatagctga caagcacaac | 240 |
| atgttgggtg gttgtccaaa agagcgtgca gagatttcaa tgcttgaagg agcggttttg | 300 |
| gatattagat acggtgtttc gagaattgca tatagtaaag actttgaaac tctcaaagtt | 360 |
| gattttctta gcaagctacc tgaaatgctg aaaatgttcg aagatcgttt atgtcataaa | 420 |
| acatatttga atggtgatca tgtaacccat cctgacttca tgttgtatga cgctcttgat | 480 |
| gttgttttat acatggaccc aatgtgcctg atgcgttcc caaaattagt ttgtttcaaa | 540 |
| aaacgtattg aagctatccc acaaattgat aagtacttga atccagcaa gtatatagca | 600 |
| tggcctttgc agggctggca agccacgttt ggtggtggcg accatcctcc aaaatccgga | 660 |
| ggtggtggcg agaaaaacct gtacttccaa tgcatcgcta tgatagaggg tagagctatg | 720 |
| ggatccgaaa tcggtacagg cttccccttc gacccccatt atgtggaagt cctgggcgag | 780 |
| cgtatgcact acgtcgatgt tggaccgcgg gatggcacgc tgtgctgtt cctgcacggt | 840 |
| aacccgacct cgtcctacct gtggcgcaac atcatcccgc atgtagcacc gagtcatcgg | 900 |
| tgcattgctc cagacctgat cgggatggga aaatcggaca accagacct cgattatttc | 960 |
| ttcgacgacc acgtccgcta cctcgatgcc ttcatcgaag ccttgggttt ggaagaggtc | 1020 |
| gtcctggtca tccacgactg gggctcagct ctcggattcc actgggccaa gcgcaatccg | 1080 |
| gaacgggtca aggtattgc atgtatggaa ttcatccggc ctatcccgac gtgggacgaa | 1140 |
| tggccagaat tcgcccgtga gaccttccag gccttccgga ccgccgacgt cggccgagag | 1200 |
| ttgatcatcg atcagaacgc tttcatcgag ggtgcgctcc cgatggggt cgtccgtccg | 1260 |

```
cttacggagg tcgagatgga ccactatcgc gagcccttcc tcaagcctgt tgaccgagag    1320
ccactgtggc gattccccaa cgagctgccc atcgccggtg agcccgcgaa catcgtcgcg    1380
ctcgtcgagg catacatgaa ctggctgcac cagtcacctg tcccgaagtt gttgttctgg    1440
ggcacacccg gcgtactgat cccccggcc gaagccgcga gacttgccga aagcctcccc    1500
aactgcaaga cagtggacat cggcccggga ttgttcttgc tccaggaaga caacccggac    1560
cttatcggca gtgagatcgc gcgctggctc cccgggctgg tttaa                    1605
```

US 9,459,249 B2

PROTEIN LABELING WITH CYANOBENZOTHIAZOLE CONJUGATES

RELATED APPLICATIONS

This application claims priority under 35 U.S.C. §119(e) to U.S. Provisional Patent Application No. 61/040,073, filed Mar. 27, 2008, which is incorporated herein by reference.

BACKGROUND

Site-specific labeling of biomolecules with fluorophores often requires careful choice of labeling chemistry, optimization of the labeling reaction and characterization of the labeled biomolecules for labeling efficiency, site-specificity, and retention of functionality. The two most commonly used approaches for proteins are based on chemical coupling to sulfhydryl groups or primary amines, which result in different labeling patterns on different proteins as a consequence of the unique content and distributions of cysteine (Cys) and lysine residues in a given protein. The most common method for site-specific labeling of proteins with fluorophores is Cys-specific labeling with thiol-reactive reagents. During this reaction, proteins with surface-exposed Cys residues are covalently modified by maleimide, iodoacetamide, or other reactive conjugates of fluorophores (Waggoner, Methods Enzymol., 246:362 (1995); Haugland, Handbook of Fluorescent Probes and Research Products, 8th ed., 2002; Selvin, Methods Enzymol., 246:300 (1995)). This is a method of choice for small proteins (<about 200 residues) because cysteine is a rare amino acid and can be substituted easily with other amino acids using site-directed mutagenesis (Kunkel et al., Methods Enzymol., 205:125 (1991)).

If a protein of interest has no Cys residues, the site of incorporation of the label is selected after inspection of a high-resolution three-dimensional structure (generated using x-ray crystallography or nuclear magnetic resonance). Labeling should not perturb the enzymatic activity or the spatial arrangement of the protein sequence (also known as the "protein fold"). Subsequently, an existing amino acid (preferably having a side chain of charge, size, and hydrophobicity similar to that of Cys) at the site of choice is substituted by a Cys using site-directed mutagenesis (Kunkel et al., 1991).

If an unmodified protein has a single preexisting Cys, structural information, along with measurements of the surface accessibility of Cys side chain (Kapanidis et al., J. Mol. Biol., 312:453 (2001)), may determine whether the existing Cys can be used for labeling; otherwise, the preexisting Cys can be converted to the structurally similar amino acid serine, and the procedure for Cys-free proteins can be followed.

In a recently developed approach referred to as expressed protein ligation (EPL) (Muir, Annu. Rev. Biochem., 72:249 (2003)), proteins are expressed in C-terminal fusion with an intein domain and an affinity tag. The resulting fusion proteins can be separated from the proteins of the expression host on an affinity matrix. Treatment of the immobilized protein with a high concentration of thiol leads to the cleavage of the peptide bond between intein and target protein. The cleaved protein carries a thioester group on the C-terminus that can be coupled to a peptide (or, in fact, any molecule) bearing a Cys at its N-terminus by native chemical ligation to generate a native peptide bond at the coupling site (Dawson et al., Science, 266:776 (1994)). Although this approach was successfully used for protein engineering, its shortcomings are related to the necessity of expressing a large fusion protein that may influence the solubility and folding of the target protein and the different efficiencies of intein splicing due to the influence of the flanking residues of the target protein (Zhang et al., Gene, 275:241 (2001)).

An alternative strategy is where a thioester-conjugated functionality such as a fluorophore is coupled onto the N-terminal Cys of a recombinant protein (Schuler et al., Bioconjugate Chem., 13:1039 (2002)). In some cases, Cys on position 2 becomes N-terminal upon methionine cleavage by aminopeptidase of the expression host, although the efficiency varies among proteins (Gentle et al., Bioconjugate Chem., 15:658 (2004)). In another strategy, an N-terminal Cys is created by self-cleavage of an intein domain fused N-terminally to the target protein. Alternatively, the N-terminal Cys residue can be generated by proteolytic cleavage of a properly engineered protease cleavage site. Among proteases that were shown to tolerate Cys at the +1 position of the cleavage site are factor X, Precision protease, and TEV proteases (Cotton et al., Chem. Biol., 7:253 (2000); Tolbert et al., Angew. Chem. Int. Ed., 41:2171 (2002)).

Accordingly, there is a need for compounds, compositions, and methods to aid in site-specifically linking chemical groups onto specific sites of proteins or peptides.

SUMMARY OF THE INVENTION

The invention provides cyanobenzothiazoles linked to fluorophores or other detectable groups, e.g., reporter moieties, affinity moieties, antigens, quencher compounds, photo-crosslinking moieties, or solid supports, that may aid in the identification, quantification and/or purification of biomolecules, such as proteins. For instance, such cyanobenzothiazole derivatives are capable of rapid and specific reaction with proteins containing a cysteine ("Cys") residue at the N-terminus. By reacting with proteins having an N-terminal Cys residue, the cyanobenzothiazole derivatives can introduce a reporter moiety or other functionality at the N-terminus of a protein. In one embodiment, the reaction can proceed by nucleophilic attack of the Cys thiol on the cyano group of the cyanobenzothiazole derivative, followed by concomitant cyclization.

Cyclization provides a stable thiazoline ring, thereby covalently attaching the benzothiazole derivative to the N-terminus of a protein of interest. The derivative can include at least one reporter or affinity moiety covalently linked, for example to the 6' position, of a cyanobenzothiazole. The addition of cyanobenzothiazole derivatives to internal Cys side chains may be readily eliminated. Elimination may be achieved by addition of a Cys solution and incubation, typically for about 1 to about 10 minutes, often about 2 to about 5 minutes.

The invention also provides methods of introducing a reporter moiety or other functionality at the N-terminus of a protein of interest using a cyanobenzothiazole derivative of the invention, thereby providing a labeled protein. The Cys containing protein may be a protein having or engineered to have a Cys at position 2, may be prepared by intein-mediated methods, or prepared with an appropriate protease. In one embodiment, the derivative has the following general structure X-L-M, where X is a reporter moiety or an affinity moiety, L is an optional linker, and M is a cyanobenzothiazole. In one embodiment, L is photocleavable. In one embodiment, L is a recognition site for an enzyme. In one embodiment, L is not photocleavable. In one embodiment, L is not a recognition site for an enzyme. In one embodiment, X-L-M is not detectable but the product of a reaction between X-L-M and a N-terminal Cys containing protein is detectable. In one embodiment, X-L-M is detectable but the product of a reaction between X-L-M and a N-terminal Cys containing protein is not detectable. In another embodiment, X-L-M and the product of a reaction between X-L-M and a N-terminal Cys containing protein may be distinguished, e.g., optically.

Application of the methods include but are not limited to site-specific labeling of proteins for detection or for analysis of protein structure and function. The invention also provides methods for performing an assay to detect molecules such as enzymes of interest using derivatives of 2-cyanobenzothiazole. Enzymes of interest include but are not limited to kinases, phosphatases, peroxidases, sulfatases, peptidases, glycosidases and proteases, for example, proteases involved in apoptosis. The invention further provides novel compounds and compositions that can be used in such an assay.

The invention thus provides, according to certain embodiments, an in vitro method to N-terminally label proteins. The method includes contacting a mixture, for instance, a protein extract (lysate), purified protein, or components of a protein synthesis system, which mixture includes at least one protein with a terminal Cys, for example, an N-terminal Cys, with a derivative of cyanobenzothiazole, which includes at least one reporter moiety or affinity moiety. The cyanobenzothiazole derivative can include at least one reporter or affinity moiety attached to the benzo moiety of the cyanobenzothiazole. For example, a reporter or affinity moiety can be attached to the 4', 5', 6', or 7' position of a cyanobenzothiazole. In certain embodiments, the reporter or affinity moiety is attached the 6' position of a cyanobenzothiazole.

In one embodiment, the mixture that contains the terminal Cys protein is a cellular lysate, for instance, a cellular lysate from a commercial library. In one embodiment, the mixture may include at least one nucleic acid molecule, e.g., an mRNA, as well as tRNAs, amino acids and/or charged tRNAs, ribosomes, one or more initiation factors, one or more elongation factors, and one or more termination factors, e.g., a protein synthesis system. The mixture may also be a combined eukaryotic transcription/translation mixture.

The cyanobenzothiazole derivatives may be employed with any in vitro translation system, e.g., eukaryotic translation systems including, but not limited, to wheat germ extract, an insect cell lysate, a rabbit reticulocyte lysate, prokaryotic (e.g., S30) E. coli, a frog oocyte lysate, a dog pancreatic lysate, a human cell lysate, or mixtures of purified or semi-purified eukaryotic translation factors. In one embodiment, proteins having a reporter or affinity moiety at their N-terminus are then detected, isolated and/or quantitated.

One embodiment provides a method to specifically attach a chemical group of choice (e.g., a fluorophore or other detectable group) to the C-terminal end of a protein, peptide, or other carboxyl-containing molecule. The methods include contacting a mixture having the molecule to be labeled with a benzothiazole derivative, for example, a compound of formula I. Less stable derivatives can optionally be removed with a chase reagent, thereby yielding a mixture having a molecule with a stable detectable group.

Benzothiazole compounds of the invention include compounds of formula I:

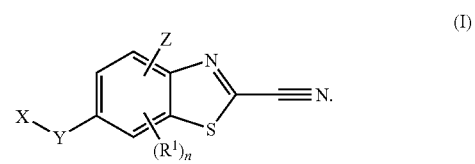

(I)

The variable Z can be H, F, Cl, Br, I, CN, amino, alkylamino, dialkylamino, alkyl ester (e.g., —CO$_2$(alkyl)), carboxy, carboxylic acid salt, alkyl amide (—C(=O)NH (alkyl)), phosphate (—OPO(OH)$_2$), alkyl phosphonate, sulfate (—OSO$_3$H), alkyl sulfonate, nitro, or (C$_1$-C$_{10}$)alkyl optionally unsaturated and optionally substituted with amino, hydroxy, oxo (=O), nitro, thiol, or halo. The group Z can be located at the 4', 5', or 7' position of the cyanobenzothiazole. In certain embodiments, Z is located at the 7' position.

Each R$^1$ can independently be H, F, Cl, Br, I, CN, (C$_1$-C$_6$)alkyl, (C$_1$-C$_6$)alkoxy, or (C$_1$-C$_6$)alkylthio, wherein each alkyl, alkoxy, or alkylthio is optionally substituted with F, Cl, Br, I, amino, alkenyl, alkynyl, cycloalkyl, aryl, alkyl sulfonate, or CO$_2$M wherein M is H, an organic cation, or an inorganic cation; wherein n is 0, 1, or 2. The group or groups R$^1$ can be located at the 4', 5', or 7' position of the cyanobenzothiazole. In certain embodiments, Z can be located at the 7' position.

The group Y can be a linking group comprising (C$_1$-C$_{16}$) alkyl optionally substituted with one or more (e.g., 1, 2, 3, 4, 1-5, or 1-6) halo, hydroxy, oxo, (C$_1$-C$_6$)alkyl, or (C$_1$-C$_6$) alkoxy, and optionally interrupted with one or more (e.g., 1, 2, 3, 4, 1-5, or 1-6) N(R'), O, S, or —N—C(=O)— groups, or Y can be absent. The term "optionally interrupted" means that one or more, e.g., 1, 2, 3, 4, 1-5, or 1-6, carbon atoms of the linking group, including one or both terminal carbons of the linking group, can be replaced with an O, N(R$^1$), S, or —N—C(=O)— group. In some embodiments, Y can optionally be absent, for example, when X is azido (N$_3$). For example, in some embodiments, Y can be —(C$_1$-C$_6$)alkyl-, —O—(C$_1$-C$_6$)alkyl-, —O—(C$_1$-C$_6$)alkyl-O—, —O—(C$_1$-C$_6$)alkyl-NH—, —O—(C$_1$-C$_6$)alkyl-(CO)NH—, —NH—(C$_1$-C$_6$)alkyl-NH—, —NH—(CO)(C$_1$-C$_6$)alkyl-NH—, —NH—(CO)(C$_1$-C$_6$)alkyl-(CO)—NH—, or —O—(C$_1$-C$_6$) alkyl-(CO)NH—(C$_1$-C$_6$)alkyl-.

The group X can be a reporter moiety, an affinity moiety, a quencher, a photocrosslinking moiety, a solid support, N$_3$, H, or OH. In certain embodiments, when X is H or OH, the compound of formula I comprises a radioactive moiety or an isotopic variant of any atom other than the carbon or nitrogen atom of the 2-nitrile moiety, for example, when Y is absent.

The functionality attached to the cyanobenzothiazole may be any molecule (or portion thereof) that is detectable or capable of detection, or capable of isolation. Those moieties include, but are not limited to, a nucleic acid molecule, i.e., DNA or RNA, e.g., an oligonucleotide, a drug, a protein, a peptide, for instance, an epitope recognized by a ligand, a hapten, e.g., keyhole limpet hemacyanin (KLH), a carbohydrate, biotin, a resin, a substrate for an enzyme, a fluorophore, a chromophore, and the like, or a combination thereof. For example, a nucleic acid reporter moiety can be detected by hybridization, amplification, binding to a nucleic acid binding protein specific for the nucleic acid reporter, enzymatic assays (e.g., if the nucleic acid molecule is a ribozyme), or, if the nucleic acid molecule itself comprises a molecule which is detectable or capable of detection, for instance, a radiolabel or biotin, it can be detected by an assay suitable for that molecule.

A nucleic acid reporter may be useful to detect and/or isolate proteins in microarrays or ribosomal display. Immuno-PCR and immuno-detection by amplification with T7 polymerase (IDAT) are also amenable to detect a nucleic acid reporter. For instance, a nucleic acid reporter attached to a cyanobenzothiazole is employed to label N-terminal Cys containing proteins, the nucleic acid is amplified, e.g., in the presence of fluorescent nucleotides, and then the amplified nucleic acid is detected (see published U.S. application 2002/0028450 (Greene et al.)). Protein- or peptide-based reporter or affinity moieties can be detected by ligand binding, e.g., binding to an antibody specific for the protein or peptide, or biochemical, enzymatic or luminescent activity, e.g., the protein based moiety may be a transport domain, an antibody, a caspase, a luciferase or green fluorescent protein (GFP).

Affinity moieties and their corresponding ligands, for instance, maltose and maltose binding protein, biotin and avidin or streptavidin and a His tag and a metal, such as cobalt, zinc, nickel or copper, find particular use in protein detection and isolation, e.g., on a solid support such as a bead, resin, or well of a multi-well plate. A fluorescent (or bioluminescent) reporter, such as one detectable by UV and/or visible excited fluorescence detection placed on the N-terminus of a protein may be used to sense changes in a system, like phosphorylation, in real time. Moreover, a fluorescent molecule, such as a chemosensor of metal ions, e.g., a 9-carbonyl-anthracene modified glycyl-histidyl-lysine (GHK) for $Cu^{2+}$, or a pair of fluorescent molecules, e.g., fluorescein and rhodamine, may be employed to label proteins so as to form protein biosensors.

A bioluminescent or fluorescent reporter, such as BODIPY, rhodamine green, GFP, or infrared dyes, also finds use in interaction studies, e.g., using BRET, FRET, LRET or electrophoresis, e.g., capillary electrophoresis. For interaction studies, one or more specific molecules are combined with the labeled proteins (either before or after isolation) to form a mixture containing labeled proteins and one or more molecules.

The interaction of one or more labeled proteins with one or more molecules can then be detected. Thus, a derivative of cyanobenzothiazole may be used in protein synthesis or mixtures of synthesized protein to detect, isolate and quantitate such proteins, e.g., human proteins, viral proteins, bacterial proteins, and parasitic proteins, including recombinant gene products, gene fusion products, enzymes, cytokines, hormones, immunogenic proteins, carbohydrate binding proteins, lipid binding proteins, nucleic acid binding proteins, and fragments thereof.

Any protein, encoded by a naturally occurring or recombinant gene, may be labeled with a moiety using the methods of the invention. Proteins containing the moiety can then be detected and/or isolated by methods known in the art. For example, proteins can be detected and/or isolated by taking advantage of unique properties of the moiety, e.g., the specific spectral property, of the moiety, by any means including electrophoresis, gel filtration, high-pressure or fast-pressure liquid chromatography, mass spectroscopy, affinity chromatography, ion exchange chromatography, chemical extraction, magnetic bead separation, precipitation, hydrophobic interaction chromatography (HIC), or any combination thereof. The isolated proteins may be employed for structural and functional studies, for the development of diagnostic applications, for the preparation biological or pharmaceutical reagents, as a tool for the development of drugs, and for studying protein interactions or for the isolation and characterization of protein complexes.

The invention also contemplates kits. In one embodiment, the kit comprises a derivative of cyanobenzothiazole having a reporter or affinity moiety and optionally one or more reagents for the detection, identification, and/or purification of labeled proteins, for example, reagents such as beads, a resin, a column, and the like. In another embodiment, the kit comprises a derivative of cyanobenzothiazole and at least one reagent. In certain embodiments, the reagent and the derivative are in separate containing means (e.g., tubes, vials, and the like). Some kits include an immobilized derivative of cyanobenzothiazole, or reagents to immobilize the cyanobenzothiazole derivative. Such kits are useful to prepare one or more N-terminally labeled proteins that are optionally isolated from a cellular or cell-free translation system.

DETAILED DESCRIPTION OF THE INVENTION

Definitions

Figure 1:
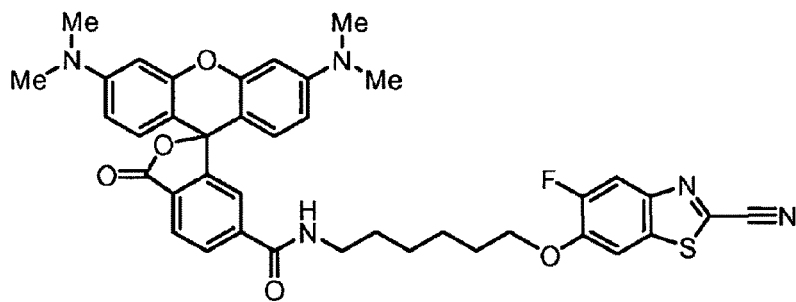
FIG. 1 illustrates certain specific compounds useful in the compositions and methods of the invention, according to various embodiments.
Figure 1:
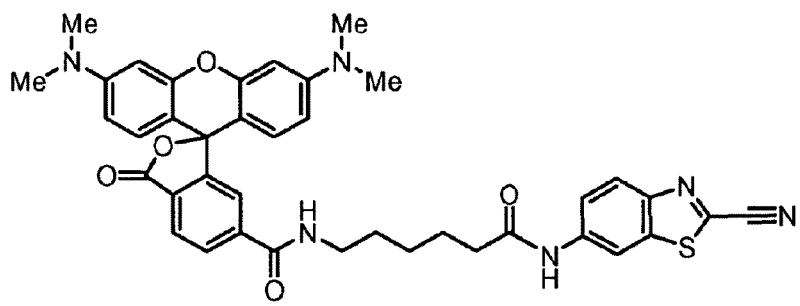
Figure 1:
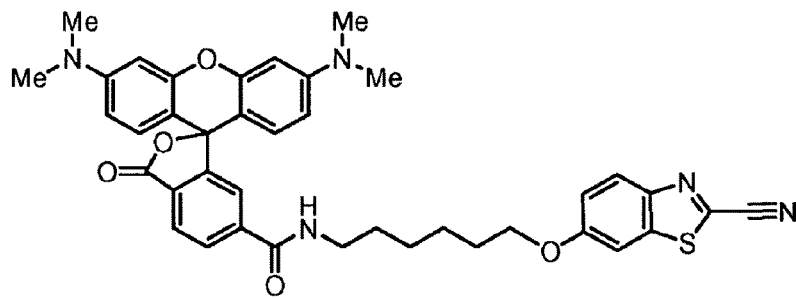
Figure 1:
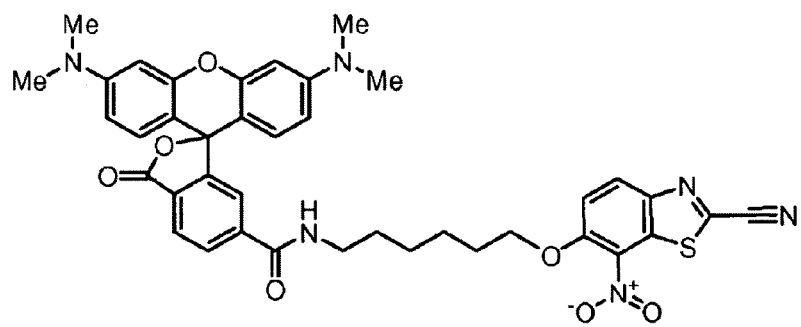
Figure 1:
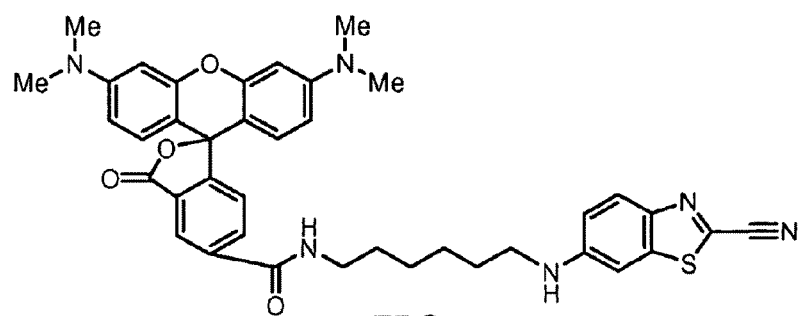

As used herein, the following terms and expressions have the indicated meanings. It will be appreciated that the compounds of the present invention contain asymmetrically substituted carbon atoms, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are part of this invention.

Specific values listed below for radicals, substituents, and ranges, are for illustration only; they do not exclude other defined values or other values within defined ranges for the radicals and substituents.

As used herein, the term "substituted" is intended to indicate that one or more (e.g., 1, 2, 3, 4, or 5; in some embodiments 1, 2, or 3; and in other embodiments 1 or 2) hydrogens on a group is replaced with one or more "substituents", e.g., one or more of a selection of suitable group known to those of skill in the art, provided that the indicated atom's normal valency is not exceeded, and that the substitution results in a stable compound. Suitable substituents include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano. Additionally, the suitable indicated groups can include, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR—S(=O)$_2$O—, —S(=O)$_2$OH, —S(=O)$_2$R, —OS(=O)$_2$OR, —S(=O)$_2$NR, —S(=O)R, —OP(=O)O$_2$RR, —P(=O)O$_2$RP(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is keto (=O) or thioxo (=S), or the like, then two hydrogen atoms on the substituted atom are replaced. In some embodiments, one or more of the preceding groups can be expressly excluded from an embodiment.

The terms "stable compound" and "stable structure" indicate a compound that is sufficiently robust to survive isolation to a useful degree of purity from a reaction mixture. Only stable compounds are claimed in the present invention, however, certain unstable compounds, for example, those that cannot easily be isolated, can be employed in the methods described herein.

One diastereomer may display superior properties or activity compared with another. When required, separation of the racemic material can be achieved by HPLC using a chiral column or by a resolution using a resolving agent such as camphonic chloride as described by Tucker et al., *J. Med. Chem.*, 37: 2437 (1994). A chiral compound may also be directly synthesized using a chiral catalyst or a chiral ligand, e.g. Huffman et al., *J. Org. Chem.*, 60:1590 (1995).

As used herein, the term "alkyl" refers to a branched, unbranched, or cyclic hydrocarbon having, for example, from 1 to 20 carbon atoms, and often 1 to about 12, 1 to about 6, or 1 to about 4 carbon atoms. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted. The alkyl can also be optionally partially or fully unsaturated. As such, the recitation of an alkyl group includes both alkenyl and alkynyl groups. The alkyl can be a monovalent hydrocarbon radical, as described and exemplified above, or it can be a divalent hydrocarbon radical (i.e., alkylene).

The term "alkenyl" refers to a monoradical branched or unbranched partially unsaturated hydrocarbon chain (i.e. a carbon-carbon, Sp2 double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

As used herein, "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have from 6 to 20 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups.

The term "halo" refers to fluoro, chloro, bromo, and iodo. Similarly, the term "halogen" refers to fluorine, chlorine, bromine, and iodine.

The term "haloalkyl" refers to alkyl as defined herein substituted by 1 or more halo groups as defined herein, which may be the same or different. In one embodiment, the haloalkyl can be substituted with 1, 2, 3, 4, or 5 halo groups. In another embodiment, the haloalkyl can by substituted with 1, 2, or 3 halo groups. The term haloalkyl also include perfluoro-alkyl groups. Representative haloalkyl groups include, by way of example, trifluoromethyl, 3-fluorododecyl, 12,12,12-trifluorododecyl, 2-bromooctyl, 3-bromo-6-chloroheptyl, 1H,1H-perfluorooctyl, and the like. The haloalkyl can be optionally substituted as described above for alkyl groups.

The term "heteroaryl" is defined herein as a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described above in the definition of "substituted". Typical heteroaryl groups contain 2-20 carbon atoms in addition to the one or more hetoeroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d] furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or $(C_1-C_6)$(alkyl) aryl. In another embodiment heteroaryl denotes an ortho-fused bicyclic heterocycle of about eight to ten ring atoms derived therefrom, particularly a benz-derivative or one derived by fusing a propylene, trimethylene, or tetramethylene diradical thereto.

The term "heterocycle" refers to a saturated or partially unsaturated ring system, containing at least one heteroatom selected from the group oxygen, nitrogen, and sulfur, and optionally substituted with one or more groups as defined herein under the term "substituted". A heterocycle can be a monocyclic, bicyclic, or tricyclic group containing one or more heteroatoms. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, indolinyl, isochromanyl, isoindolinyl, morpholine, piperazinyl, piperidine, piperidyl, pyrazolidine, pyrazolidinyl, pyrazolinyl, pyrrolidine, pyrroline, quinuclidine, and thiomorpholine.

The term "heterocycle" can include, by way of example and not limitation, a monoradical of the heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.,* 82: 5566 (1960). In one embodiment, "heterocycle" includes a "carbocycle" as defined herein, wherein one or more (e.g. 1, 2, 3, or 4) carbon atoms have been replaced with a heteroatom (e.g. O, N, or S).

Examples of heterocycles, by way of example and not limitation, include, dihydroxypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, 5-thiazolyl, and the like.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. In one embodiment, nitrogen bonded heterocycles include 1-aziridyl, 1-azetedyl, 1-pyrrolyl, 1-imidazolyl, 1-pyrazolyl, and 1-piperidinyl.

The term "carbocycle" refers to a saturated, unsaturated or aromatic ring having 3 to 8 carbon atoms as a monocycle, 7 to 12 carbon atoms as a bicycle, and up to about 30 carbon atoms as a polycycle. Monocyclic carbocycles typically have 3 to 6 ring atoms, still more typically 5 or 6 ring atoms.

Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl, spiryl and naphthyl. The carbocycle can be optionally substituted as described above for alkyl groups.

The term "alkanoyl" or "alkylcarbonyl" refers to —C(=O)R, wherein R is an alkyl group as previously defined.

The term "acyloxy" or "alkylcarboxy" refers to —O—C(=O)R, wherein R is an alkyl group as previously defined. Examples of acyloxy groups include, but are not limited to, acetoxy, propanoyloxy, butanoyloxy, and pentanoyloxy. Any alkyl group as defined above can be used to form an acyloxy group.

The term "alkoxycarbonyl" refers to —C(=O)OR (or "COOR"), wherein R is an alkyl group as previously defined.

The term "amino" refers to —NH$_2$. The amino group can be optionally substituted as defined herein for the term "substituted". The term "alkylamino" refers to —NR$_2$, wherein at least one R is alkyl and the second R is alkyl or hydrogen. The term "acylamino" refers to N(R)C(=O)R, wherein each R is independently hydrogen, alkyl, or aryl.

The term "amino acid," includes a residue of a natural amino acid (e.g. Ala, Arg, Asn, Asp, Cys, Glu, Gln, Gly, H is, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide; or as an α-methylbenzyl amide). Other suitable amino and carboxy protecting groups are known to those skilled in the art (See for example, Greene, T. W.; Wutz, P. G. M. *Protecting Groups In Organic Synthesis*, 2$^{nd}$ edition, John Wiley & Sons, Inc., New York (1991) and references cited therein).

The term "peptide" describes a sequence of 2 to 35 amino acids (e.g. as defined hereinabove) or peptidyl residues. The sequence may be linear or cyclic. For example, a cyclic peptide can be prepared or may result from the formation of disulfide bridges between two cysteine residues in a sequence. Preferably a peptide comprises 3 to 20, or 5 to 15 amino acids. Peptide derivatives can be prepared as disclosed in U.S. Pat. Nos. 4,612,302; 4,853,371; and 4,684,620, or as described in the Examples herein below. Peptide sequences specifically recited herein are written with the amino terminus on the left and the carboxy terminus on the right.

The term "saccharide" refers to a sugar or other carbohydrate, especially a simple sugar. The saccharide can be a $C_6$-polyhydroxy compound, typically $C_6$-pentahydroxy, and often a cyclic glycal. The term includes the known simple sugars and their derivatives, as well as polysaccharides with two or more monosaccharide residues. The saccharide can include protecting groups on the hydroxyl groups, as described above in the definition of amino acids. The hydroxyl groups of the saccharide can be replaced with one or more halo or amino groups. Additionally, one or more of the carbon atoms can be oxidized, for example to keto or carboxyl groups.

The term "interrupted" indicates that another group is inserted between two adjacent carbon atoms (and the hydrogen atoms to which they are attached (e.g., methyl (CH$_3$), methylene (CH$_2$) or methine (CH))) of a particular carbon chain being referred to in the expression using the term "interrupted", provided that each of the indicated atoms' normal valency is not exceeded, and that the interruption results in a stable compound. Suitable groups that can interrupt a carbon chain include, e.g., with one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) and sulfonyl (SO$_2$). Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached. In certain embodiments, one or more of the aforementioned groups are excluded from an embodiment.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds. In certain embodiments, the compounds of the invention do not include any compounds disclosed in U.S. Pat. No. 5,424,440 (Klem et al.).

Selected substituents within the compounds described herein are present to a recursive degree. In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in an claim of the invention, the total number will be determined as set forth above.

The term "linker" as used herein is an atom chain, typically a carbon chain, that covalently attaches two chemical groups together and may include a substrate for an enzyme that may be cleaved by that enzyme or another molecule, or may be photosensitive. The chain is optionally interrupted by one or more nitrogen atoms, oxygen atoms, carbonyl groups, (substituted)aromatic rings, or peptide bonds, and/or one of these groups may occur at one or both ends of the atom chain that forms the linker. Many linkers are well known in the art, and can be used to link a compound or formula described herein to another group, such as a solid support or resin. See for example, the linkers and solid supports described by Sewald and Jakubke in

*Peptides: Chemistry and Biology*, Wiley-VCH, Weinheim (2002), pages 212-223; and by Dorwald in *Organic Synthesis on Solid Phase*, Wiley-VCH, Weinheim (2002).

As used herein, a "fluorophore" includes a molecule that is capable of absorbing energy at a wavelength range and releasing energy at a wavelength range other than the absorbance range. In certain embodiments, the fluorophore is a molecule that is capable of absorbing energy at about 250 nm to about 900 nm, and can release energy at a wavelength range of about 260 nm to about 910 nm. The term "excitation wavelength" refers to the range of wavelengths at which a fluorophore absorbs energy. The term "emission wavelength" refers to the range of wavelengths that the fluorophore releases energy or fluoresces.

Fluorophores include but are not limited to fluoroscein, Texas Red, DAPI, PI, acridine orange, Alexa fluors, e.g., Alexa 350, Alexa 405 or Alexa 488, cyanine dyes such as Cy3, Cy5, and Cy7, coumarin, ethidium bromide, fluorescein, BODIPY, rhodol, Rox, 5-carboxyfluorescein, 6-carboxyfluorescein, an anthracene, 2-amino-4-methoxynaptalene, a phenalenone, an acridone, fluorinated xanthene derivatives, α-naphtol, β-napthol, 1-hydroxypyrene, coumarins, e.g., 7-amino-4-methylcoumarin (AMC) or 7-amino-4-trifluoromethylcoumarin (AFC), rhodamines, e.g., tetramethylrhodamine, rhodamine-110, carboxyrhodamine, cresyl violet, or resorufin, as well as fluorophores disclosed in U.S. Pat. No. 6,420,130 (Makings, et al.), the disclosure of which is incorporated by reference herein. Fluorophores include cyanine dyes, such as compounds of the formula Ar—[CH=CH]$_n$—[CH=]$_m$Ar, wherein Ar is an aryl or heteroaryl group; n is 1, 2, 3, or 4; m is 0 or 1; and wherein each Ar includes a quaternary nitrogen or a nitrogen capable of being quaternized through resonance. Examples of such aryl or heteroaryl groups include dimethyl-aminophenyl, imidazole, pyridine, pyrrole, quinoline, thiazole, and indole, each optionally substituted. The fluorophore can be a compound that is inherently fluorescent or demonstrates a change in fluorescence upon binding to a biological compound, i.e. it can be fluorogenic, or its intensity can be diminished by quenching. Fluorophores may contain substitutents that alter the solubility, spectral properties or physical properties of the fluorophore. Various fluorophores are known to those skilled in the art and also include, but are not limited to benzofurans, quinolines, quinazolinones, indoles, benzazoles, borapolyazaindacene, and xanthenes including fluoroscein, rhodamine, and rhodol, as well as other fluorophores described in Richard P. Haugland's *The Handbook, A Guide to Fluorescent Probes and Labeling Technologies* (10$^{th}$ edition, 2005), which describes numerous fluorophones available from Invitrogen Molecular Probes.

A "fluorogenic assay" or "fluorogenic reaction" includes a reaction in which a product of a reaction is fluorescent. A "fluorogenic assay reagent" may include a substrate, as well as a cofactor(s) or other molecule(s) such as a protein, e.g., an enzyme, for a fluorogenic reaction.

The term "solid support" refers to a support that can be isolated from a reaction mixture in solid form, such as a silicate or polymer particle. Solid supports include various particles and surfaces, such as beads, microtiter plates, eppendorf tubes, and slides. The surface can be a polymer such as sepharose, cellulose, alginate, polystyrene or other plastics, and/or other surfaces including membranes and glass. Many common solid supports are described by Sewald and Jakubke in *Peptides: Chemistry and Biology*, Wiley-VCH, Weinheim (2002), pages 212-223; and by Dorwald in *Organic Synthesis on Solid Phase*, Wiley-VCH, Weinheim (2002). The cyanobenzothiazoles can be linked to the solid support either non-specifically (via adsorption to the surface) or specifically (via capture by an antibody specific to the cyanobenzothiazole, as in a "sandwich" ELISA). A detection antibody on the surface of the solid support can be covalently linked to an enzyme, or can itself be detected by a secondary antibody linked to an enzyme through bioconjugation. For examples of ELISA "sandwich" test procedures, see Schuurs and van Weemen, *J. Immunoassay* 1980; 1:229-49.

The term "reporter moiety" refers to a portion of a molecule that can be detected in a biological or non-biological mixture (e.g. a fluorophore, chromophore, or radioactive element). The reporter moiety can be a molecule that is capable of functioning as a member of an energy transfer pair wherein the reporter molecule retains its native properties (e.g., spectral properties, conformation, and/or activity) when attached to a ligand analog and is used in the methods disclosed herein. The reporter moiety can be a reporter molecule linked to a cyanobenzothiazole. Examples of reporter molecules include but are not limited to nucleic acids, borapolyazaindacenes, coumarins, xanthenes, cyanines, and luminescent molecules, including dyes, fluorescent proteins, chromophores, and chemiluminescent compounds that are capable of producing a detectable signal upon appropriate activation. The term "dye" refers to a compound that emits light to produce an observable detectable signal. "Dye" includes phosphorescent, fluorescent, and nonfluorescent compounds that include without limitation pigments, fluorophores, chemiluminescent compounds, luminescent compounds, and chromophores. The term "chromophore" refers to a label that emits and/or reflects light in the visible spectra that can be observed without the aid of instrumentation.

The terms "affinity moiety", "affinity label", and/or "affinity molecule" refer to a portion of a molecule that can effectively bind noncovalently or covalently to a molecule, biomolecule, or material of interest (e.g. biotin, HisTag, or chitin). An affinity moiety can be a molecule containing acceptor groups. Thus, a cyanobenzothiazole derivative that includes an affinity moiety can be used to facilitate the identification and separation of labeled molecules or complexes because of the selective interaction of the affinity moiety with another molecule, e.g., a molecule that will bind to the affinity moiety, that may be biological or non-biological in origin.

The term "quencher" or "quenching moiety" refers to a molecule or portion of a molecule that is a strong photon absorber, is non-fluorescent or is essentially non-fluorescent, and effectively quenches fluorescence of other molecules in its vicinity. The quenching moiety can be a moiety that is capable of absorbing energy from an energy donor that is not re-emitted (non-fluorescent), or is re-emitted at a detectably different wavelength from the energy emitted by the donor molecule. In this respect, in certain embodiments quenchers may be essentially non-fluorescent or fluorescent. Some examples of quencher moieties that can be linked to a cyanobenzothiazole include xanthene, xanthene derivatives, cyanine, cyanine derivatives, dimethylaminoazosulfonic acid (DABSYL), and dimethylaminoazo-carboxylic acid (DABCYL). Numerous quenching moieties are well known in the art including xanthenes, cyanines, and other compounds disclosed in Richard P. Haugland's *The Handbook, A Guide to Fluorescent Probes and Labeling Technologies* (10$^{th}$ edition, 2005). Quenchers and quenching of fluorescence is further described by J. Lakowicz in *Principles of Fluorescence Spectroscopy*, 2$^{nd}$ Ed., New York: Kluwer Academic/Plenum (1999); see in particular, Chapter 8 ("Quenching of Fluorescence"), pages 237-264; and the 3$^{rd}$ Ed., New York: Springer Science (2006), Chapter 8, pages 278-327, and references cited therein. In certain embodiments, a quencher can be a chromophoric molecule or part of a compound, capable of reducing the emission from a fluorescent donor when attached to the donor. Quenching may occur by any of several mechanisms including fluorescence resonance energy transfer, photoinduced electron transfer, paramagnetic enhancement of intersystem crossing, Dexter exchange coupling, and exciton coupling such as the formation of dark complexes.

The term "acceptor" refers to a quencher that operates via energy transfer. Acceptors may re-emit the transferred energy as fluorescence and are "acceptor fluorescent moieties". Examples of acceptors include coumarins and related fluorophores, xanthenes such as fluoresceins, rhodols, and rhodamines, resorufins, cyanines, difluoroboradiazaindacenes, and phthalocyanines. Other chemical classes of acceptors generally do not re-emit the transferred energy as light. Examples include some indigos, benzoquinones, anthraquinones, azo compounds, nitro compounds, indoanilines, and di- and triphenylmethanes.

The term "photocrosslinking moiety" refers to a portion of a molecule which upon photoexcitation can covalently bond to another molecule, biomolecule, or material of interest. For example, a compound that includes a photocrosslinking moiety can be used to crosslink a protein upon photoexcitation.

The term "enzyme of interest" refers to any enzyme that can be labeled using the methods of the invention or other methods known in the art. Enzymes of interest include, for example, kinases, phosphatases, peroxidases, sulfatases, peptidases, glycosidases, proteases, for example, proteases involved in apoptosis, hydrolases, oxidoreductases, lyases, transferases, isomerases, ligases, protein kinases, protein phosphatases, esterases, isomerases, glycosylases, synthetases, dehydrogenases, oxidases, reductases, methylases and the like. Further enzymes of interest include those involved in making or hydrolyzing esters, both organic and inorganic, glycosylating, and hydrolyzing amide bonds. In any class, there may be further subdivisions, as in the kinases, where the kinase may be specific for phosphorylation of serine, threonine and/or tyrosine residues in peptides and proteins.

Other enzymes of interest include any protein that exhibits enzymatic activity, e.g., lipases, phospholipases, sulphatases, ureases, peptidases, proteases and esterases, including acid phosphatases, glucosidases, glucuronidases, galactosidases, carboxylesterases, and luciferases. In one embodiment, the enzyme is a hydrolytic enzyme. Examples of hydrolytic enzymes include alkaline and acid phosphatases, esterases, decarboxylases, phospholipase D, P-xylosidase, β-D-fucosidase, thioglucosidase, β-D-galactosidase, α-D-galactosidase, α-D-glucosidase, β-D-glucosidase, β-D-glucuronidase, α-D-mannosidase, β-D-mannosidase, β-D-fructofuranosidase, and β-D-glucosiduronase.

Further enzymes of interest are hydrolases, including but are not limited to, enzymes acting on ester bonds such as carboxylic ester hydrolases, thiolester hydrolases, phosphoric monoester hydrolases, phosphoric diester hydrolases, triphosphoric monoester hydrolases, sulfuric ester hydrolases, diphosphoric monoester hydrolases, phosphoric triester hydrolases, exodeoxyribonucleases producing 5'-phosphomonoesters, exoribonucleases producing 5'-phosphomonoesters, exoribonucleases producing 3'-phosphomonoesters, exonucleases active with either ribo- or deoxyribonucleic acid, exonucleases active with either ribo- or deoxyribonucleic acid, endodeoxyribonucleases producing 5'-phosphomonoesters, endodeoxyribonucleases producing other than 5'-phosphomonoesters, site-specific endodeoxyribonucleases specific for altered bases, endoribonucleases producing 5'-phosphomonoesters, endoribonucleases producing other than 5'-phosphomonoesters, endoribonucleases active with either ribo- or deoxyribonucleic, endoribonucleases active with either ribo- or deoxyribonucleic glycosylases; glycosidases, e.g., enzymes hydrolyzing O- and S-glycosyl compounds, and those hydrolyzing N-glycosyl compounds; acting on ether bonds such as trialkylsulfonium hydrolases or ether hydrolases; enzymes acting on peptide bonds (peptide hydrolases) such as aminopeptidases, dipeptidases, dipeptidyl-peptidases and tripeptidyl-peptidases, peptidyl-dipeptidases, serine-type carboxypeptidases, metallocarboxypeptidases, cysteine-type carboxypeptidases, omega peptidases, serine endopeptidases, cysteine endopeptidases, aspartic endopeptidases, metalloendopeptidases, threonine endopeptidases, and endopeptidases of unknown catalytic mechanism; enzymes acting on carbon-nitrogen bonds, other than peptide bonds, such as those in linear amides, in cyclic amides, in linear amidines, in cyclic amidines, in nitriles, or other compounds; enzymes acting on acid anhydrides such as those in phosphorous-containing anhydrides and in sulfonyl-containing anhydrides; enzymes acting on acid anhydrides (catalyzing transmembrane movement); enzymes acting on acid anhydrides or involved in cellular and subcellular movement; enzymes acting on carbon-carbon bonds (e.g., in ketonic substances); enzymes acting on halide bonds (e.g., in C-halide compounds), enzymes acting on phosphorus-nitrogen bonds; enzymes acting on sulfur-nitrogen bonds; enzymes acting on carbon-phosphorus bonds; and enzymes acting on sulfur-sulfur bonds.

The term "poly-histidine tract" or "His tag" refers to a molecule comprising two to ten histidine residues, e.g., a poly-histidine tract of five to ten residues. A poly-histidine tract allows the affinity purification of a covalently linked molecule on an immobilized metal (e.g., nickel, zinc, cobalt or copper) chelate column or through an interaction with another molecule (e.g., an antibody reactive with the His tag).

Linkers

A linker strategy may be employed to link a reporter moiety, e.g., a fluorophore, an affinity moiety, or another labeling group such as a biotin, a resin, a carbohydrate, an oligopeptide, a dye, or a drug moiety, to a cyanobenzothiazole, yielding a cyanobenzothiazole derivative capable of reacting with a protein that has an N-terminal cysteine. The use of linkers or "linking groups" is well known in the art.

A linking group can be an alkyl or alkoxy chain, such as a ($C_1$-$C_6$)alkyl or a ($C_1$-$C_6$)alkoxy group. The chain can have one or more electron withdrawing group substituents R, such as an aldehyde, acetyl, sulfoxide, sulfone, nitro, cyano group, or a combination thereof. Certain linkers and methods for preparing covalent linkages are described in, for example, U.S. Pat. No. 7,282,339 (Beechem et al.); in *Peptides: Chemistry and Biology* by Sewald and Jakubke, Wiley-VCH, Weinheim (2002), pages 212-223; and in *Organic Synthesis on Solid Phase* by Dorwald, Wiley-VCH, Weinheim (2002); which are incorporated herein by reference.

In certain embodiments, the linking group can be a divalent radical of the formula W-A wherein A is ($C_1$-$C_6$) alkyl, ($C_2$-$C_6$)alkenyl, ($C_2$-$C_6$)alkynyl, ($C_3$-$C_8$)cycloalkyl, or $(C_6-C_{10})$aryl; W is —N(R)C(=O)—, —C(=O)N(R)—, —OC(=O)—, —C(=O)O—, —O—, —S—, —S(O)—, —S(O)$_2$—, —N(R)—, —C(=O)—, or a direct bond; each R is independently H,$(C_1-C_6)$alkyl, or a protecting group; and the linker group links together two other molecular moieties, for example, a cyanobenzothiazole moiety and a group X as defined above, such as a reporter moiety.

Immobilization

The invention includes immobilized derivatives of cyanobenzothiazole and methods to immobilize the cyanobenzothiazole derivative. Some immobilized cyanobenzothiazoles include those that are linked to solid supports at a position on the benzo ring, for example, at the 6'-position. Other immobilized cyanobenzothiazoles include those that are bound to the surface of a solid support by bioactive groups (e.g., biotin, avidin, streptavidin, or derivatives thereof), non-covalent binding interactions such as by antibodies, or antigens, or His-tag to a nickel column. Still other immobilized cyanobenzothiazole can be prepared by reacting the cyanobenzothiazole with a terminal Cys-containing protein of interest followed by binding with a solid support that has an appropriate antibody on the solid support surface that will bind the protein of interest.

Labeling Methods

The present invention comprises methods for the labeling of proteins and detection and/or isolation of labeled proteins from a cellular or cell-free translation system. The isolated protein may be used directly or further purified and/or manipulated. In one embodiment, the methods may be employed with defined proteins, e.g., a population of defined proteins, or employed with a set of proteins which include one or more undefined proteins, such as those obtained from cells or an expression library.

The one or more proteins may be from a sample that includes eukaryotic cells, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof.

The methods disclosed herein comprise labeling proteins with Cys at their N-terminus with any detectable molecule or a molecule that is capable of being detected. The Cys may be added to the protein via recombinant techniques, e.g., exposing a Cys such as one in a fusion protein by intein-mediated splicing or insertion of an appropriate protease site, the Cys may be naturally occurring at position 2 in a protein susceptible to an N-terminal aminopeptidase, or may be added by synthesis various synthesis techniques, e.g., via peptide ligation, or reverse proteolysis (see for example, Wehofsky, *J. Amer. Chem. Soc.* 125:6126 (2003) and Chang, *P.N.A.S.* 91:12,544 (1994)). For example, a preparation of proteins at least one of which has a N-terminal Cys is reacted with a derivative of cyanobenzothiazole having a fluorophore to form at least one protein that comprises the fluorophore covalently linked to its N-terminus. A linker group may be employed to facilitate linking the reporter or affinity moiety to the cyanobenzothiazole.

A. Exemplary Moieties for Labeling

Labels include molecules (moieties) that are detectable or capable of detection and, in one embodiment, moieties useful in the compounds and methods described herein are molecules that are capable of being covalently linked to the amino group of Cys via a derivative of cyanobenzothiazole. Moieties useful in the compounds and methods have one or more properties that facilitate detection and optionally the quantification and/or isolation of proteins comprising the moiety. One physical property is a characteristic electromagnetic spectral property such as emission or absorbance, magnetism, electron spin resonance, electrical capacitance, dielectric constant or electrical conductivity. In certain embodiments, the moieties may be ferromagnetic, paramagnetic, diamagnetic, luminescent, electrochemi-luminescent, fluorescent, phosphorescent, chromatic, antigenic or have a distinctive mass.

Relevant moieties include, but are not limited to, a nucleic acid molecule, i.e., DNA or RNA, e.g., an oligonucleotide or nucleotide, such as one having nucleotide analogs, DNA which is capable of binding a protein, single or double stranded DNA corresponding to a gene of interest, RNA corresponding to a gene of interest, mRNA which lacks a stop codon, an aminoacylated initiator tRNA, an aminoacylated amber suppressor tRNA, or double stranded RNA for RNAi, a protein, e.g., a luminescent protein, a peptide, a peptide nucleic acid, an epitope recognized by a ligand, e.g., biotin or streptavidin, a hapten, an amino acid, a lipid, a lipid bilayer, a solid support, a fluorophore, a chromophore, a reporter molecule, a radionuclide, such as a radioisotope for use in, for instance, radioactive measurements or a stable isotope, an electron opaque molecule, an X-ray contrast reagent, a MRI or X ray contrast agent, e.g., barium, iodine, manganese, gadolinium (III) or iron-oxide particles, and the like.

In one embodiment, the moiety is a glycoprotein, polysaccharide, triplet sensitizer, e.g., CALI, drug, toxin, lipid, biotin, or solid support, such as self-assembled monolayers, is electron opaque, is a chromophore, a nanoparticle, an enzyme, a substrate for an enzyme, an inhibitor of an enzyme, for instance, a suicide substrate, a cofactor, e.g., NADP, a coenzyme, a succinimidyl ester or aldehyde, glutathione, NTA, biotin, cAMP, phosphatidylinositol, a ligand for cAMP, a metal, a nitroxide or nitrone for use as a spin trap (detected by electron spin resonance (ESR), a metal chelator, e.g., for use as a contrast agent, in time resolved fluorescence or to capture metals, a photocaged compound, e.g., where irradiation liberates the caged compound such as a fluorophore, an intercalator, e.g., such as psoralen or another intercalator useful to bind DNA or as a photoactivatable molecule, a triphosphate or a phosphoramidite, e.g., to allow for incorporation of the substrate into DNA or RNA, an antibody, a heterobifunctional cross-linker such as one useful to conjugate proteins or other molecules, cross-linkers including but not limited to hydrazide, aryl azide, maleimide, iodoacetamide/bromoacetamide, N-hydroxysuccinimidyl ester, mixed disulfide such as pyridyl disulfide, glyoxal/phenylglyoxal, vinyl sulfone/vinyl sulfonamide, acrylamide, boronic ester, hydroxamic acid, imidate ester, isocyanate/isothiocyanate, or chlorotriazine/dichlorotriazine, a glycoprotein, a polysaccharide, lipids including lipid bilayers; or is a solid support, e.g., a sepharose or cellulose bead, a membrane, glass, e.g., glass slides, cellulose, alginate, plastic or other synthetically prepared polymer, e.g., an eppendorf tube or a well of a multi-well plate, self assembled monolayers, a surface plasmon resonance chip, or a solid support with an electron conducting surface, and includes a drug, an aminoacylated tRNA such as an aminoacylated initiator tRNA or an aminoacylated amber suppressor tRNA, a molecule that binds $Ca^{2+}$, a molecule that binds $K^+$, a molecule that binds $Na^+$, a molecule that is pH sensitive, a radionuclide, a molecule that is electron opaque, a molecule that fluoresces in the presence of NO or is sensitive to a reactive oxygen, a nonprotein substrate for an enzyme, an inhibitor of an enzyme, either a reversible or irreversible inhibitor, a chelating agent, a cross-linking group, for example, a succinimidyl ester or aldehyde, glutathione, biotin or other avidin binding molecule, avidin, streptavidin, phosphatidylinositol, heme, a ligand for cAMP, a metal, NTA, and, in one embodiment, includes one or more dyes, e.g., a xanthene dye, a calcium sensitive dye, e.g., 1-[2-amino-5-(2,7-dichloro-6-hydroxy-3-oxy-9-xanthenyl)-phenoxy]-2-(2'-amino-5'-methylphenoxy)ethane-N,N,N',N'-tetraacetic acid (Fluo-3), a sodium sensitive dye, e.g., 1,3-benzenedicarboxylic acid, 4,4'-[1,4,10,13-tetraoxa-7,16-diazacyclooctadecane-7,16-diylbis(5-methoxy-6,2-benzofurandiyl)]bis(PBFI), a NO sensitive dye, e.g., 4-amino-5-methylamino-2',7'-difluorescein, or other fluorophore. In one embodiment, the moiety is not a radionuclide. In another embodiment, the moiety is a radionuclide, e.g., $^3$H, $^{14}$C, $^{35}$S, $^{125}$I, $^{131}$I, including a molecule useful in diagnostic methods.

Exemplary moieties include haptens, e.g., molecules useful to enhance immunogenicity such as keyhole limpet hemacyanin (KLH), cleavable moieties, for instance, photocleavable biotin, and fluorescent moieties, e.g., N-hydroxy-succinimide (NHS) modified coumarin and succinimide or sulfonosuccinimide modified BODIPY (which can be detected by UV and/or visible excited fluorescence detection), rhodamine, e.g., R110, rhodols, CRG6, Texas Methyl Red (carboxytetramethylrhodamine), 5-carboxy-X-rhodamine, or fluoroscein, coumarin derivatives, e.g., 7-aminocoumarin, and 7-hydroxycoumarin, 2-amino-4-methoxynapthalene, 1-hydroxypyrene, resorufin, phenalenones or benzphenalenones (U.S. Pat. No. 4,812,409), acridinones (U.S. Pat. No. 4,810,636), anthracenes, and derivatives of α- and β-napthol, fluorinated xanthene derivatives including fluorinated fluoresceins and rhodols (e.g., U.S. Pat. No. 6,162,931), bioluminescent molecules, e.g., luciferin, coelenterazine, luciferase, chemiluminescent molecules, e.g., stabilized dioxetanes, and electrochemi-luminescent molecules.

Examples of affinity moieties include molecules such as immunogenic molecules, e.g., epitopes of proteins, peptides, carbohydrates or lipids, i.e., any molecule which is useful to prepare antibodies specific for that molecule; biotin, avidin, streptavidin, and derivatives thereof; metal binding molecules; and fragments and combinations of these molecules. Exemplary affinity molecules include His5 (HHHHH) (SEQ ID NO:1), H is X6 (HHHHHH) (SEQ ID NO:2), C-myc (EQKLISEEDL) (SEQ ID NO:3), Flag (DYKDDDDK) (SEQ ID NO:4), SteptTag (WSHPQFEK) (SEQ ID NO:5), HA Tag (YPYDVPDYA) (SEQ ID NO:6), thioredoxin, cellulose binding domain, chitin binding domain, S-peptide, T7 peptide, calmodulin binding peptide, C-end RNA tag, metal binding domains, metal binding reactive groups, amino acid reactive groups, inteins, biotin, streptavidin, and maltose binding protein.

For example, the presence of the biotin at the N-terminus of proteins permits selective binding of those proteins to avidin molecules, e.g., avidin molecules coated onto a surface, e.g., beads, microwells, nitrocellulose and the like. Suitable surfaces include resins for chromatographic separation, plastics such as tissue culture surfaces for binding plates, microtiter dishes and beads, ceramics and glasses, particles including magnetic particles, polymers and other matrices. The treated surface is washed with, for example, phosphate buffered saline (PBS), to remove non-nascent proteins and other translation reagents and the nascent proteins isolated. In some case these materials may be part of biomolecular sensing devices such as optical fibers, chemfets, and plasmon detectors.

Another example of an affinity molecule is dansyllysine. Antibodies that interact with the dansyl ring system are commercially available (Sigma Chemical; St. Louis, Mo.) or can be prepared using known protocols such as those described in *Antibodies: A Laboratory Manual* (Harlow and Lane, 1988). For example, the anti-dansyl antibody is immobilized onto the packing material of a chromatographic column. This method, affinity column chromatography, accomplishes separation by causing the complex between an immobilized antibody and a substrate to be retained on the column (for example, a benzothiazole derivative linked to an affinity moiety) due to its interaction with the immobilized antibody, while other molecules pass through the column. The complex may then be released by disrupting the antibody-antigen interaction. Specific chromatographic column materials such as ion-exchange or affinity Sepharose, Sephacryl, Sephadex and other chromatography resins are commercially available (Sigma Chemical; St. Louis, Mo.; Pharmacia Biotech; Piscataway, N.J.). Dansyllysine may conveniently be detected because of its fluorescent properties.

When employing an antibody as an acceptor molecule, separation can also be performed through other biochemical separation methods such as immunoprecipitation and immobilization of antibodies on filters or other surfaces such as beads, plates or resins. Beads are oftentimes separated from the mixture using magnetic fields.

Another class of moieties includes molecules detectable using electromagnetic radiation and includes but is not limited to xanthene fluorophores, dansyl fluorophores, coumarins and coumarin derivatives, fluorescent acridinium moieties, benzopyrene based fluorophores, as well as 7-nitrobenz-2-oxa-1,3-diazole, and 3-N-(7-nitrobenz-2-oxa-1,3-diazol-4-yl)-2,3-diamino-propionic acid. Preferably, the fluorescent molecule has a high quantum yield of fluorescence at a wavelength different from native amino acids and more preferably has high quantum yield of fluorescence that can be excited in the visible, or in both the UV and visible, portion of the spectrum. Upon excitation at a preselected wavelength, the molecule is detectable at low concentrations either visually or using conventional fluorescence detection methods. Electrochemiluminescent molecules such as ruthenium chelates and its derivatives or nitroxide amino acids and their derivatives are detectable at femtomolar ranges and below.

In one embodiment, an optionally detectable moiety includes one of:

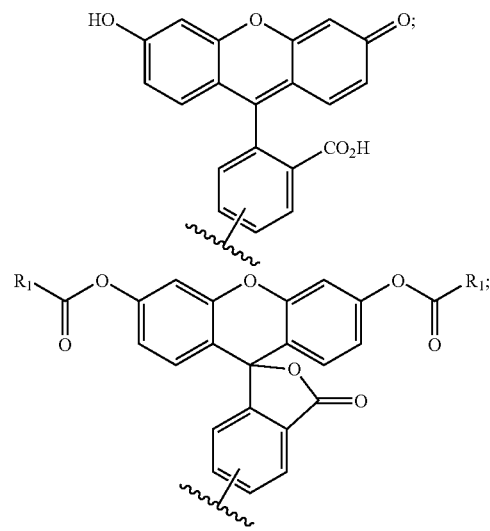

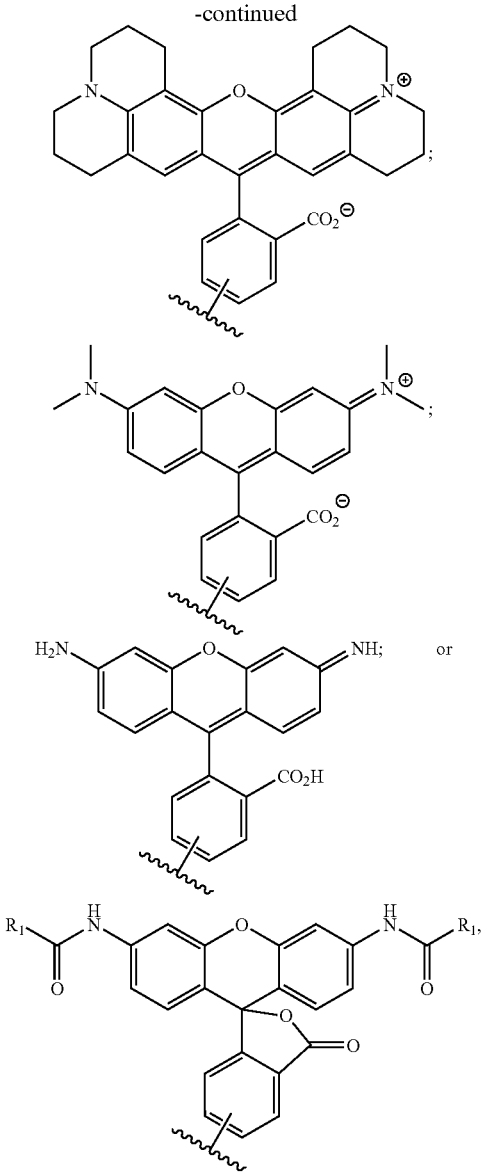

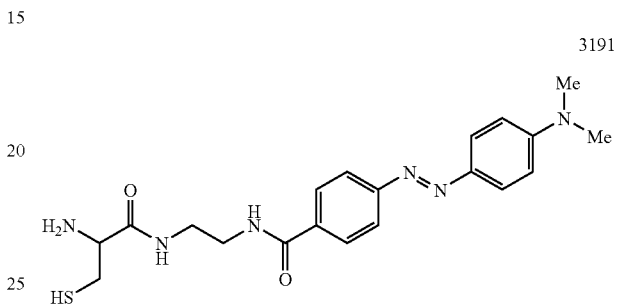

wherein $R_1$ is, for example, $(C_1\text{-}C_8)$alkyl, optionally substituted with one or more substituents.

Methods that may be employed to detect and/or isolate moiety labeled proteins include chromatographic techniques including gel filtration, fast-pressure or high-pressure liquid chromatography, reverse-phase chromatography, affinity chromatography, ion exchange chromatography, electrophoresis, capillary electrophoresis and isoelectric focusing. Other methods of separation are also useful for detection and subsequent isolation, for example, electrophoresis, isoelectric focusing and mass spectrometry.

Separation can also be performed through other biochemical separation methods such as immunoprecipitation and immobilization of antibodies on filters or other surfaces such as beads, plates or resins. For example, protein may be isolated by coating paramagnetic beads with a protein-specific antibody. Beads are separated from the protein translation extract using magnetic fields.

Many devices designed to detect proteins are based on the interaction of a target protein with a specific acceptor molecule, for instance, an immobilized acceptor molecule. Such devices can also be used to detect proteins once they contain affinity moieties such as biodetectors based on sensing changes in surface plasmons, light scattering and electronic properties of materials that are altered due to the interaction of the target molecule with the immobilized acceptor group.

B. Quenching Excess Labeling Reagent

In one embodiment, the fluorescence of excess un-reacted label (e.g., compound 3028) may be quenched by addition of a quenching reagent to the labeling reaction. The quenching reagent can be, for example, any beta-mercaptoethylamine conjugated to a known fluorescent quencher. One possible example of such a quenching reagent is compound 3191.

The beta-mercaptoethylamine can react with the cyanobenzothiazole moiety of any unreacted labeling reagent, thereby conjugating the quencher to the fluorophore of the labeling reagent. A quenching reagent of this sort would not react with or quench any labels that have previously been conjugated to proteins.

Moieties Detectable Using Electromagnetic Radiation

Moieties detectable using electromagnetic radiation include but are not limited to dansyl fluorophores, coumarins and coumarin derivatives, fluorescent acridinium moieties, benzopyrene based fluorophores, as well as 7-nitrobenz-2-oxa-1,3-diazole, and 3-N-(7-nitrobenz-2-oxa-1,3-diazol-4-yl)-2,3-diamino-propionic acid. In one embodiment, the fluorescent moiety has a high quantum yield of fluorescence at a wavelength different from native amino acids and has high quantum yield of fluorescence which can be excited in either the UV or visible portion of the spectrum, or both the UV and visible portions of the spectrum. Upon excitation at a preselected wavelength, the moiety is detectable at low concentrations either visually or using conventional fluorescence detection methods. Electrochemiluminescent labels such as ruthenium chelates and its derivatives or nitroxide amino acids and their derivatives are detectable at the femtomolar ranges and below.

In addition to fluorescent moieties, a variety of moieties with physical properties based on the interaction and response of the moiety to electromagnetic fields and radiation can be used to detect protein production. These properties include absorption in the UV, visible and infrared regions of the electromagnetic spectrum, presence of chromophores which are Raman active, and can be further enhanced by resonance Raman spectroscopy, electron spin resonance activity and nuclear magnetic resonances and molecular mass, e.g., via a mass spectrometer. These electromagnetic spectroscopic properties of the moiety are preferably not possessed by native amino acids or are readily distinguishable from the properties of native amino acids.

Fluorescent and other moieties with detectable electromagnetic spectral properties can be detected by various instruments, such as spectrometers or fluorometers and the like, and distinguished from the electromagnetic spectral properties of native amino acids. Spectrometers are include fluorescence, Raman, absorption, electron spin resonance, visible, infrared and ultraviolet spectrometers. Other moieties, such as moieties with distinct electrical properties can be detected by an apparatus such as an ammeter, voltmeter or other spectrometer. Physical properties of moieties which relate to the distinctive interaction of the label with an electromagnetic field is readily detectable using instruments such as fluorescence, Raman, absorption, or electron spin resonance spectrometers. Moieties may also undergo a chemical, biochemical, electrochemical or photochemical reaction such as a color change in response to external forces or agents such as an electromagnetic field or reactant molecules which allows its detection.

Regardless of which class of fluorescent compounds is used, detection may involve physical separation of the proteins from other biomolecules present in the cellular or cell-free protein system. Protein separation can be performed using, for example, gel electrophoresis or column chromatography. Detection of a protein containing a fluorophore by gel electrophoresis can be accomplished using conventional fluorescence detection methods. After protein synthesis in a cell-free system, the reaction mixture, which contains all of the biomolecules necessary for protein synthesis as well as proteins, is loaded onto a gel which may be composed of polyacrylamide or agarose. Subsequent to loading the reaction mixture, a voltage is applied which spatially separates the proteins on the gel in the direction of the applied electric field. The proteins separate and appear as a set of discrete or overlapping bands which can be visualized using a pre- or post-gel staining technique such as Coomasie blue staining. The migration of the protein band on the gel is a function of the molecular weight of the protein with increasing distance from the loading position being a function of decreasing molecular weight. Bands on the gel which contain N-terminal Cys labeled proteins will exhibit fluorescence when excited at a suitable wavelength. These bands can be detected visually, photographically or spectroscopically and, if desired, the proteins purified from gel sections.

The molecular weight and quantity of the protein can be determined by comparison of its band position on the gel with a set of bands of proteins of predetermined molecular weight which are labeled, e.g., fluorescently labeled. For example, a protein of molecular weight 25,000 could be determined because of its relative position on the gel relative to a calibration gel containing the commercially available standard marker proteins of known quantities and with known molecular weights (bovine serum albumin, 66 kD; porcine heart fumarase, 48.5 kD; carbonic anhydrase, 29 kD, β-lactoglobulin, 18.4 kD; α-lactoglobulin, 14.2 kD; Sigma Chemical; St. Louis, Mo.). Calibration proteins may contain a similar moiety for convenient detection using the same method as the moiety bearing the protein. This can be accomplished in many cases by directly reacting the calibration proteins with a molecule similar or identical to the moiety. Thus, a calibration protein (protein marker), such as one or more selected based on pI or molecular weight, may be labeled by the method of the invention, e.g., using a fluorescein, rhodamine, BODIPY or infrared type moiety, and optionally isolated.

For example, the calibration proteins can be modified with dansyl chloride or with a NHS modified BODIPY FL so as to obtain their fluorescent counterparts. These fluorescent proteins can be analyzed using PAGE. Combined detection of these fluorescent calibration proteins along with that of sample proteins which contain a fluorescent moiety can accurately determine both the molecular weight and quantity of the protein synthesized. If necessary, the amounts of moiety within each calibration and protein can be determined to provide an accurate quantitation. Proteins with predetermined levels of a fluorescent moiety can be used advantageously to provide for quantitation of the moiety bearing sample protein.

Other methods of protein separation are useful for detection and subsequent isolation and purification of sample proteins containing moieties detectable with electromagnetic radiation including capillary electrophoresis, isoelectric focusing, low pressure chromatography and high-performance or fast-pressure liquid chromatography. In these cases, the individual proteins are separated into fractions which can be individually analyzed by fluorescent detectors at the emission wavelengths of the moieties. Alternatively, on-line fluorescence detection can be used to detect proteins as they emerge from the column fractionation system. A graph of fluorescence as a function of retention time provides information on both the quantity and purity of proteins produced.

Uses and Exemplary Detection Methods for Labeled Proteins

The moiety containing proteins prepared by the methods of the invention are useful for any purpose including but not limited to detect the amount or presence of a particular protein, to isolate a protein, to facilitate high or low throughput screening, to detect protein-protein, protein-DNA or other protein-based interactions (e.g., using protein microarrays in which the moiety is used to bind proteins to the array or to detect bound proteins), to enhance the immunogenecity of a protein (for example, the N-terminus of one or more proteins may be labeled with a hapten to enhance the production of antibodies to the protein, as well as to facilitate antigen purification prior to immunization), to target a protein to a particular cellular or subcellular location (e.g., a label which is a protein localization domain may target the protein to the nucleus, chloroplast or mitochondria, or to specific cells, e.g., via a liver specific antibody), to provide site-specific orientation of a protein, for example, a ligand for the moiety is attached to a semi-solid or solid surface or to a linker of any length, e.g., an organic linker like polyethylene glycol ("PEG"), attached to a semi-solid or solid surface, such as glass, to prepare a chimeric protein comprising a reporter label, e.g., luciferase, and a protein of interest, e.g., CYP450, to prepare protein markers, or to map peptides, antigenic epitopes and binding sites on a protein.

Moreover, the labeled proteins find use in protein display technologies and directed evolution. Ribosome, nucleic acid-protein fusion and phage display technologies are widely being used to study protein-protein interactions and directed evolution. In ribosome related display technologies, an in vitro lysate expression system is employed for the production of mRNA-protein-ribosome complexes or mRNA-protein/cDNA-protein/DNA-protein fusion products (see published U.S. Application No. 2001/0046680, and U.S. Pat. Nos. 6,194,550; 6,207,446; and 5,922,545). The N-terminal labeling of proteins using a derivative of the invention aids in the isolation, identification and selection of targets. This approach is also useful for the detection of protein interactions in ribosome/nucleic acid-protein display-based protein microarrays. Derivatives of the invention are thus particularly useful for the isolation, characterization and identification of protein targets.

The use of in vitro lysate-based protein expression in phage display has been described in published U.S. Application No. 2001/0029025. cDNA/mRNA libraries are expressed in cell lysates with a derivative of the invention and phage display libraries expressing cDNAs are screened against the in vitro expressed proteins. Interacting proteins can be easily identified by the N-terminal label without the need for cloning steps. This approach is also useful in the selection of protein variants in directed evolution. In addition, labeled protein synthesized in vitro using a derivative of the invention can be employed to detect protein interactions involving phage display, e.g., use with phage display-based protein microarrays/bead technologies. Multiplexing is also possible.

Another approach for directed evolution is described in published U.S. Application No. 2001/0039014, where in vitro transcription and translation in cell lysates is used for directed evolution of proteins. In this approach, the isolation, purification and characterization of mutant proteins with improved functions could be readily accomplished using N-terminal labeling with a derivative of the invention.

Further, the labeled proteins may be introduced to cells, e.g., via endocytosis, permeabilization or microinjection.

Mass spectrometry measures the mass of a molecule. The use of mass spectrometry in biology is continuing to advance rapidly, finding applications in diverse areas including the analysis of carbohydrates, proteins, nucleic acids and biomolecular complexes. For example, the development of matrix assisted laser desorption ionization (MALDI) mass spectrometry (MS) has provided an important tool for the analysis of biomolecules, including proteins, oligonucleotides, and oligosachamides. This technique's success derives from its ability to determine the molecular weight of large biomolecules and non-covalent complexes (>500,000 Da) with high accuracy (0.01%) and sensitivity (subfemtomole quantities). Thus far, it has been found applicable in diverse areas of biology and medicine including the rapid sequencing of DNA, screening for bioactive peptides and analysis of membrane proteins.

Surface plasmon resonance (SPR) may be used to study protein/protein interactions. SPR is based on a change in the optical properties, particularly the refractive index of a surface after binding. This change, which can be measured very accurately, can then be used to detect both the extent and rate of binding. For example, incident light striking the back side of a thin gold layer, having a ligand monolayer on the front side, at variable angle penetrates into the ligand monolayer. Interaction occurs with the surface plasmons and, at a certain angle, the reflected light is reduced to a minimum due to plasmon resonance. The position of the minimum is detected and permits calculation of the refractive index. Binding of a molecule by the ligand changes the refractive index. SPR has been used to measure adsorption of proteins on polymer surfaces, protein binding to DNA, interactions of proteins with self-assembled monolayers on gold surfaces, interactions of proteins with phospholipid layers, and antibody-antigen interactions. For instance, a sensor chip with a carboxymethylated dextran matrix (Biocore) is pre-immobilized with streptavidin. Biotin labeled proteins prepared by the methods of the invention are contacted with one or more proteins and optical properties before and after contacting determined.

Electrophoresis may be employed to detect and/or isolate proteins or to detect the interaction of molecules with proteins which are translated in a translation system. Many proteins are capable of simultaneously interacting with multiple protein partners. For example, some proteins may have up to 86 proteins that they interact within the cell. The use of labeled proteins, e.g., labeled with affinity, fluorophore, luminescent or bioluminescent labels, in conjunction with electrophoresis allows the observation of an unlimited number of simultaneous protein-protein and/or protein-nucleic acid interactions.

Thus, the methods of the invention allow for a large number of molecules to be rapidly screened for possible interaction with the expressed protein of specific genes, even when the protein has not been isolated or its function identified. It also allows a library of proteins expressed by a pool of genes to be rapidly screened for interaction with molecules, e.g., compounds, without the necessity of isolating the proteins. For example, a library of molecules can be screened to identify those which serve as ligands for specific target protein. The molecules might be part of a combinatorial library of compounds or present in a complex biological mixture such as natural samples which may contain therapeutic compounds. The molecules might interact with the nascent proteins by binding to them or to cause a change in the structure or other property of the nascent protein by chemical or enzymatic modification.

Interaction of a specific molecule can be determined by comparing the presence or absence of the nascent protein exposed to the specific molecule with a similar analysis or measurement of the nascent protein that has not been exposed. The binding strength of the molecule can then be ascertained by altering the concentration of the specific molecules added to the protein synthesis system and measuring the change in the relative intensity of bands assigned to the uncomplexed and complexed nascent protein. In addition to gel electrophoresis, which measures the electrophoretic mobility of proteins in gels such as a polyacrylamide gel, the detection and/or isolation of complexed or noncomplexed proteins can be performed using capillary electrophoresis (CE) (see, e.g., U.S. Pat. No. 5,571,680 (Chen)). CE measures the electrophoretic migration time of a protein which is proportional to the charge-to-mass ratio of the molecule.

In an embodiment, different labels are introduced to two or more proteins of interest, e.g., introduced at the N-terminus of each protein or at the N-terminus of one protein and internally on the other protein. For example, each distinct protein comprises a label that emits light at a wavelength that is different than the label on a different protein. The two labeled proteins are mixed under conditions favorable for binding. The binding mixture is then subjected to CE and complexes of the two proteins, as well as the noncomplexed proteins, are detected. In addition, labeling of potential ligands of the protein of interest with a second label which is sensitive to the proximity of the first label, e.g., using FRET, BRET or LRET, permits the detection of the proximity of the two labels.

One form of CE, sometimes termed affinity capillary electrophoresis, has been found to be highly sensitive to interaction of proteins with other molecules including small ligands as long as the binding produces a change in the charge-to-mass ratio of the protein after the binding event. For example, the interaction of an antibody with the nascent proteins can be detected due to a change in the effective electrophoretic mobility of the complex formed. However, the highest sensitivity may be obtained if the protein has a label with a specifically detectable electromagnetic spectral property such as a fluorescent dye. Detection of a peak in the electrophoresis chromatogram is accomplished by laser induced emission of mainly visible wavelengths. Examples of useful fluorescent dyes for CE include fluoroscein, rhodamine, Texas Red and BODIPY.

In addition to interactions that involve the binding of one or more molecules to the labeled proteins, interactions that result in a modification of the labeled protein including but are not limited to phosphorylation, proteolysis, and glycosylation, can be detected using electrophoresis.

To determine the concentration of a protein of interest in a sample, the sample can be mixed with a corresponding labeled protein of interest and a protein that binds to both the labeled and unlabeled protein of interest. The mixture can then be subjected to CE and the concentration of the protein of interest determined (see for example, U.S. Pat. No. 5,571,680 (Chen)). This technique can also be used for the capture of the labeled and/or unlabeled protein, for example, using techniques similar to ELISA, for example, via capture by an antibody specific to the cyanobenzothiazole, as in a "sandwich" ELISA. For examples of ELISA "sandwich" test procedures, see Schuurs and van Weemen, *J. Immunoassay* 1980; 1:229-49.

General Synthetic Methods

Labels and detectable moieties, for example, those that are covalently linked to a cyanobenzothiazole or derivative thereof, permit the ready detection of that molecule in a complex mixture after reaction with a peptide of interest. The label may be one that is added to the cyanobenzothiazole core by chemical synthesis by the techniques described herein, or by those techniques well known to those of skill in the art. For instance, the attachment of fluorescent or other labels onto a core molecule can be accomplished by chemical modification. See Greg T. Hermanson, *Bioconiugate Techniques*, Academic Press, San Diego, Calif. (1996). Additional information regarding general synthetic methods that may be used to prepare the compounds described herein may be found in March's *Advanced Organic Chemistry Reactions, Mechanisms, and Structure*, 5th Ed. by Michael B. Smith and Jerry March, John Wiley & Sons, Publishers; and Wuts et al. (1999), *Protective Groups in Organic Synthesis*, 3$^{rd}$ Ed., John Wiley & Sons, Publishers.

The methods of preparing compounds of the invention can produce isomers in certain instances. Although the methods of the invention do not always require separation of these isomers, such separation may be accomplished, if desired, by methods known in the art. For example, preparative high performance liquid chromatography methods may be used for isomer purification, for example, by using a column with a chiral packing.

The general methods for linking a cyanobenzothiazole to a linking group Y to form a compound of formula I are typically well known in the art. Such 'linking' or 'coupling' reactions are standard techniques. Techniques used to couple linking groups to various benzothiazole derivatives can be found in standard handbooks such as Hermanson's *Biocjoniuciate Techniques*. Of course, one skilled in the are would recognize that compounds of formula I can be prepared by not only a reaction between an appropriate cyanobenzothiazole and a group Y—X but also by a reaction between a cyanobenzothiazole-Y group with an appropriately functionalized group X, such as a group X with an appropriate electrophile or nucleophile. For example, a primary hydroxyl group on a linking group can be converted to a leaving group, such as a toluenesulfonyl group, which group can then be displaced with a nucleophile, for example, a deprotonated 6'-hydroxycyanobenzothiazole. Specific examples of forming cyanobenzothiazole-Y groups are described by Zhou (see *J. Amer. Chem. Soc.* 2006, 128(10), 3122).

Numerous succinimidyl esters that are useful for preparing compounds of formula I are commercially available, for example, from Invitrogen Corporation. Additionally, one skilled in the art can use commonly reagents and conditions for preparing succinimidyl esters. Hermanson's *Bioconjugate Techniques* provides an extensive description of linking reactions that can be used to prepare compounds of formula I, particularly in Part I, which describes "Functional Targets" and "The Chemistry of Reactive Groups" (pages 1-416). For example, common reagents used to prepare succinimidyl esters include N-hydroxysuccinimide ("NHS", *J. Am. Chem. Soc.*, 86:1839 (1964)) and a carbodiimide activating agent such as dicyclohexyl-carbodiimide ("DCC") or 1,3-dimethylaminoprproply-ethylcarbodiimide ("EDC"; *J. Am. Chem. Soc.*, 95:875 (1973)). Alternatively, a 'self-activating' NHS derivative can be used, such as N-trifluoroacetyl-succinimide ("TFA-NHS"), N,N-disuccinimidyl carbonate (*Tetrahedron Lett.*, 22:4817 (1981)), or O—(N-succinimidyl)-N,N,N',N'-bis(tetramethylene)uranium hexafluorophosphate. Depending on the reactivity and solubility of the benzothiazole or linking group being activated, the conditions can range from organic to aqueous solvents. For example, a suitable organic solvent can be dimethylformamide ("DMF"). These reactions can be run in the presence of a base, such as a hindered amine base, for example, triethylamine or diethylisopropylamine, whereas aqueous conditions may include adjusting the pH to a range from about 6.5 to about 8.5.

When a group X—Y contains an amine, such as with a cyclic nucleotide, a nucleic acid, or many chemotherapeutics and proteins, then a succinimidyl ester of such a group can be used in the coupling reaction. When the group X contains an acid, such as with many quenchers, proteins, chemotherapeutics, and avidins, then the acid can be converted to a succinimidyl ester and combined with an amine-terminated Y group that has been previously linked to a cyanobenzothiazole. Other activating groups, such as sulfosuccinimidyl esters, tetrafluorophenyl esters, sulfodichlorophenol esters, isothiocyanates, sulfonyl chlorides, dichlorotriazines, aryl halides, or acyl azides can be used in place of succinimidyl esters to link with amines. Furthermore, one skilled in the art can readily convert certain organic moieties to suitable amines or acids using standard transformations, including oxidations, reductions, and displacement reactions. Additionally, protecting groups can be used to simplify the preparation of certain compounds of formula I. The use of protecting groups is well known in the art (see for example, see for example, Greene, *Protecting Groups In Organic Synthesis*; Wiley: New York, 1981).

The following Examples are intended to illustrate the above invention and should not be construed as to narrow its scope. One skilled in the art will readily recognize that the Examples suggest many other ways in which the present invention could be practiced. It should be understood that many variations and modifications may be made while remaining within the scope of the invention.

EXAMPLES

Example 1

Preparation of Cyanobenzothiazole Derivatives

Part A. Synthesis of 4-(3-(2-cyanobenzo[d]thiazol-6-yloxy)propylcarbamoyl)-2-(3-(dimethylamino)-6-(dimethyliminio)-6H-xanthen-9-yl)benzoate; "2-Cyano-(6-oxopropylamidotetramethyl-5'-carboxyrhodamine) benzothiazole" (compound 3028)

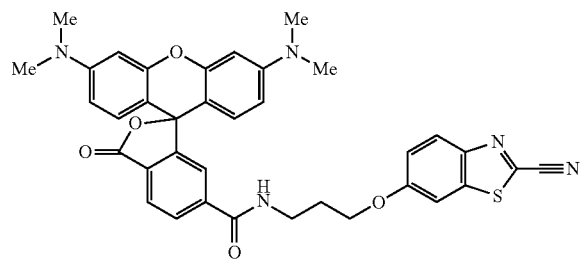

(3028)

Method A:

A flask containing 100 mg of 6-(N-Boc-3-aminopropyloxy)-2-cyano-benzothiazole (or "tert-butyl 3-(2-cyanobenzo[d]thiazol-6-yloxy)propylcarbamate", (W. Zhou, *J. Amer. Chem. Soc.* 2006, 128(10), 3122)) was stirred at 0° C. in dichloromethane (1 mL), trifluoroacetic acid (1 mL), and anisole (250 uL). After 2 hours, solvent was evaporated. Ether (2 mL) was added to precipitate the product. The white solid was washed 2 times with 2 mL of diether ether and dried under vacuum. The solid was used without further purification.

To a flask containing the above solid was added 6-TAMRA SE (138 mg, 0.3 mmol, 1 equiv) dissolved in 1 mL DMF and DIPEA (50 μL). After 24 hours at room temperature, the solvent was removed in vacuo. The residue was eluted through silica in a 90% heptane/10% methanol eluent. Appropriate fractions were combine and evaporated. The film was dissolved in 1 mL acetone and precipitated with 6 mL diethyl ether to yield 10 mg solid compound 3028. $^1$H NMR (300 MHz, DMSO) δ 8.78 (t, 1H, J=5.6), 8.20 (td, 2H, J=4.1, 8.3), 8.03 (d, 1H, J=9.0), 7.78 (s, 2H), 7.20 (dd, 1H, J=2.5, 9.1), 6.92 (d, 5H, J=23.2), 4.09 (t, 2H, J=5.9), 3.41 (dd, 3H, J=6.1, 11.9), 3.19 (s, 12H), 2.43 (d, 10H, J=1.7), 1.98 (dd, 2H, J=6.0, 12.1).

Alternatively, the compounds may be purified by preparative reverse phase HPLC.

Analogous compounds with fluorescein, Alexa 633, biotin, and IC-5 labels were synthesized using method A by substituting the TAMRA-SE for the appropriate FAM-SE (Sigma), biotin-SE (Sigma), Alexa-633-SE (Invitrogen), or IC-5-SE (Biosearch Technologies, Cat. No. FC-1065S-25). As would be readily recognized by one skilled in the art, similar techniques can be used to prepare cyanobenzothiazole derivatives linked to other groups of interest, including reporter moieties, affinity labels, quencher moieties, photocrosslinking moieties, or solid supports.

Part B. The Following Compounds were Synthesized Using Method A Utilizing the Appropriate 5,6FAM-SE, Bodipy488-SE, biotin-SE, or IC-5-SE in place of 6-TAMARA SE 4(and 5)-(3-(2-cyanobenzo[d]thiazol-6-yloxy)propylcarbamoyl)-2-(3-hydroxy-6-oxo-6H-xanthen-9-yl)benzoic acid (e.g., compound 3066)

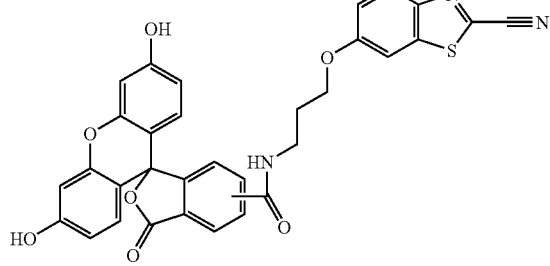

Mixture of isomers (66%:35%); $^1$H NMR (300 MHz, DMSO) δ 10.12 (s), 8.90 (t), 8.76 (t), 8.44 (d), 8.22 (dd), 8.11 (m), 7.89 (d), 7.82 (d), 7.66 (s), 7.33 (m), 7.21 (dd), 6.66 (d), 6.54 (m), 4.18 (t), 4.08 (t), 3.50 (dd), 3.37 (t), 2.07 (m), 1.97 (m), 1.22 (s), 0.83 (t). MS: Calcd for $C_{32}H_{21}N_3O_7S$, 592.1. found 592.

(Z)—N-(3-(2-cyanobenzo[d]thiazol-6-yloxy)propyl)-3-(1-(difluoroboryl)-5-((3,5-dimethyl-2H-pyrrol-2-ylidene)methyl)-1H-pyrrol-2-yl)propanamide (compound 3226)

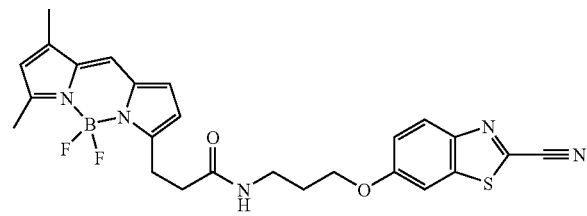

$^1$H NMR (300 MHz, DMSO) δ 8.17 (d, 1H, J=9.1), 8.07 (t, 1H, J=5.7), 7.87 (d, 1H, J=2.5), 7.67 (s, 1H), 7.35 (dd, 1H, J=2.5, 9.1), 7.08 (d, 1H, J=3.9), 6.56 (s, OH), 6.39 (d, 1H, J=4.0), 6.33 (s, 1H), 4.12 (t, 2H, J=6.3), 3.30 (dd, 2H, J=6.4, 12.2), 3.12 (t, 2H, J=7.5), 2.50 (s, 3H), 2.28 (s, 3H), 1.95 (p, 2H, J=6.4). MS Calcd for $C_{25}H_{24}BF_2N_5O_2S$, 508. found 507.

N-(3-(2-cyanobenzo[d]thiazol-6-yloxy)propyl)-5-((3aS,4S,6aR)-2-oxo-hexahydro-1H-thieno[3,4-d]imidazolyl)pentanamide (compound 3167)

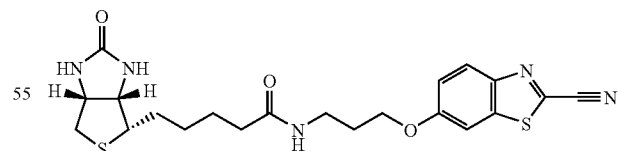

$^1$H NMR (300 MHz, DMSO) δ 8.18 (d, 1H, J=9.1), 7.92 (dd, 2H, J=4.1, 6.2), 7.36 (dd, 1H, J=2.6, 9.1), 6.44 (s, 2H), 4.32 (dd, 1H, J=4.4, 7.7), 4.14 (m, 3H), 3.26 (q, 2H, J=6.5), 3.10 (m, 1H), 2.83 (dd, 1H, J=5.1, 12.4), 2.60 (d, 1H, J=12.3), 2.10 (t, 2H, J=7.3), 1.94 (t, 2H, J=6.4), 1.52 (m, 4H), 1.33 (m, 2H). MS Calcd for $C_{21}H_{25}N_5O_3S_2$ 460.1. found 460.4.

2-((1E,3E,5E)-5-(1-(6-(3-(2-cyanobenzo[d]thiazol-6-yloxy)propylamino)-6-oxohexyl)-3,3-dimethylindolin-2-ylidene)penta-1,3-dienyl)-1-ethyl-3,3-dimethyl-3H-indolium chloride (compound 3272)

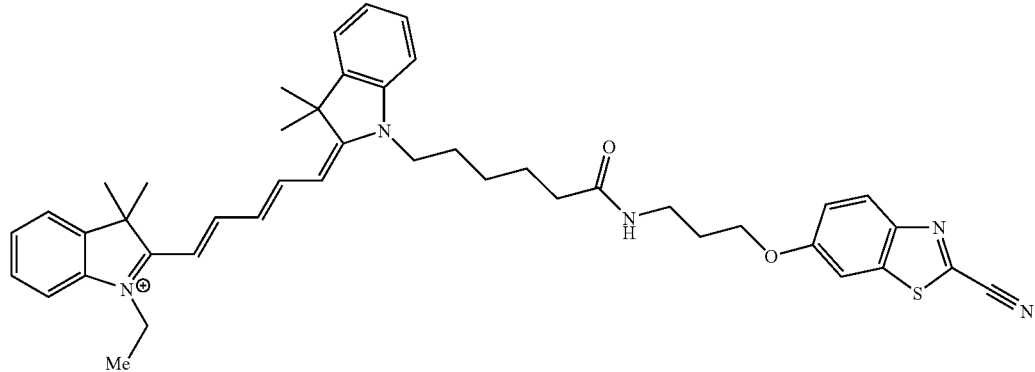

(3272)

$^1$H NMR (300 MHz, DMSO) δ 8.31 (t, 2H, J=13.1), 8.11 (d, 1H, J=9.1), 7.84 (m, 2H), 7.60 (d, 2H, J=7.0), 7.29 (m, 6H), 6.55 (t, 1H, J=12.3), 6.26 (dd, 2H, J=4.0, 13.8), 4.08 (m, 7H), 3.84 (s, 15H), 3.54 (s, OH), 3.19 (d, 2H, J=5.9), 2.49 (dt, 4H, J=1.8, 3.7), 2.30 (s, OH), 2.05 (m, 2H), 1.85 (m, 2H), 1.66 (d, 12H, J=2.8), 1.52 (dd, 2H, J=7.3, 14.7), 1.33 (dd, 2H, J=7.3, 14.9), 1.24 (t, 3H, J=7.1). MS Calcd for $C_{44}H_{50}N_5O_2S+$ 712.4. found 712.

Part C. Synthesis of 4-(6-(2-cyano-5-fluorobenzo[d]thiazol-6-yloxy)hexylcarbamoyl)-2-(3-(dimethylamino)-6-(dimethyliminio)-6H-xanthen-9-yl)benzoate (compound 3086)

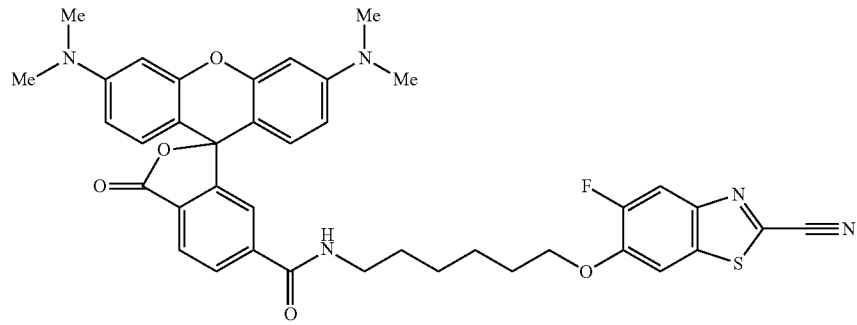

(3086)

5-Fluoro-6-hydroxybenzo[d]thiazole-2-carbonitrile (200 mg) was heated to 65° C., 50 W, 40 minutes in a microwave with acetone (2 mL), potassium carbonate (284 mg), and tert-butyl 6-bromohexylcarbamate (265 μL). Afterward, an additional 150 μL tert-butyl 6-bromohexylcarbamate was added and reaction was heated to 80° C., 75 W, for 23 minutes. The reaction was partitioned between ethyl acetate and bicarbonate, washed with aqueous citric acid and brine, and evaporated. The crude material eluted through a silica column with a mixture of heptane: ethyl acetate (3:1). Yield 78%.

tert-Butyl 6-(2-cyano-5-fluorobenzo[d]thiazol-6-yloxy)hexylcarbamate (200 mg) was added to cold (0° C.) solution of dichloromethane (3 mL), trifluoroacetic acid (3 mL), and anisole (300 μL). After 15 minutes, the majority of solvent was evaporated, and 30 mL of diethyl ether was added. The precipitate was isolated (165 mg).

6-(6-Aminohexyloxy)-5-fluorobenzo[d]thiazole-2-carbonitrile (50 mg) was stirred with 6-TAMRA-SE (65 mg) as in method A above. Yield 10 mg. $^1$H NMR (300 MHz, DMSO) δ 8.67 (t, 1H, J=5.8), 8.17 (q, 2H, J=8.2), 8.05 (dd, 2H, J=9.7, 21.1), 7.78 (s, 1H), 6.90 (d, 5H, J=26.3), 4.08 (t, 2H, J=6.4), 3.17 (s, 11H), 1.73 (m, 2H), 1.48 (m, 2H), 1.35 (s, 4H). MS Calcd for $C_{39}H_{36}FN_5O_5S$, 706.2. found 706.

Part D. Synthesis of 4-(6-(2-cyano-7-nitrobenzo[d]thiazol-6-yloxy)hexylcarbamoyl)-2-(3-(dimethylamino)-6-(dimethyliminio)-6H-xanthen-9-yl)benzoate (compound 3087)

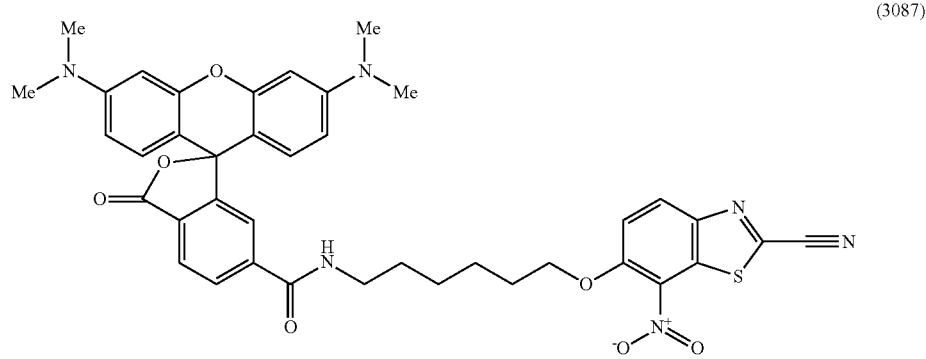

(3087)

6-Hydroxybenzo[d]thiazole-2-carbonitrile (352 mg) was heated in a microwave with ZrO(NO$_3$)$_2$×H$_2$O (462 mg) and acetone (7 mL) at 100° C. (200 W) for 10 min. Product was extracted with dichloromethane and eluted through silica with heptane:ethyl acetate (1:1). Yield 222 mg.

6-Hydroxy-7-nitrobenzo[d]thiazole-2-carbonitrile (100 mg) was heated to 70° C. at 50 W for 30 minutes in a microwave with acetone (2 mL), potassium carbonate (125 mg), and tert-butyl 6-bromohexylcarbamate (139 mg). After which an additional 150 µL tert-butyl 6-bromohexylcarbamate was added and reaction was heated to 80° C., 75 W, for 30 minutes. After which an additional 300 µL tert-butyl 6-bromohexylcarbamate, cesium carbonate (162 mg) and diglyme (1 mL) was added and reaction was heated to 100° C., 75 W, for 250 minutes. The reaction was partitioned between ethyl acetate and bicarbonate, washed with aqueous citric acid and brine, and evaporated. The crude material eluted through a silica column with a mixture of heptane: ethyl acetate (2:1). Yield 44% tert-Butyl 6-(2-cyano-7-nitrobenzo[d]thiazol-6-yloxy)hexylcarbamate (50 mg) was added to cold (0° C.) solution of dichloromethane (1 mL), trifluoroacetic acid (1 mL), and anisole (99 µL). After 30 minutes, the majority of solvent was evaporated, and 30 mL of diethyl ether was added. The precipitate was isolated and used without further purification.

6-(6-Aminohexyloxy)-7-nitrobenzo[d]thiazole-2-carbonitrile (51 mg) was stirred with 6-TAMRA-SE (50 mg) as in Method A above. Yield 13 mg. $^1$H NMR (300 MHz, DMSO) δ 8.72 (t, 1H), 8.58 (d, 1H, J=7.3), 8.22 (d, 2H, J=8.0), 7.83 (s, 2H), 6.98 (d, 5H), 4.39 (t, 2H), 3.24 (s, 15H), 1.82 (m, 2H), 1.52 (m, 4H), 1.40 (m, 2H). MS Calcd for C39H36N6O7S, 733.2. found 733.6.

Part E. Synthesis of 4-(6-(2-cyanobenzo[d]thiazol-6-ylamino)-6-oxohexylcarbamoyl)-2-(3-(dimethylamino)-6-(dimethyliminio)-6H-xanthen-9-yl)benzoate (compound 3082)

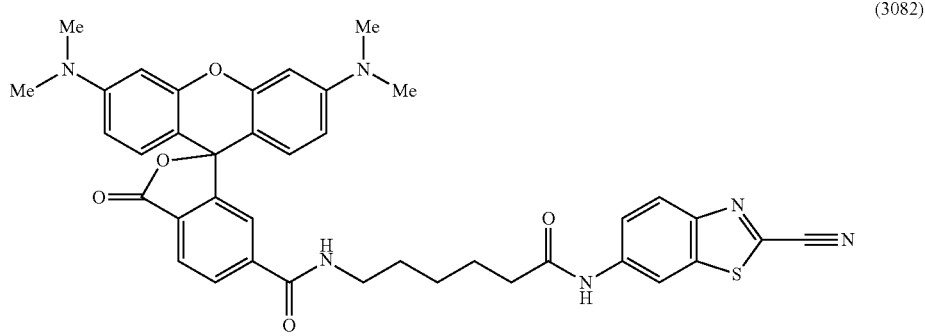 [SMILES: CN(C)c1ccc2c(c1)Oc1cc(N(C)C)ccc1C21OC(=O)c2ccc(C(=O)NCCCCCC(=O)Nc3ccc4nc(C#N)sc4c3)cc21]

(3082)

6-(tert-Butoxycarbonylamino)hexanoic acid (316 mg) was mixed with anhydrous THF (10 mL), 6-aminobenzo[d]thiazole-2-carbonitrile (200 mg), iso-butylchloroformate (193 µL), and N-methylmorpholine (314 µL) at −4° C. The reaction was allowed to stir overnight at RT. The reaction was partitioned between ethyl acetate and bicarbonate. The ethyl acetate layer was evaporated, and the residue was eluted through silica with heptane: ethyl acetate (1:2). Yield 354 mg.

tert-Butyl 6-(2-cyanobenzo[d]thiazol-6-ylamino)-6-oxohexylcarbamate (350 mg) was added to cold (0° C.) solution of dichloromethane (4 mL), trifluoroacetic acid (4 mL), and anisole (400 µL). After 135 minutes, the majority of solvent was evaporated, and 10 mL acetonitrile and 30 mL of diethyl ether was added. The mixture was allowed to sit overnight. The precipitate was isolated and used without further purification.

6-Amino-N-(2-cyanobenzo[d]thiazol-6-yl)hexanamide (100 mg) was stirred with 6-TAMRA-SE (122 mg) as in method A above. Yield (22 mg). $^1$H NMR (300 MHz, DMSO) δ 10.31 (s, 1H), 8.67 (dd, 2H, J=3.8, 7.2), 8.12 (m, 3H), 7.77 (s, 1H), 7.63 (dd, 1H, J=2.1, 9.1), 3.17 (s, 14H), 2.31 (t, 2H, J=7.4), 1.57 (m, 2H), 1.47 (m, 2H), 1.31 (m, 2H). MS: Calcd for $C_{39}H_{36}N_6O_5S$: 701.2. found 701.6.

Example 2

Synthesis of (E)-N-(2-(2-amino-3-mercaptopropanamido)ethyl)-4-((4-(dimethylamino)phenyl)diazenyl)benzamide (compound 3191)

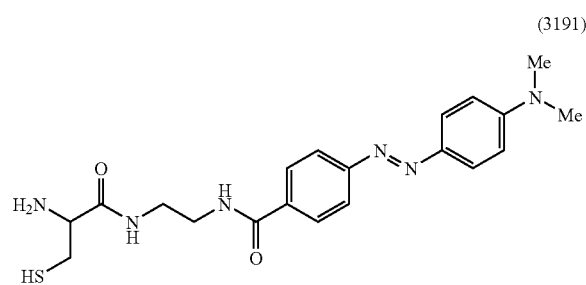 [SMILES: CN(C)c1ccc(/N=N/c2ccc(C(=O)NCCNC(=O)C(N)CS)cc2)cc1]

(3191)

(E)-2,5-Dioxopyrrolidin-1-yl 4-((4-(dimethylamino)phenyl)diazenyl)-benzoate (200 mg) was mixed with dimethyl formamide (5 mL), tert-butyl 1-(2-aminoethylamino)-1-oxo-3-(tritylthio)propan-2-ylcarbamate (333 mg), and diisopropylethylamine (285 μL). After 12 hours, the reaction was partitioned between ethyl acetate and aqueous citric acid. The organic layer was washed with bicarbonate and, then, brine. After evaproration, the residue was eluted through silica with heptane: ethyl acetate (1:1). Yield: 242 mg.

(E)-tert-Butyl 1-(2-(4-((4-(dimethylamino)phenyl)diazenyl)benzamido)-ethylamino)-1-oxo-3-(tritylthio)propan-2-ylcarbamate (240 mg) was added to a cold solution of trifluoroacetic acid (10 mL), water (500 μL), and triisopropylsilane (100 μL). After 5 hours, diethyl ether (50 mL) was added to precipitate product, compound 3191. The product was further purified by preparative reverse phase HPLC. Yield 60 mg. $^1$H NMR (300 MHz, DMSO) δ 8.56 (m, 2H), 8.18 (s, 3H), 7.92 (d, 2H, J=8.5), 7.75 (d, 4H, J=8.3), 6.78 (d, 2H, J=8.2), 3.85 (m, 1H), 3.35 (m, 3H), 3.20 (m, 1H), 3.01 (s, 6H), 2.85 (m, 2H), 2.50 (s, 1H).

Example 3

N-Terminal Peptide Labeling with a Cyanobenzothiazole Derivative

In this example, a cyanobenzothiazole-rhodamine reagent is added to solutions containing various concentrations of materials containing cysteine residues. The solutions are incubated with the cyanobenzothiazole-rhodamine reagent under conditions where an adduct can be formed between the N-terminal cysteine residue and the reagent. After incubation with the reagent, the presence of a new, labeled species is detected by fractioning a small portion of the reaction mixture onto a silica thin layer chromatography (TLC) plate and examining the presence of a fluorescent species.

Five different materials containing cysteine residues were reacted with a cyanobenzothiazole-rhodamine reagent. Tocinoic acid (Sigma) is a peptide containing an amino and carboxy terminal cysteine residue connected by a disulfide bond (peptide sequence: Cys-Tyr-Ile-Gln-Asn-Cys) (SEQ ID NO:7). To reduce the disulfide bonds in the peptide, 50 μl of 1 mM tocinoic acid was mixed with 5 μl 1 M HEPES pH 8.0, 0.25 μl Bond Breaker (Pierce Chemical Co) and 46 μl water. To create an oxidized Tocinoic acid solution, 50 μL of tocinoic acid (1 mM) was mixed with 5 μL 1 M HEPES pH 8.0 and 45 μl water. Bachem H4696 (Bachem Bioscience Inc., King of Prussia, Pa.) is a peptide (Gly-Cys-Lys-Asn-Phe-Phe-Trp-Lys) (SEQ ID NO:8) containing an internal cysteine residue. A working solution of Bachem H4696 was made by mixing 48 μl 5 mM Bachem H4696 with 0.25 μl Bond Breaker and 1 μl HEPES pH 8.0. Bachem H4702 is a peptide (Cys-Lys-Asn-Phe-Phe-Trp-Lys-Thr) (SEQ ID NO:9) containing an N-terminal cysteine residue. A working solution of Bachem H4702 was made by mixing 48 μl 5 mM Bachem H4702 with 0.25 μl Bond Breaker and 1 μl 1M HEPES pH 8.0. Working solutions of 10 mM Cys-Gly dipeptide (Sigma; 15 mg) and 20 mM Cysteine (Sigma) were also made.

A reaction buffer for the cyanobenzothiazole labeling reaction was made by mixing 500 μL 1 M HEPES pH 7.5 with 7.5 mL water. Six sets of reactions were set up to allow various molar ratios of peptide to reagent to be tested. Each set contained six reactions which would each contain a different cysteine material. The relative molar ratios of peptide to reagent tested varied from 0.3:1 to 2:1. To all reactions, 75 μl of reaction buffer was added. To each reaction in each set, a different amount of water was added: 16.7 μl to the first set, 13.3 μl to the second set, 10 μl to the third set, 6.7 μl to the fourth set and 3.3 μl to the fifth set. The sixth set of reaction tubes would not have any water added as it would constitute the highest ratio of cysteine material to cyanobenzothiazole reagent. One reaction tube was set up as a no peptide control in which 20 μl water was added.

Diluted solutions of cysteine (2.5 μl 20 mM cysteine to 100 μl with water), Bachem H4696 (10 μl of the above solution to 100 μl with water), Bachem H4702 (10 μl of the above solution to 100 μl with water) and Cys-Gly (5 μl of above solution to 100 μl with water) were added to different reaction tubes in each of the six sets to final reaction volumes of 95 μl. The oxidized tocinoic acid and reduced tocinoic acid were also added to different reaction tubes in each of the six sets to final reaction volumes of 95 μl. In total, each reaction tube in each of the 6 sets contained a different cysteine solution.

To all reaction tubes, 5 μl of 1 mM cyanobenzothiazole-rhodamine reagent was added and mixed. After a 15 minute incubation at room temperature, 1 μl from each reaction tube was spotted onto a silica gel TLC plate. The plate was developed in a mixture of 90 parts EtOH, 10 parts water and one part glacial acetic acid. After development, the plate was air dried, visualized under UV light to confirm the reaction proceeded to completion.

The no peptide control reaction containing only buffer and the cyanobenzothiazole-rhodamine reagent gave a strong fluorescent spot at an Rf value of −0.8 and a weak spot at an Rf value of ~0.4. This identifies the mobility of the original, unreacted cyanobenzothiazole reagent and demonstrates the reagent is unaffected by the reaction conditions.

Figure 3:
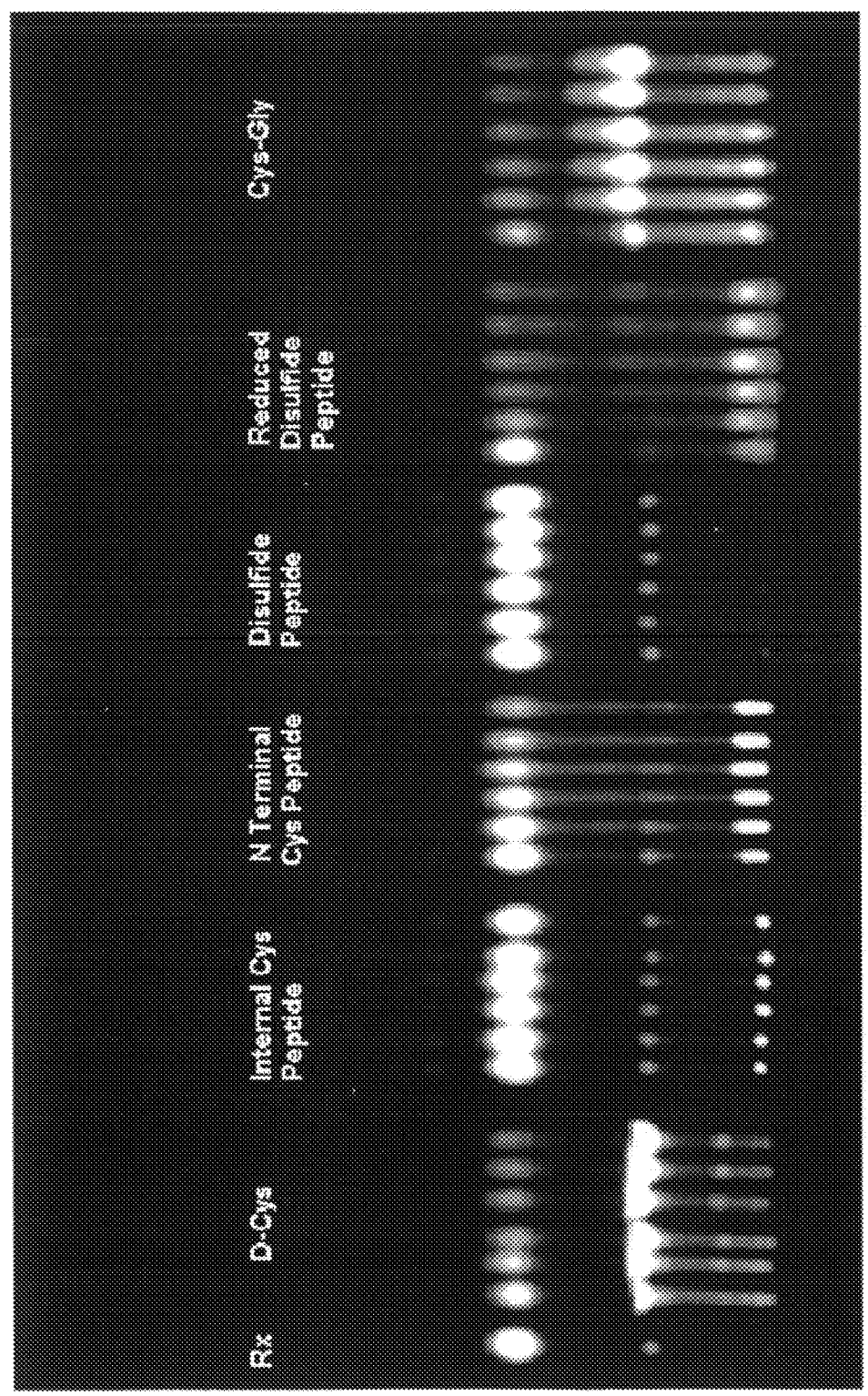
FIG. 3 shows an image of a thin layer chromatography (TLC) plate captured on an Ambis Imaging system set to detect the fluorescent emission from fluorescent species present on the TLC plate when exposed to ultraviolet light and collected through a filter excluding ultraviolet light present on the imaging camera.

FIG. 3 shows an image of a thin layer chromatography (TLC) plate captured on an Ambis Imaging system set to detect the fluorescent emission from fluorescent species present on the TLC plate when exposed to ultraviolet light and collected through a filter excluding ultraviolet light present on the imaging camera.

Reactions wherein increasing amounts of cysteine was used (lanes 2-7) show the presence of a new, strong fluorescence adduct with a mobility at an Rf value of ~0.42 along with the presence of low amounts of other species (adduct). The amount of new fluorescent species increase until the molar amount of the cysteine and benzothiazole are approximately equal (lanes 4-5). This demonstrates that 1) the reaction between cysteine and the cyanobenzothiazole-rhodamine reagent is rapid (~15 minutes), and 2) the reaction requires about 1 mole equivalent cysteine to react with 1 mole of cyanobenzo-thiazole reagent.

Reactions wherein increasing amounts of Bachem H4696 (peptide with an internal cysteine) was used (lanes 8-13) showed a fluorescent mobility pattern essentially the same as was seen with the cyanobenzothiazole reagent alone (lane 1). This most likely demonstrates 1) either internal cysteines are unable to react with the cyanobenzothiazole reagent, 2) a larger amount of the peptide is needed to react with the cyanobenzothiazole reagent, or 3) any adduct which does form is unstable and reverts back to the starting material readily making detection of the adduct almost impossible.

In contrast, reactions where increasing amounts of Bachem H4702 (peptide containing an N-terminal cysteine) showed a significant amount of adduct with very low mobility (lanes 14-19). The amount of new adduct formation increased with a corresponding loss of unreacted cyanobenzothiazole reagent. Therefore, the cyanobenzothiazole reagent is able to form a stable adduct with a peptide with an N-terminal cysteine. This is most likely caused by the formation of a cyclic benzothiazole product through the attack of the N-terminal amino group on the amino acid analogous to that seen with the formation of luciferin through the reaction with cysteine. However, if the N-terminal cysteine group is involved in a disulfide bond such as in the reaction with the oxidized tocinoic acid (lanes 20-25), no new adduct is formed and no loss of unreacted cyanobenzothiazole reagent is seen with increasing amounts of peptide.

If the disulfide bond in tocionic acid is reduced to free cysteine (reduced tocinoic acid above), the resulting N-terminal cysteine is available to react with the cyanobenzothiazole reagent (lanes 26-31) and a new adduct with low mobility is formed. The new adduct is formed in a manner similar to that seen in the cysteine reaction i.e. the amount of adduct formed is dependent on a ratio of 1 mole equivalent reduced tocinoic acid to 1 mole cyanobenzothiazole reagent. Reactions with the dipeptide Cys-Gly (lanes 32-37) also demonstrate the rapid labeling of a N-terminal cysteine by the cyanobenzothiazole reagent even in a small peptide.

Therefore, this example demonstrates that the cyanobenzothiazole reagent can readily label a peptide, large or small, containing an available N-terminal cysteine.

Example 4

Labeling Proteins with Cyanobenzothiazole Reagents

In this example, a protein with an N-terminal cysteine residue was labeled with a compound of the invention. The amount of labeling was compared to other proteins in the solution, and to a parallel reaction where the target protein was replaced with a protein identical to the target protein except that the N-terminal cysteine residue was exchanged for an alanine residue. The example demonstrates that: 1) a fusion protein construct can be constructed such that, when digested with TEV protease, it generates a protein of interest with an N-terminal cysteine; 2) exposure of a protein with an N-terminal cysteine residue, such as that produced by digestion of a properly designed fusion protein construct with TEV protease, will become highly fluorescent when exposed to a compound of the invention containing a fluorescent moiety, even though other proteins in the reaction without N-terminal cysteine residues gain little or no fluorescence, and; 3) a parallel reaction that contains a TEV digested fusion construct identical to the one that exposes a cysteine residue upon digestion, but which exposes an alanine residue, will show very little or no labeling of the proteins in the solution, including the protein identical to the protein having an N-terminal cysteine but where the N-terminal cysteine has been replaced with an alanine.

Figure 2A:
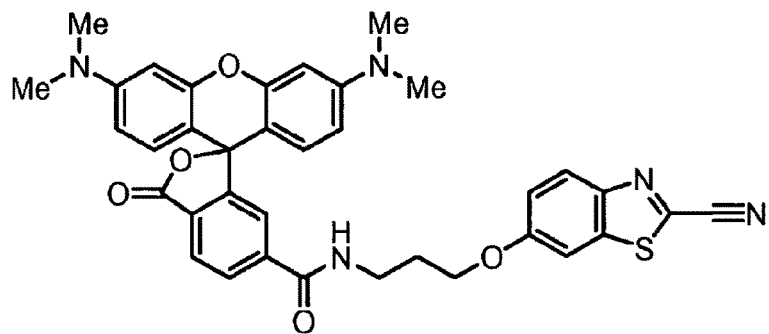
FIGS. 2(a) and 2(b) illustrate certain specific compounds useful in the compositions and methods of the invention, according to various embodiments.
Figure 2A:
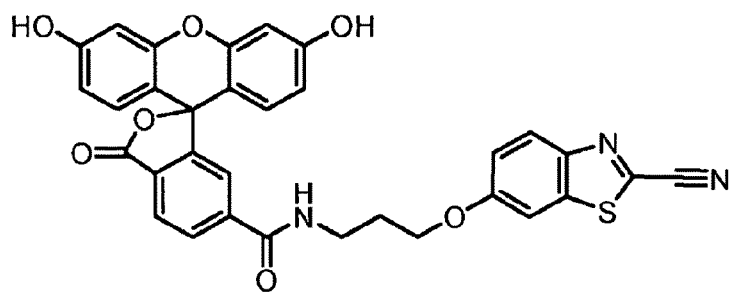
Figure 2A:
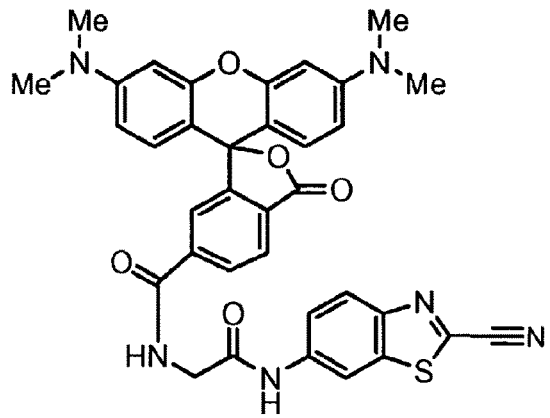
Figure 2A:
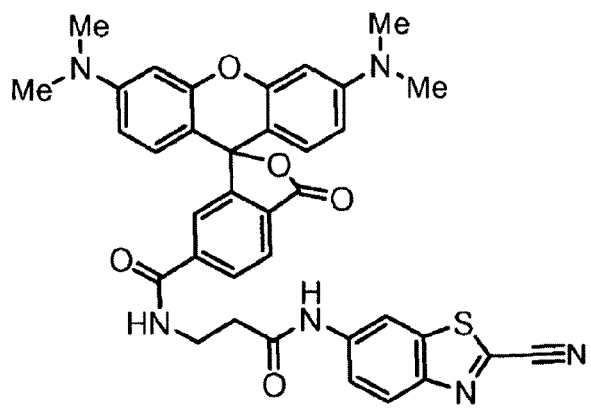
Figure 2B:
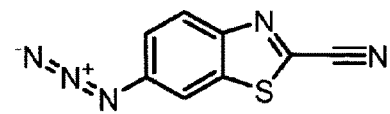
Figure 2B:
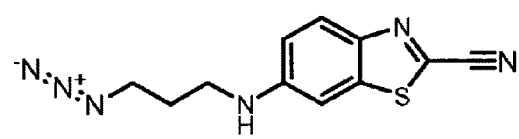
Figure 2B:
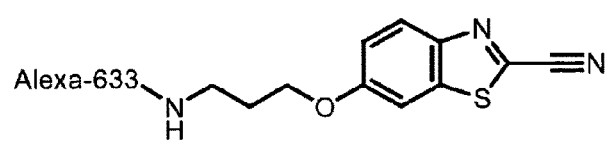
Figure 2B:
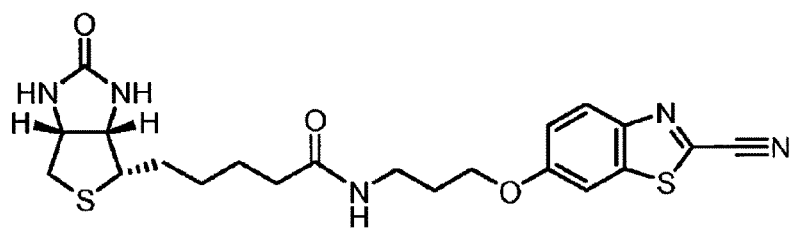
Figure 2B:
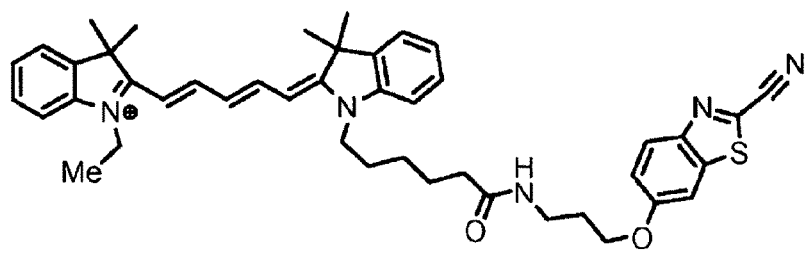

To demonstrate these points, an experiment—which is described in detail below—was performed having the following steps: A) recombinant DNA clones were constructed designed to express a fusion protein in E. coli having: i) an affinity protein tag [GST] at the N-terminus of the intact fusion construct for rapid and easy purification of the fusion protein species followed by, ii) a protein sequence encoding a TEV protease recognition site followed by, iii) another protein segment. Two constructs were created that differed only in that one construct would expose a cysteine residue at the new N-terminus of the protein produced by TEV cleavage of the fusion construct, whereas the other construct would expose an alanine residue at the new N-terminus; B) expression of the recombinant DNAs in E. coli and confirmation that the bacteria expressed the fusion proteins; C) purification of the fusion proteins from an E. coli lysate by employing the affinity protein tag, and; D) digestion of the fusion constructs followed by exposure of both intact and cleaved fusion protein to PBI compound 3128 (see FIG. 2(a)), followed by analysis to detect the labeling of protein species in the reaction mixtures.

Step A). Construction of Recombinant DNA Species Encoding the Fusion Protein Pairs.

Plasmid species were designed that encoded a prokaryotic promoter and translation initiation region followed in frame with the coding sequence of glutathione S transferase [GST, an affinity protein tag]. One version had the GST followed in frame by a coding sequence that contained a recognition sequence for TEV protease followed by a cysteine followed in frame with other proteins. A second plasmid species was designed to be identical to the plasmid above but with the encoded cysteine following the TEV site replaced with an alanine. The protein coding regions of beetle luciferase was then fused in frame with the end of the coding sequence encoding the TEV protease site such that there was one continuous coding region that encoded all of these polypeptide segments.

The plasmids were confirmed by DNA sequence analysis. Amino acid and nucleotide sequences for GST-Luc (Ala and Cys):

Amino Acid Sequence GST-(TEV-Cys)-Luc (SEQ ID NO: 10)

MSPILGYWKIKGLVQPTRLLLEYLEEKYEEHLYERDEGDKWRNKKFELGLEFPNLPYYIDGDVKLTQSMAII

RYIADKHNMLGGCPKERAEISMLEGAVLDIRYGVSRIAYSKDFETLKVDFLSKLPEMLKMFEDRLCHKTYL

-continued

NGDHVTHPDFMLYDALDVVLYMDPMCLDAFPKLVCFKKRIEAIPQIDKYLKSSKYIAWPLQGWQATFGGG

DHPPKSGGGGGENLYFQCIAMEDAKNIKKGPAPFYPLEDGTAGEQLHKAMKRYALVPGTIAFTDAHIEVNI

TYAEYFEMSVRLAEAMKRYGLNTNHRIVVCSENSLQFFMPVLGALFIGVAVAPANDIYNERELLNSMNISQ

PTVVFVSKKGLQKILNVQKKLPIIQKIIIMDSKTDYQGFQSMYTFVTSHLPPGFNEYDFVPESFDRDKTIALI

MNSSGSTGLPKGVALPHRTACVRFSHARDPIFGNQIIPDTAILSVVPFHHGFGMFTTLGYLICGFRVVLMY

RFEEELFLRSLQDYKIQSALLVPTLFSFFAKSTLIDKYDLSNLHEIASGGAPLSKEVGEAVAKRFHLPGIRQG

YGLTETTSAILITPEGDDKPGAVGKVVPFFEAKVVDLDTGKTLGVNQRGELCVRGPMIMSGYVNNPEATN

ALIDKDGWLHSGDIAYWDEDEHFFIVDRLKSLIKYKGYQVAPAELESILLQHPNIFDAGVAGLPDDDAGELP

AAVVVLEHGKTMTEKEIVDYVASQVTTAKKLRGGVVFVDEVPKGLTGKLDARKIREILIKAKKGGKSKLV

Nucleotide Sequence for GST-(TEV-Cys)-Luc (SEQ ID NO: 11)

atgtccctatactaggttattggaaaattaagggccttgtgcaacccactcgacttcttttggaatatcttgaagaaaaatatgaagagcatttgtatgag cgcgatgaaggtgataaatggcgaaacaaaaagtttgaattgggtttggagtttcccaatcttccttattatattgatggtgatgttaaattaacacagtct atggccatcatacgttatatagctgacaagcacaacatgttgggtggttgtccaaaagagcgtgcagagatttcaatgcttgaaggagcggttttggat attagatacggtgtttcgagaattgcatatagtaaagactttgaaactctcaaagttgattttcttagcaagctacctgaaatgctgaaaatgttcgaagat cgtttatgtcataaaacatatttgaatggtgatcatgtaacccatcctgacttcatgttgtatgacgctcttgatgttgttttatacatggacccaatgtgcc tggatgcgttcccaaaattagtttgtttcaaaaaacgtattgaagctatcccacaaattgataagtacttgaaatccagcaagtatatagcatggccttttgca gggctggcaagccacgtttggtggtggcgaccatcctccaaaatccggaggtggtggcggagaaaacctgtacttccaatgcatcgccATGGA

AGACGCCAAAAACATAAAGAAAGGCCCGGCGCCATTCTATCCTCTAGAGGATGGAACCGCTGGAGA

GCAACTGCATAAGGCTATGAAGAGATACGCCCTGGTTCCTGGAACAATTGCTTTTACAGATGCACATA

TCGAGGTGAACATCACGTACGCGGAATACTTCGAAATGTCCGTTCGGTTGGCAGAAGCTATGAAACG

ATATGGGCTGAATACAAATCACAGAATCGTCGTATGCAGTGAAAACTCTCTTCAATTCTTTATGCCGG

TGTTGGGCGCGTTATTTATCGGAGTTGCAGTTGCGCCCGCGAACGACATTTATAATGAACGTGAATT

GCTCAACAGTATGAACATTTCGCAGCCTACCGTAGTGTTTGTTTCCAAAAAGGGGTTGCAAAAAATTT

TGAACGTGCAAAAAAAATTACCAATAATCCAGAAAATTATTATCATGGATTCTAAAACGGATTACCAGG

GATTTCAGTCGATGTACACGTTCGTCACATCTCATCTACCTCCCGGTTTTAATGAATACGATTTTGTAC

CAGAGTCCTTTGATCGTGACAAAACAATTGCACTGATAATGAATTCCTCTGGATCTACTGGGTTACCT

AAGGGTGTGGCCCTTCCGCATAGAACTGCCTGCGTCAGATTCTCGCATGCCAGAGATCCTATTTTTG

GCAATCAAATCATTCCGGATACTGCGATTTTAAGTGTTGTTCCATTCCATCACGGTTTTGGAATGTTTA

CTACACTCGGATATTTGATATGTGGATTTCGAGTCGTCTTAATGTATAGATTTGAAGAAGAGCTGTTTT

TACGATCCCTTCAGGATTACAAAATTCAAAGTGCGTTGCTAGTACCAACCCTATTTTCATTCTTCGCCA

AAAGCACTCTGATTGACAAATACGATTTATCTAATTTACACGAAATTGCTTCTGGGGGCGCACCTCTTT

CGAAAGAAGTCGGGGAAGCGGTTGCAAAACGCTTCCATCTTCCAGGGATACGACAAGGATATGGGC

TCACTGAGACTACATCAGCTATTCTGATTACACCCGAGGGGGATGATAAACCGGGCGCGGTCGGTAA

AGTTGTTCCATTTTTTGAAGCGAAGGTTGTGGATCTGGATACCGGGAAAACGCTGGGCGTTAATCAG

AGAGGCGAATTATGTGTCAGAGGACCTATGATTATGTCCGGTTATGTAAACAATCCGGAAGCGACCA

ACGCCTTGATTGACAAGGATGGATGGCTACATTCTGGAGACATAGCTTACTGGGACGAAGACGAACA

CTTCTTCATAGTTGACCGCTTGAAGTCTTTAATTAAATACAAAGGATATCAGGTGGCCCCCGCTGAAT

TGGAATCGATATTGTTACAACACCCCAACATCTTCGACGCGGGCGTGGCAGGTCTTCCCGACGATGA

CGCCGGTGAACTTCCCGCCGCCGTTGTTGTTTTGGAGCACGGAAAGACGATGACGGAAAAAGAGAT

CGTGGATTACGTCGCCAGTCAAGTAACAACCGCGAAAAAGTTGCGCGGAGGAGTTGTGTTTGTGGA

-continued

CGAAGTACCGAAAGGTCTTACCGGAAAACTCGACGCAAGAAAAATCAGAGAGATCCTCATAAAGGCC

AAGAAGGGCGGAAAGTCCAAATTGgtttAA

Amino Acid Sequence for GST-(TEV-Ala)-Luc (SEQ ID NO: 12)

SPILGYVVKIKGLVQPTRLLLEYLEEKYEEHLYERDEGDKWRNKKFELGLEFPNLPYYIDGDVKLTQSMAIIR

YIADKHNMLGGCPKERAEISMLEGAVLDIRYGVSRIAYSKDFETLKVDFLSKLPEMLKMFEDRLCHKTYLN

GDHVTHPDFMLYDALDVVLYMDPMCLDAFPKLVCFKKRIEAIPQIDKYLKSSKYIAWPLQGWQATFGGGD

HPPKSGGGGGENLYFQAIAMEDAKNIKKGPAPFYPLEDGTAGEQLHKAMKRYALVPGTIAFTDAHIEVNIT

YAEYFEMSVRLAEAMKRYGLNTNHRIVVCSENSLQFFMPVLGALFIGVAVAPANDIYNERELLNSMNISQP

TVVFVSKKGLQKILNVQKKLPIIQKIIIMDSKTDYQGFQSMYTFVTSHLPPGFNEYDFVPESFDRDKTIALIM

NSSGSTGLPKGVALPHRTACVRFSHARDPIFGNQIIPDTAILSVVPFHHGFGMFTTLGYLICGFRVVLMYRF

EEELFLRSLQDYKIQSALLVPTLFSFFAKSTLIDKYDLSNLHEIASGGAPLSKEVGEAVAKRFHLPGIRQGY

GLTETTSAILITPEGDDKPGAVGKVVPFFEAKVVDLDTGKTLGVNQRGELCVRGPMIMSGYVNNPEATNA

LIDKDGWLHSGDIAYWDEDEHFFIVDRLKSLIKYKGYQVAPAELESILLQHPNIFDAGVAGLPDDDAGELPA

AVVVLEHGKTMTEKEIVDYVASQVTTAKKLRGGVVFVDEVPKGLTGKLDARKIREILIKAKKGGKSKLV

Nucleotide Sequence for GST-(TEV-Ala)-Luc (SEQ ID NO: 13)

atgtccctatactaggttattggaaaattaagggccttgtgcaacccactcgacttcttttggaatatcttgaagaaaaatatgaagagcatttgtatgag cgcgatgaaggtgataaatggcgaaacaaaaagtttgaattgggtttggagtttcccaatcttccttattatattgatggtgatgttaaattaacacagtct atggccatcatacgttatatagctgacaagcacaacatgttgggtggttgtccaaaagagcgtgcagagatttcaatgcttgaaggagcggttttggat attagatacggtgtttcgagaattgcatatagtaaagactttgaaactctcaaagttgattttcttagcaagctacctgaaatgctgaaaatgttcgaagat cgtttatgtcataaaacatatttgaatggtgatcatgtaacccatcctgacttcatgttgtatgacgctcttgatgttgttttatacatggacccaatgtgcc tggatgcgttcccaaaattagtttgtttcaaaaaacgtattgaagctatcccacaaattgataagtacttgaaatccagcaagtatatagcatggcctttgca gggctggcaagccacgtttggtggtggcgaccatcctccaaaatccggaggtggtggcggagaaaacctgtacttccaagcgatcgccATGGA

AGACGCCAAAAACATAAAGAAAGGCCCGGCGCCATTCTATCCTCTAGAGGATGGAACCGCTGGAGA

GCAACTGCATAAGGCTATGAAGAGATACGCCCTGGTTCCTGGAACAATTGCTTTTACAGATGCACATA

TCGAGGTGAACATCACGTACGCGGAATACTTCGAAATGTCCGTTCGGTTGGCAGAAGCTATGAAACG

ATATGGGCTGAATACAAATCACAGAATCGTCGTATGCAGTGAAAACTCTCTTCAATTCTTTATGCCGG

TGTTGGGCGCGTTATTTATCGGAGTTGCAGTTGCGCCCGCGAACGACATTTATAATGAACGTGAATT

GCTCAACAGTATGAACATTTCGCAGCCTACCGTAGTGTTTGTTTCCAAAAAGGGGTTGCAAAAAATTT

TGAACGTGCAAAAAAAATTACCAATAATCCAGAAAATTATTATCATGGATTCTAAAACGGATTACCAGG

GATTTCAGTCGATGTACACGTTCGTCACATCTCATCTACCTCCCGGTTTTAATGAATACGATTTTGTAC

CAGAGTCCTTTGATCGTGACAAAACAATTGCACTGATAATGAATTCCTCTGGATCTACTGGGTTACCT

AAGGGTGTGGCCCTTCCGCATAGAACTGCCTGCGTCAGATTCTCGCATGCCAGAGATCCTATTTTTG

GCAATCAAATCATTCCGGATACTGCGATTTTAAGTGTTGTTCCATTCCATCACGGTTTTGGAATGTTTA

CTACACTCGGATATTTGATATGTGGATTTCGAGTCGTCTTAATGTATAGATTTGAAGAAGAGCTGTTTT

TACGATCCCTTCAGGATTACAAAATTCAAAGTGCGTTGCTAGTACCAACCCTATTTTCATTCTTCGCCA

AAAGCACTCTGATTGACAAATACGATTTATCTAATTTACACGAAATTGCTTCTGGGGGCGCACCTCTTT

CGAAAGAAGTCGGGGAAGCGGTTGCAAAACGCTTCCATCTTCCAGGGATACGACAAGGATATGGGC

TCACTGAGACTACATCAGCTATTCTGATTACACCCGAGGGGATGATAAACCGGGCGCGGTCGGTAA

AGTTGTTCCATTTTTTGAAGCGAAGGTTGTGGATCTGGATACCGGGAAAACGCTGGGCGTTAATCAG

AGAGGCGAATTATGTGTCAGAGGACCTATGATTATGTCCGGTTATGTAAACAATCCGGAAGCGACCA

ACGCCTTGATTGACAAGGATGGATGGCTACATTCTGGAGACATAGCTTACTGGGACGAAGACGAACA

-continued

```
CTTCTTCATAGTTGACCGCTTGAAGTCTTTAATTAAATACAAAGGATATCAGGTGGCCCCCGCTGAAT

TGGAATCGATATTGTTACAACACCCCAACATCTTCGACGCGGGCGTGGCAGGTCTTCCCGACGATGA

CGCCGGTGAACTTCCCGCCGCCGTTGTTGTTTTGGAGCACGGAAAGACGATGACGGAAAAAGAGAT

CGTGGATTACGTCGCCAGTCAAGTAACAACCGCGAAAAAGTTGCGCGGAGGAGTTGTGTTTGTGGA

CGAAGTACCGAAAGGTCTTACCGGAAAACTCGACGCAAGAAAAATCAGAGAGATCCTCATAAAGGCC

AAGAAGGGCGGAAAGTCCAAATTGgtttA
```

Step B). Expression of Fusion Proteins.

Cultures of bacteria transformed with the confirmed plasmids were grown and induced for protein expression. After growth of the cultures, expression of the generation of a fusion protein of the expected size was confirmed by SDS PAGE fractionation of a sample of the cells with Coomassie Blue staining to detect the protein bands. Expression of the fusion proteins was estimated to be 1-5% of the total soluble protein in the cell lysates.

Step C). Purification of the Fusion Proteins.

After growth of the cultures, the cells were collected by centrifugation and frozen at −20° C. until ready for processing. Once ready for purification, the cell pellets were thawed and resuspended in a buffer A (1×PBS, pH 7.3, 1 mM PMSF, 1 Roche complete protease tablet per 50 mL), and cells were resuspended in this buffer at a ratio of 8-10 mL of buffer per gram cell paste. The cells were then lysed by sonication and insoluble cell debris precipitated by centrifugation of the lysed cells at 3900×G for 10 minutes at 4° C.

After centrifugation, the supernatant above the pellet was carefully removed and applied to a column of Glutathione sepharose (from GE Healthcare) equilibrated in 1×PBS, pH 7.3. After application, the column was washed with 10-20 column volumes of 1×PBS buffer (pH 7.3), then a solution containing 10-15 mM glutathione in 50 mM Tris-HCl buffer (pH 8.0) was applied to elute the protein. Fractions of the eluted materials were collected during this process and a small amount of the fractions were analyzed by SDS PAGE. As expected, the fusion proteins were greatly enriched in the fractions where the column buffer containing glutathione were eluting from the column. The fractions with the greatly enriched fusion protein were pooled and dialyzed against 10 mM HEPES buffer (pH 7.5, 50 mM NaCl).

Step D). Digestion and Labeling of the Fusion Proteins.

The protein concentration of the dialyzed fusion proteins were determined by use of Pierce's Coomassie Plus protein reagent per the manufacturer's protocol. Equal amounts of the paired protein constructs were diluted to ~1 uM in ProTEV Protease buffer. ProTEV was added and fusion proteins were digested overnight at 4° C. ProTEV buffer was 50 mM HEPES, pH 7.0, 0.5 mM EDTA, 1 mM DTT. The samples of the digests were analyzed by SDS PAGE. The fusion construct with an alanine following the TEV cleavage site and the construct with a cysteine following the site were both digested to greater than 90% based upon the appearance of new protein species the expected size for cleavage of the constructs at the TEV site and disappearance of the intact fusion protein band.

Samples of the two digests were then placed in fresh tubes containing 10 mM HEPES, pH 7.5, and a sample of PBI compound 3028 added from a 2 mM acetonitrile stock (as in FIG. 3; DMSO can also be used) to produce a final concentration of 10 μM PBI 3028. When using DMSO as a solvent, a 6.5 mM stock solution was used. At set time intervals, samples of these labeling reactions were added to new tubes containing a reagent to terminate the labeling reaction by reacting with the cyanobenzothiazole moiety of the labeling reagent; this solution contained cysteine-HCl (final concentration 1-5 mM in stop reactions) and an equal concentration of TCEP. It has also been found that a 10-fold lower concentration of TCEP is even more effective. This stop solution should be made in ~200 mM HEPES pH 8.0 in order to reduce acidity and prevent precipitation of proteins. Previous research had shown that reaction of this solution with the reagent rapidly converted the labeling reagent to the desired chemical species.

Figure 4:
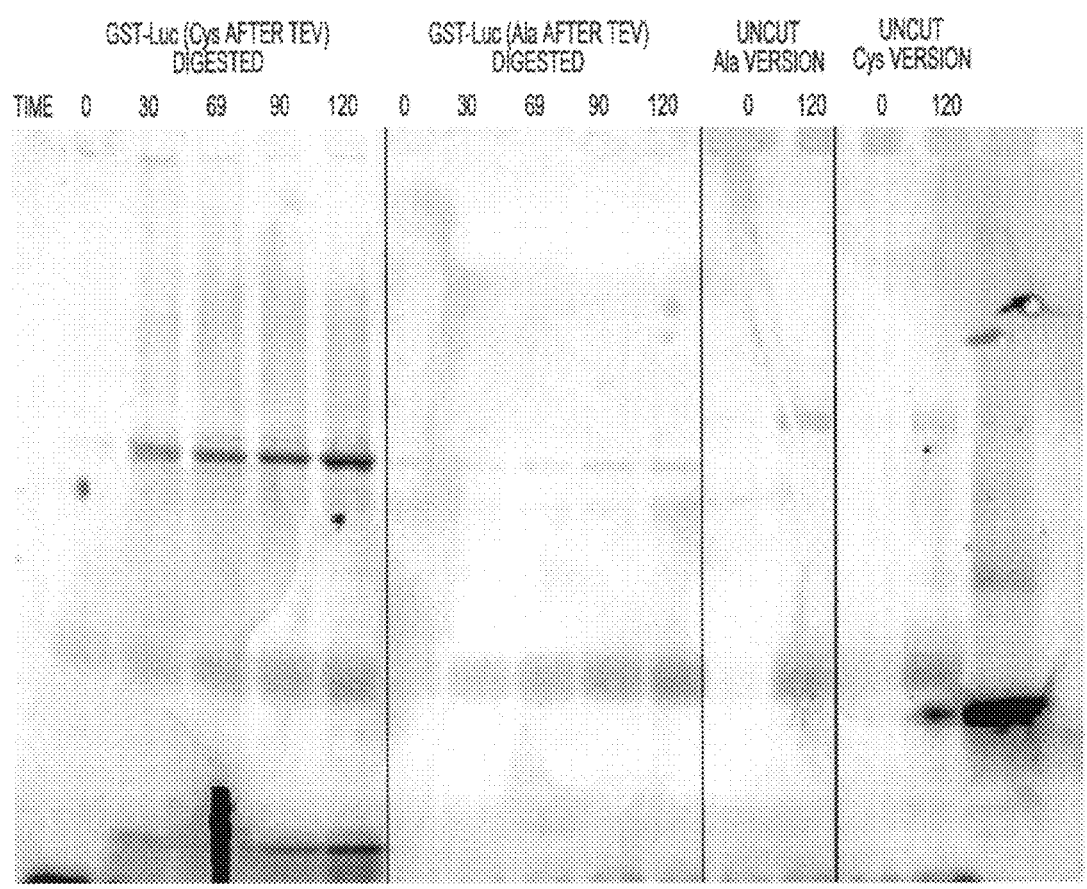
FIG. 4 illustrates the relative degree of labeling observed when a compound of the invention is incubated with a protein having an N-terminal cysteine residue versus an identical reaction where the protein having an N-terminal Cys residue is replaced with an equal amount of a protein differing from the N-terminal Cys protein only in that the second protein has an N-terminal alanine residue, both of which can be generated by cleavage with TEV protease, as described in Example 5.

After all the timed samples were collected, they were analyzed by SDS PAGE electrophoresis followed by imaging on the Typhoon. After imaging, the gels were stained with SimplyBlue SafeStain™ (Invitrogen) to visualize the protein bands. A comparison of the gel images obtained from fluorescent scanning of the gel prior to Coomassie staining and post-Coomassie staining was performed (Coomassie stained gel not shown). The fluorescent gel image is shown in FIG. 4. As seen in the fluorescent gel image, the Cys N-terminal protein partner in the incubations of the benzothiazole dye conjugate became highly fluorescent whereas the other protein species in these reactions, which are visible on the Coomassie stained gel, underwent little or no labeling at all (digested Cys after TEV samples vs. digested Ala after TEV). In addition, the reactions where cleavage with TEV protease resulted in the new protein species having an amino terminal alanine did not become highly fluorescently labeled. Finally, very little or no labeling is seen where the fusion protein constructs are not digested with TEV protease (uncut Ala version and Cys versions of the fusion protein). Thus, the cysteine residue that allows strong labeling of the digested fusion protein construct does not become highly labeled if it is exposed to the reagent at an internal cysteine residue. The large dark spot on the bottom right of the figure arises from the colored protein standard loaded in that lane.

These observations demonstrate that there is at least a very strong preference for labeling of an N-terminal cysteine residue with the compounds of the invention, if not completely specific labeling. Also, the labeling is dependent upon the N-terminal residue of the protein being a cysteine residue and such a protein can be generated by digestion of a fusion protein construct by a protease.

Example 5

Confirmation of N-Terminal Labeling of Proteins Fluorescently Tagged with a Cyanobenzothiazole Labeling Reagent In this example, a very specific fusion protein construct is labeled with various cyanobenzothiazole labeling reagents. The protein is then exposed to a second site-specific protease that cleaves the TEV digested protein a second time only a few amino acids from the new amino terminus. This cleavage allows for the examination of the specificity of labeling achieved prior to the second digestion. Accordingly, all of the fluorescence on digested protein should be eliminated by action of the second protease if the protein is exclusively labeled at the new amino terminus. If the protein is labeled at multiple sites, however, treatment of the labeled protein with the second protease will generate a second protein species slightly smaller than the initial product that is still highly fluorescent.

A fusion construct was produced that had a double protease cleavage site between two protein partners with the order of segments being GST-TEV protease site—Cys-Factor Xa protease site—HaloTag (version 2). This protein was expressed in E. coli and purified by use of an affinity resin for GST fusion proteins (typically GE Healthcare Glutathione sepharose 4 fast flow) according to the instructions of the supplier.

The purity of the isolated fusion protein was examined by SDS PAGE electrophoresis and found to contain a large amount of the desired full length protein. This protein was dialyzed and then digested with ProTEV protease. Following cleavage, samples of the digest were labeled with cyanobenzothiazole labeling agents with different attached dye segments. A separate sample was labeled with the HaloTag TMR ligand, which has been shown to label HaloTag protein well within the protein sequence. For information on HaloTag® technology and use of the HaloTag TMR ligand, see the Technical Manual *HaloTag® Technology: Focus on Imaging*, Part # TM260, available from Promega Corporation and M. Urh et al., "Halolink™ Resin For Protein Pull-Down And Analysis" *Cell Notes* 2006, 14, 15-19, available from Promega Corporation.

After labeling, samples of the purified protein labeled with each agent were digested with Factor Xa. Following Factor Xa digestion, samples of the undigested labeled protein and Factor Xa digested labeled protein were fractionated on an SDS PAGE gel and the gel was imaged on a Typhoon imager. After imaging, the gel was stained with Coomassie brilliant blue to visualize the proteins using a method that would not rely on the fluorescence of the protein. The images of the fluorescent gel images and Coomassie stained gels are shown in FIG. 5.

Figure 5A:
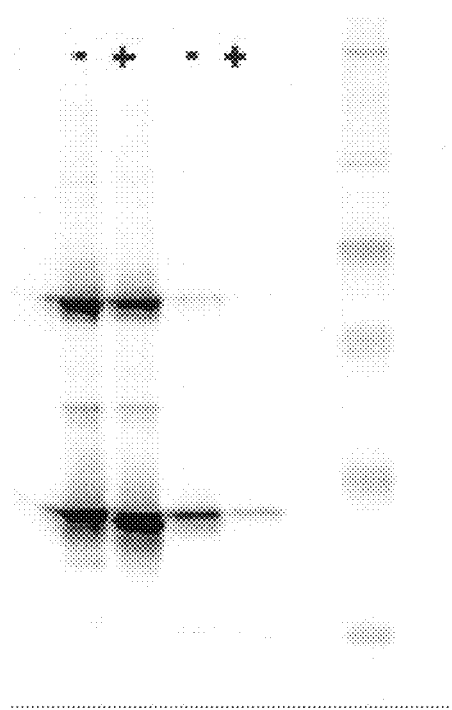
FIG. 5 shows the fluorescent gel images and Coomassie stained gels prepared according to Example 5, illustrating that a protein with an N-terminal cysteine can be prepared by cleaving a fusion construct with TEV protease. The protein can be labeled at its N-terminus with a cyanobenzothiazole reagent, which can then be selectively cleaved with a second protease in a subsequent step.
Figure 5B:
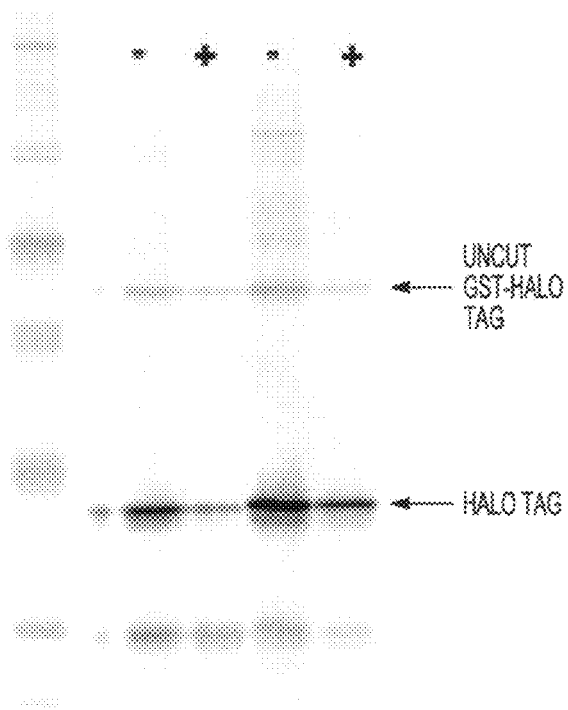
Figure 5C:
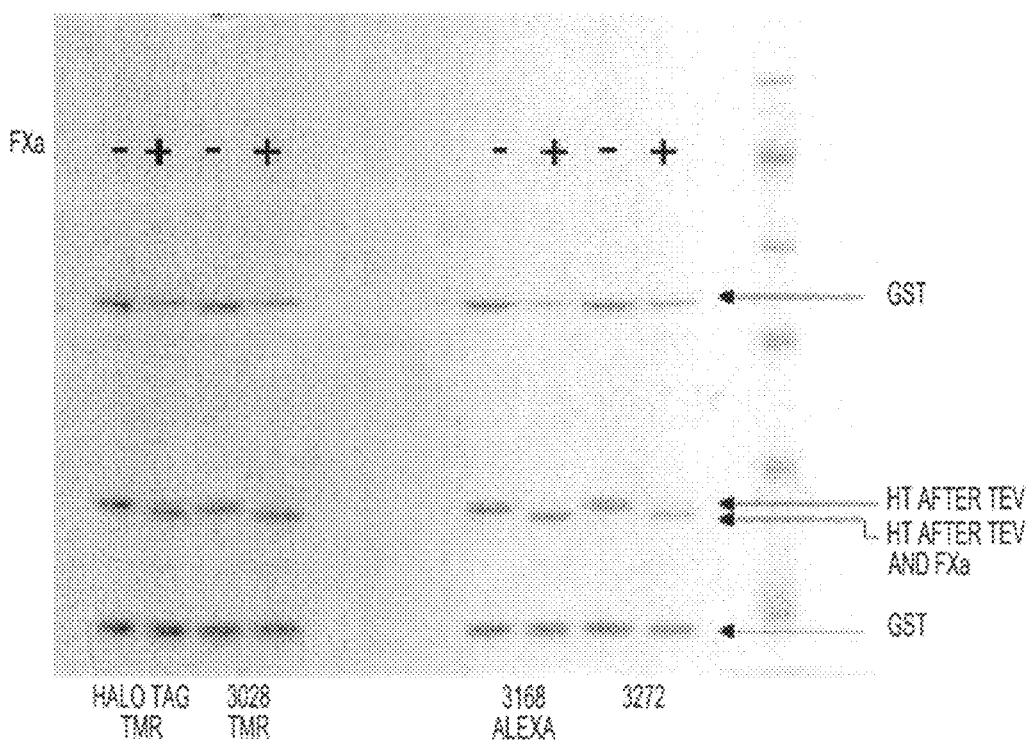

As expected, when the fusion construct was labeled with HaloTag ligand (thus labeling the protein partner expected to be labeled with the cyanobenzathiazole reagents, but attaching the label at approximately in the middle of the protein segment) and digested with Factor Xa, the labeled protein only changed slightly in size and retained its fluorescence (first two lanes of gel in FIG. 5). However, when the samples labeled with the cyanobenzathiazole reagents were digested, almost all of the fluorescence associated with the labeled protein band was eliminated from the protein, except for a very small amount of fluorescence associated with a protein species with the mobility of the initial labeled protein (pairs of lanes illustrating loss of fluorescence in FIG. 5 denoted 3028 TMR, 3168 Alexa, and 3272).

When this segment of the gel was stained with Comassie, a large amount of protein slightly smaller than the labeled protein was found to be present in the lanes where the fusion protein was treated with Factor Xa (bottom panel, FIG. 5). Because this protein band was not fluorescent, yet arose from removal of only a few amino acids from the amino terminus of the labeled protein, the fluorescent label must have been on the few amino acids digested off the construct—the amino terminus of the labeled protein species.

Figure 6:
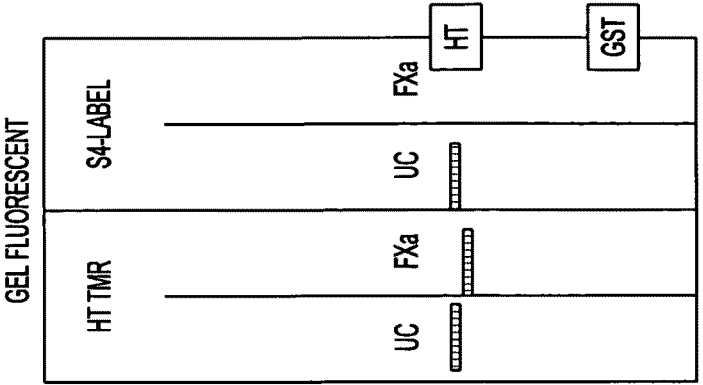
FIG. 6 illustrates peptide chain cleavage and Coomassie stained gels for peptides exclusively labeled at the N-terminus, according to the procedure of Example 5. The abbreviation CN-BT indicates a cyanobenzothiazole derivative reagent as described herein; HT=HaloTag; GST=Glutathione-S-tranferase; TMR=tetramethylrhodamine; UC=uncut; and FXa=Factor Xa protease cut.
Figure 6:
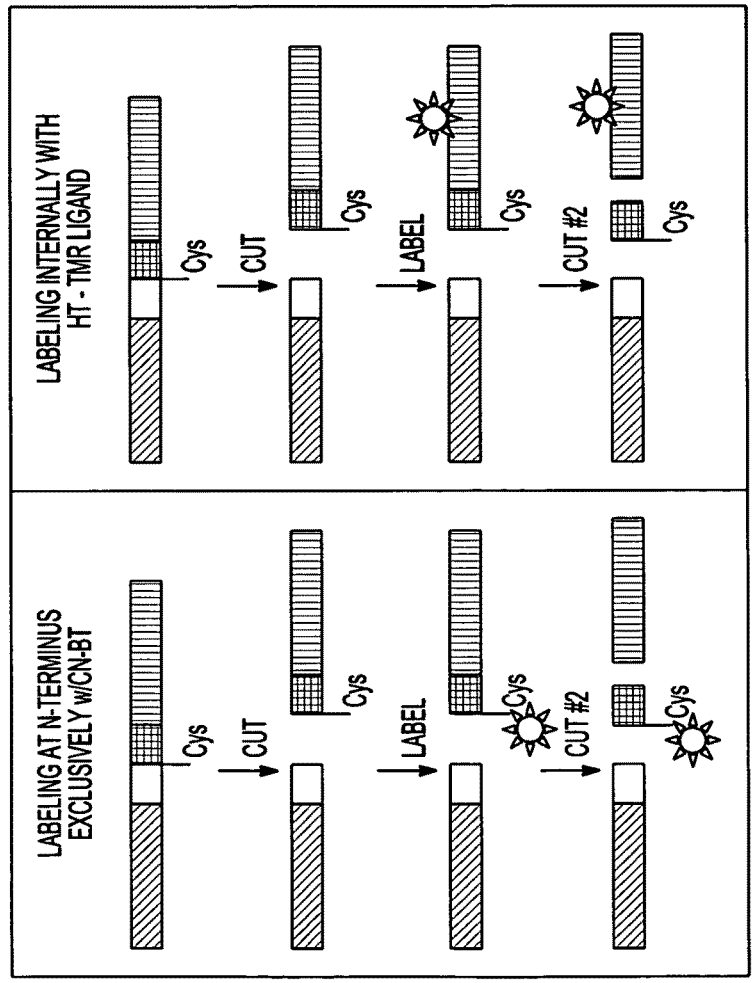
Figure 7:
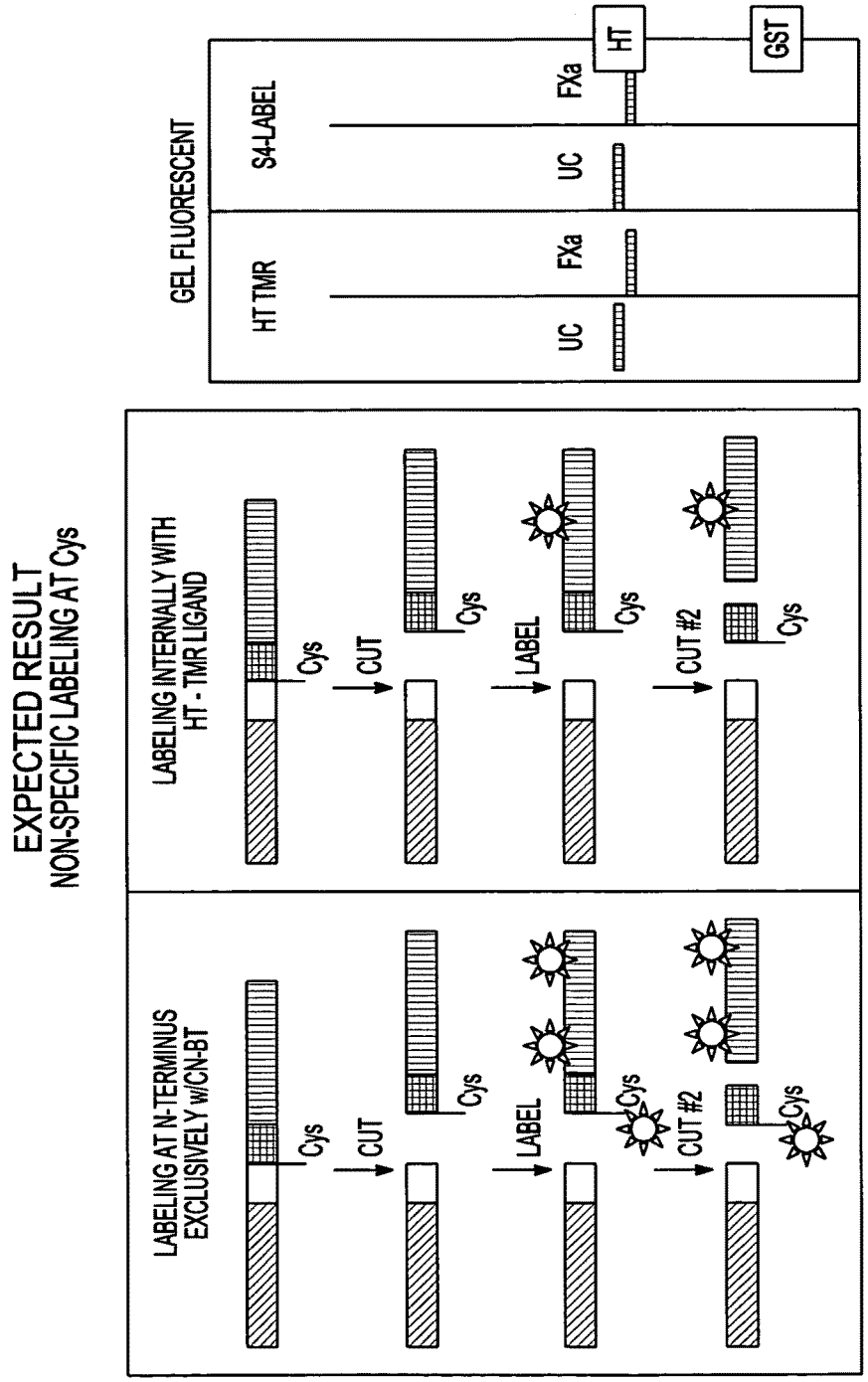
FIG. 7 illustrates peptide chain cleavage and Coomassie stained gels for non-specifically labeled peptides (both internal cysteines and N-terminal cysteines), according to the procedure of Example 5. The abbreviation CN-BT indicates a cyanobenzothiazole derivative reagent as described herein; HT=HaloTag; GST=Glutathione-5-tranferase; TMR=tetramethylrhodamine; UC=uncut; and FXa=Factor Xa protease cut.

FIGS. 5, 6, and 7 illustrate cleavage results and representative gels of the results expected from labeling exclusively at the N-terminus, and non-specific labeling at cysteine residues, respectively.

If a cyanobenzothiazole labeling reagent labels only the N-terminus and not internal cysteines as illustrated in FIG. 6, one would expect to see the cyanobenzothiazole label on the protein of interest to be removed with cleavage of the protein at a protease site downstream from the label. An internal label, such as a HaloTag ligand control, would not be removed with cleavage of the protein with the second protease. A fluorescent scan of an SDS-PAGE gel of these samples would show the disappearance of fluorescence from the cyanobenzothiazole labeled band after cleavage with the second protease. The HaloTag ligand labeled protein would show a shift in size but would remain fluorescent because the fluorescent label was not removed, which is illustrated in the fluorescent gel diagram of FIG. 6.

If the cyanobenzothiazole labeling reagent attaches to internal cysteines as illustrated in FIG. 7, one would expect the cleavage of the labeled protein with a second protease to leave a fluorescent band of a lower molecular weight, which would appear substantially similar to a HaloTag ligand labeled control protein, which is illustrated in the fluorescent gel diagram of FIG. 7.

```
Amino Acid Sequence for GST-(TEV-Cys-FXa)-HaloTag
                                                                               (SEQ ID NO: 14)
MSPILGYWKIKGLVQPTRLLLEYLEEKYEEHLYERDEGDKWRNKKFELGLEFPNLPYYIDGDVKLTQSMAII

RYIADKHNMLGGCPKERAEISMLEGAVLDIRYGVSRIAYSKDFETLKVDFLSKLPEMLKMFEDRLCHKTYL

NGDHVTHPDFMLYDALDVVLYMDPMCLDAFPKLVCFKKRIEAIPQIDKYLKSSKYIAWPLQGWQATFGGG

DHPPKSGGGGENLYFQCIAMIEGRAMGSEIGTGFPFDPHYVEVLGERMHYVDVGPRDGTPVLFLHGNP

TSSYLWRNIIPHVAPSHRCIAPDLIGMGKSDKPDLDYFFDDHVRYLDAFIEALGLEEVVLVIHDWGSALGFH

WAKRNPERVKGIACMEFIRPIPTWDEWPEFARETFQAFRTADVGRELIIDQNAFIEGALPMGVVRPLTEVE

MDHYREPFLKPVDREPLWRFPNELPIAGEPANIVALVEAYMNWLHQSPVPKLLFWGTPGVLIPPAEAARL

AESLPNCKTVDIGPGLFLLQEDNPDLIGSEIARWLPGLV

Nucleotide sequence for GST-(TEV-Cys-FXa)-HaloTag
                                                                               (SEQ ID NO: 15)
atgtcccctatactaggttattggaaaattaagggccttgtgcaacccactcgacttcttttggaatatcttgaagaaaaatatgaagagcatttgtatgag cgcgatgaaggtgataaatggcgaaacaaaaagtttgaattgggtttggagtttcccaatcttccttattatattgatggtgatgttaaattaacacagtct
```

-continued

```
atggccatcatacgttatatagctgacaagcacaacatgttgggtggttgtccaaaagagcgtgcagagatttcaatgcttgaaggagcggttttggat attagatacggtgtttcgagaattgcatatagtaaagactttgaaactctcaaagttgattttcttagcaagctacctgaaatgctgaaaatgttcgaagat cgtttatgtcataaaacatatttgaatggtgatcatgtaaccatcctgacttcatgttgtatgacgctcttgatgttgttttatacatggaccaatgtgcc tggatgcgttcccaaaattagtttgtttcaaaaaacgtattgaagctatcccacaaattgataagtacttgaaatccagcaagtatatagcatggcctttgca gggctggcaagccacgtttggtggtggcgaccatcctccaaaatccggaggtggtggcggagaaaacctgtacttccaatgcatcgctatgataga gggtagagctatgggatccgaaatcggtacaggcttcccttcgaccccattatgtggaagtcctgggcgagcgtatgcactacgtcgatgttggac cgcgggatggcacgcctgtgctgttcctgcacggtaacccgacctcgtcctacctgtggcgcaacatcatcccgcatgtagcaccgagtcatcggtg cattgctccagacctgatcgggatgggaaaatcggacaaaccagacctcgattatttcttcgacgaccacgtccgctacctcgatgccttcatcgaag ccttgggtttggaagaggtcgtcctggtcatccacgactgggctcagctctcggattccactgggccaagcgcaatccggaacgggtcaaaggtatt gcatgtatggaattcatccggcctatcccgacgtgggacgaatggccagaattcgcccgtgagaccttccaggccttccggaccgccgacgtcggc cgagagttgatcatcgatcagaacgctttcatcgagggtgcgctcccgatggggtcgtccgtccgcttacggaggtcgagatggaccactatcgcg agcccttcctcaagcctgttgaccgagagccactgtggcgattcccaacgagctgcccatcgccggtgagcccgcgaacatcgtcgcgctcgtcg aggcatacatgaactggctgcaccagtcacctgtcccgaagttgttgttctggggcacaccggcgtactgatcccccggccgaagccgcgagac ttgccgaaagcctcccaactgcaagacagtggacatcggcccgggattgttcttgctccaggaagacaacccggaccttatcggcagtgagatcg cgcgctggctccccgggctggtttaa
```

Example 6

Use of Labeled Protein in Protein Interaction Reactions

This example demonstrates that protein labeled with benzothiazole dye conjugates can be used in protein interaction studies. In order to easily identify proteins that were expressed in the cell free expression systems without relying on labeling with a compound of the invention, parallel protein expression reactions were performed where one of the sets of the reactions contained FluoroTect™ Green$_{Lys}$ in vitro Translation Labeling System (Promega Corp). Proteins expressed with FluoroTect become fluorescently labeled with a dye that is added internal to the termini of the protein. The label is detected by exposing a sample of the protein to 488 nm light and detecting emitted light above 510 nm. Use of this particular second labeling method allows labeling of a protein by FluoroTect to be easily distinguished from a signal from a compound of the invention used to label an N-terminus of a protein. A protein labeled at its N-terminus with a compound of the invention is not appreciably excited by light at 488 nm, but is strongly excited by light at 633 nm. On the other hand, the FluoroTect dye is not excited to an appreciable degree by light at 633 nm but is strongly excited by light at 488 nm. Thus, by scanning a sample from the reactions below using separate excitation wavelengths of 488 nm and 633 nm, one can distinguish protein species made in the in vitro protein synthesis reaction from those labeled using the compound of the invention.

Three 250 μL translation reactions were performed by adding 20 μg of the indicated DNAs to reactions using SP6 TnT High Yield Extract (Promega Corp., Madison, Wis.) assembled in the reactions as recommended by the supplier. The three constructs added encoded: 1) a fusion protein between HaloTag and the catalytic subunit of protein kinase A; 2) a construct expressing a metal binding peptide followed by a TEV cleavage site followed by a Cysteine residue and the regulatory subunit of protein kinase A (also known as RI alpha), and; 3) a third reaction identical to number two, but also containing 10 μL of FluoroTect (Promega Corp). The reactions were allowed to incubate at 25° C. for 120 minutes.

A 225 μL sample of the three translation reactions were processed through microbiospin columns (BioRad) according to the manufacturers recommendations following the 120 minute incubation. After microbiospin processing, 12 μL of 20×ProTEV buffer, 2.4 μL of 0.1 M DTT, and ~10 U ProTEV protease (Promega Corp.) were added and the tubes incubated for 60 minutes at room temperature. After TEV treatment, 30 μL MagneHis was used to remove the protease. To the processed lysate was added 2.8 μL of 2 mM TCEP and 3.8 μL of 125 μM PBI 3168 and the tubes were incubated for 60 minutes at room temperature. Finally, freshly reduced cysteine was added to these tubes to react with any excess benzothiazole reagent.

A 400 μL sample of HaloLink Magnetic Beads (Promega Corporation Catalog #G9311) was washed and resuspended in 300 μL as per the manufacturers recommendation, then 50 μL of slurry was used to capture HaloTag fusion proteins from 50 μL of SP6 translation reactions, again as described by the manufacturer. Other HaloLink resins such as Promega Cat. #G1911 or Cat. #G1912 can also be used. See M. Urh et al., "Halolink™ Resin For Protein Pull-Down And Analysis" Cell Notes 2006, 14, 15-19. After washing, the resin was resuspended in kinase buffer (40 mM Tris-HCl, pH 7.5, 20 mM MgCl$_2$, 0.1 mg/mL BSA) and the resin was incubated with the cyanobenzothiazole labeled prey proteins. After these incubations and washing with 1× wash buffer, samples of the protein solutions were fractionated on SDS PAGE gels, analyzed by SDS PAGE electrophoresis, and the gels were imaged using excitation with 633 nm laser.

Figure 8A:
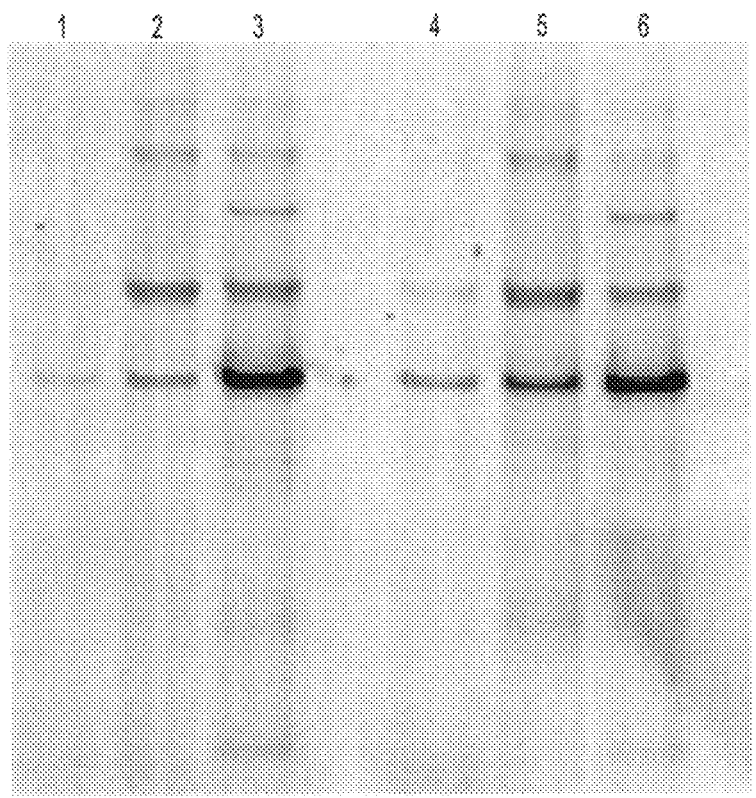
FIGS. 8(a) and 8(b) illustrate the results of a label used to detect protein:protein interactions as described in Example 6.
Figure 8B:
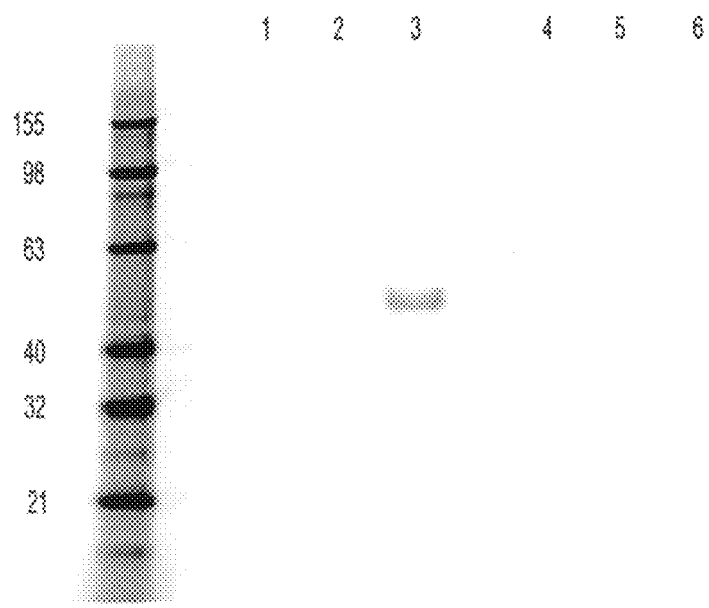

Visualization of the image produced by scanning with a lazar for detection of the Fluorotect product showed specific protein pull-down (FIG. 8(b)). Scanning the gels of FIG. 8 with a 633 nm laser shows the detection of the pulldown with a red cyanobenzothiazole-derived dye. More interaction was observed with the sample versus the control resin, which demonstrates that the label can be used to detect protein:protein interactions.

FIG. 8(a), scanned at a wavelength that showed only the red cyanobenzothiazole dye label, shows pulldown scanning for fluorescence of PBI 3168 (prepared from Alexa 633 SE and the corresponding primary amine linked to a cyanobenzothiazole; releases light fluorescently after excitation by light of 633 nm). In FIG. 8(b), the same gel, was scanned for Fluorotect. All are pulldowns; bait and prey are as follows:

Lanes 1+4, Bait=buffer, Prey=RI-alpha.

Lanes 2+5, Bait=TNT High Yield Lysate (no translation), Prey=RI-alpha.

Lanes 3+6, Bait is HaloTag-PKA, Prey=RI-alpha.

Samples in lanes 1-3 were Fluorotect labeled during translation and 4-6 were not. The far red (633 nm) was used because of its spectral separation from Fluorotect so no crosstalk between dyes was observed. In FIG. 8(b), a doublet of RI-alpha can be seen because a small amount was not cleaved by TEV. The faint band much higher on the gel is likely an oligomer and is also present in FIG. 8(a). While there is some non-specifically labeled species in this cyanobenzothiazole-labeled example, the ability to use the cyanobenzothiazole-labeling method to detect protein:protein interactions is clearly demonstrated.

Scanning the gel with the 488 nm or 523 nm lasers allowed specific pull down of RI alpha by Immobilized PKA. Much less capture of this protein was seen if it was added to the control resin, thus confirming that these results were being produced as a result of the well known interaction between PKA and the regulatory subunit of PKA.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

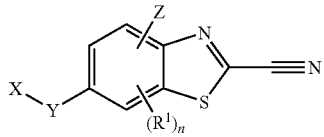

wherein

Z is H, F, Cl, Br, I, CN, amino, alkylamino, dialkylamino, alkyl ester, carboxy, carboxylic acid salt, alkyl amide, phosphate, alkyl phosphonate, sulfate, alkyl sulfonate, nitro, or $(C_1\text{-}C_{10})$alkyl optionally unsaturated and optionally substituted with amino, hydroxy, oxo (=O), nitro, thiol, or halo;

each $R^1$ is independently H, F, Cl, Br, I, CN, $(C_1\text{-}C_6)$alkyl, $(C_1\text{-}C_6)$alkoxy, or $(C_1\text{-}C_6)$alkylthio, wherein each alkyl, alkoxy, or alkylthio is optionally substituted with F, Cl, Br, I, amino, alkenyl, alkynyl, cycloalkyl, aryl, alkyl sulfonate, or $CO_2M$ wherein M is H, an organic cation, or an inorganic cation;

n is 0, 1, or 2;

Y is a linking group comprising $(C_1\text{-}C_{16})$alkyl optionally substituted with one or more halo, oxo (=O), $(C_1\text{-}C_6)$alkyl, or $(C_1\text{-}C_6)$alkoxy, and optionally interrupted with one or more $N(R^1)$, O, S, or —N—C(=O)— groups; or Y is optionally absent when X is $N_3$; and X is a fluorescent dye, biotin, HisTag, chitin, a solid support, $N_3$, H, or OH, provided that when X is H or OH, the compound of formula I comprises a radioactive moiety or an isotopic variant of any atom other than the carbon or nitrogen atom of the 2-nitrile moiety.

2. The compound of claim 1 wherein Z is H, F, nitro, or alkyl sulfonate, and $R^1$ is H or F.

3. The compound of claim 2 wherein Y is —$(C_1\text{-}C_6)$alkyl-, —O—$(C_1\text{-}C_6)$alkyl-, —O—$(C_1\text{-}C_6)$alkyl-O—, —O—$(C_1\text{-}C_6)$alkyl-NH—, —O—$(C_1\text{-}C_6)$alkyl-(CO)NH—, —NH—$(C_1\text{-}C_6)$alkyl-NH—, —NH—(CO)$(C_1\text{-}C_6)$alkyl-NH—, —NH—(CO)$(C_1\text{-}C_6)$alkyl-(CO)—NH—, or —O—$(C_1\text{-}C_6)$alkyl-(CO)NH—$(C_1\text{-}C_6)$alkyl-.

4. The compound of claim 3 wherein X is $N_3$, a fluorescent dye, biotin, HisTag, chitin, or a solid support.

5. The compound of claim 4, wherein X is $N_3$,

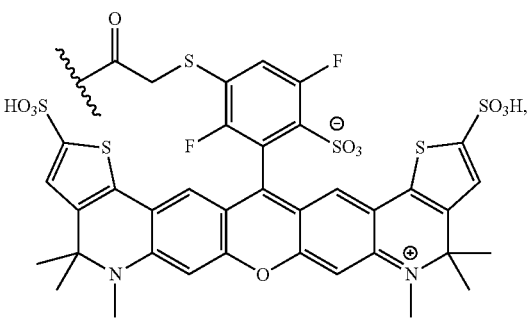

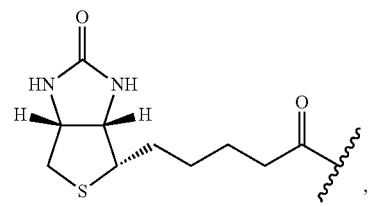

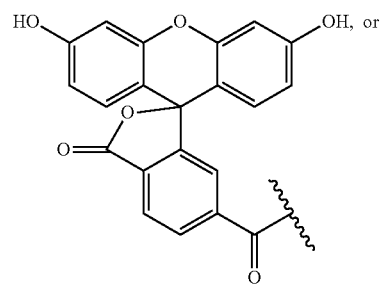

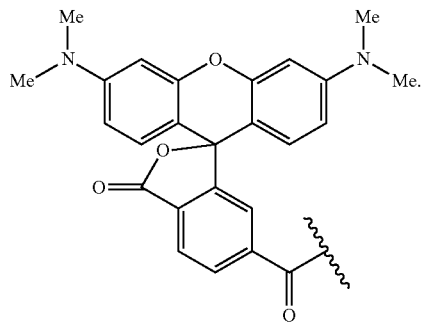

6. The compound of claim 1 wherein the compound of formula I is:

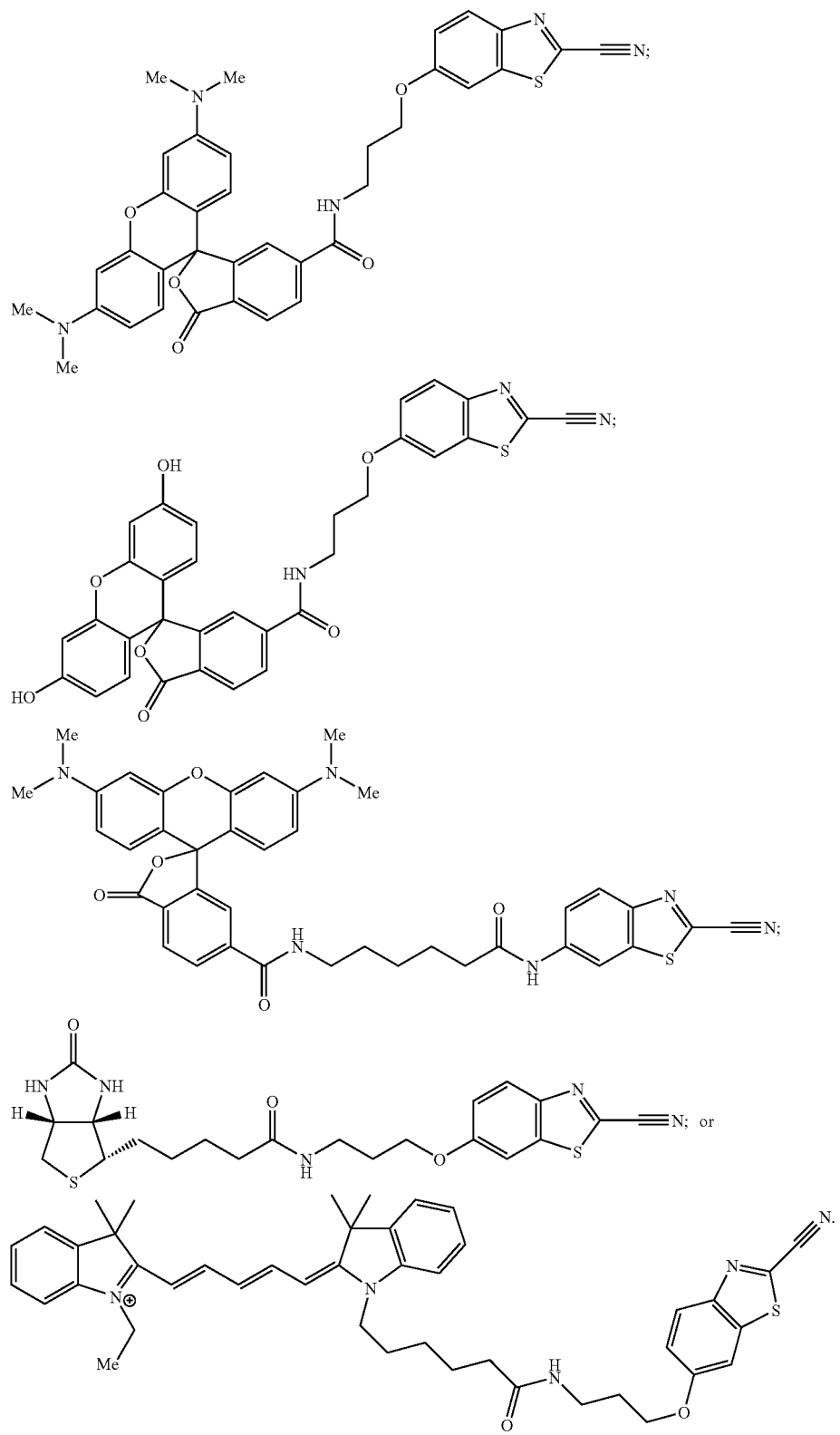
* * * * *